US012617751B2

United States Patent

Sivaguru et al.

(10) Patent No.: US 12,617,751 B2

(45) Date of Patent: May 5, 2026

(54) VISIBLE LIGHT ACTIVE BIOMASS DERIVED PHOTOINITIATORS

(71) Applicant: Bowling Green State University, Bowling Green, OH (US)

(72) Inventors: Jayaraman Sivaguru, Bowling Green, OH (US); Ravichandranath Singathi, Bowling Green, OH (US); Sruthy Baburaj, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 755 days.

(21) Appl. No.: 17/926,216

(22) PCT Filed: May 18, 2021

(86) PCT No.: PCT/US2021/032893

§ 371 (c)(1),
(2) Date: Nov. 18, 2022

(87) PCT Pub. No.: WO2021/236590

PCT Pub. Date: Nov. 25, 2021

(65) Prior Publication Data

US 2023/0183167 A1 Jun. 15, 2023

Related U.S. Application Data

(60) Provisional application No. 63/026,970, filed on May 19, 2020.

(51) Int. Cl.

*C07C 217/20* (2006.01)
*C07C 255/56* (2006.01)

(Continued)

(52) U.S. Cl.

CPC .......... *C07C 217/20* (2013.01); *C07C 255/56* (2013.01); *C07C 323/22* (2013.01);

(Continued)

(58) Field of Classification Search

None

See application file for complete search history.

(56) References Cited

U.S. PATENT DOCUMENTS 3,036,914 A 5/1962 Jennings
7,964,249 B2 * 6/2011 Cartellieri ................ C08F 8/00 525/131

(Continued)

FOREIGN PATENT DOCUMENTS

CN 101418051 A * 4/2009
CN 110520496 A * 11/2019 ............. C09J 7/381

(Continued)

OTHER PUBLICATIONS

Hepuzer et al. (1996), Photoactive epichlorohydrin, 2. Photoinitiated free-radical and promoted cationic polymerization by using polyepichlorohydrin with benzoin terminal groups. Angew. Makromol. Chem., 237: 163-171. (Year: 1996).*

(Continued)

*Primary Examiner* — Sanza L. McClendon

(74) *Attorney, Agent, or Firm* — MacMillan, Sobanski & Todd, LLC

(57) ABSTRACT

Biomass derived benzoin derivatives, and methods of making and using the same, are described. Benzoin derivatives may be used as visible light photoinitiators.

20 Claims, 48 Drawing Sheets
(43 of 48 Drawing Sheet(s) Filed in Color)

(51) Int. Cl.

| | |
|---|---|
| ***C07C 323/22*** | (2006.01) |
| ***C07D 303/23*** | (2006.01) |
| ***C07F 7/08*** | (2006.01) |
| ***C08F 2/50*** | (2006.01) |
| ***C08F 20/14*** | (2006.01) |

(52) U.S. Cl.

CPC ............ *C07D 303/23* (2013.01); *C07F 7/081* (2013.01); *C08F 2/50* (2013.01); *C08F 20/14* (2013.01)

(56) References Cited

U.S. PATENT DOCUMENTS

| | | | | |
|---|---|---|---|---|
| 8,519,076 | B2 * | 8/2013 | Erwin | B29C 48/435 526/78 |
| 8,841,354 | B2 * | 9/2014 | Nielsen | C08F 2/50 520/1 |
| 9,783,684 | B2 * | 10/2017 | Yamaguchi | C09D 5/00 |
| 9,932,499 | B2 * | 4/2018 | Zanzottera | A61L 15/58 |
| 2004/0005524 | A1 | 1/2004 | Oxman et al. | |
| 2005/0196617 | A1 | 9/2005 | King | |
| 2008/0121870 | A1 | 5/2008 | Seth et al. | |
| 2018/0272595 | A1 | 9/2018 | Yudovin-Farber et al. | |
| 2019/0047965 | A1 | 2/2019 | Sivaguru et al. | |

FOREIGN PATENT DOCUMENTS

| | | | | |
|---|---|---|---|---|
| CN | 120192650 | A * | 6/2025 | |
| DE | 102018222213 | A1 * | 6/2020 | C09J 7/385 |
| JP | 2013535990 | A * | 9/2013 | A61L 29/085 |
| JP | 2019192475 | A * | 10/2019 | |

OTHER PUBLICATIONS

L Angiolini et al. Polymeric photoinitiators having benzoin methylether moieties connected to the main chain through the benzyl aromatic ring and their activity for ultraviolet-curable coatings, Polymer, vol. 40, Issue 26, 1999, pp. 7197-7207. (Year: 1999).*

Esen et al. (2013), Benzoin type photoinitiator for free radical polymerization. J. Polymer Science: Part A Polymer Chemistry, 51, pp. 1865-1871 (Year: 2013).*

Wikipedia contributors. (Nov. 22, 2024). Benzoin condensation. In Wikipedia, The Free Encyclopedia. Retrieved Aug. 23, 2025, (Year: 2024).*

Pubchem, SID 229742610, Available Date Feb. 12, 2015 [Retrieved on Jun. 22, 2021]. Retrieved from the Internet: <URL;https://pubchem.ncbi.nlm.nih.gov/substance/229742610> entire document, pp. 1-8.

International Search Report and Written Opinion, Application No. PCT/US2021/032893, dated Nov. 8, 2021.

* cited by examiner 1a 1b 1c 1d 1e 1f 1g

Benzoin 1h

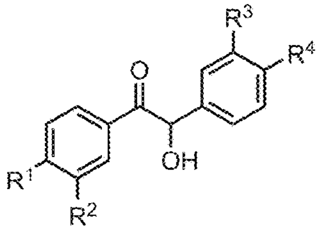

1

1a ;$R^1$ = $R^2$ = $R^3$ = $R^4$ = $OCH_3$
1b ; $R^1$ = $R^2$ = $OCH_3$; $R^3$ = H; $R^4$ = Cl
1c ; $R^1$ = $R^2$ = $OCH_3$; $R^3$ =H, $R^4$ = CN
1d ; $R^1$ = $R^2$ = $OCH_3$; $R^3$ =H, $R^4$ = $CF_3$
1e ; $R^1$ = Cl; $R^2$ = H; $R^3$ =$OCH_3$, $R^4$ = $OCH_3$
1f ; $R^1$ = CN; $R^2$ = H; $R^3$ =$OCH_3$, $R^4$ = $OCH_3$
1g; $R^1$ = $SCH_3$; $R^2$ = H; $R^3$ =$OCH_3$, $R^4$ = $OCH_3$
1h ;$R^1$ = $R^2$ = $R^3$ = $R^4$ = H

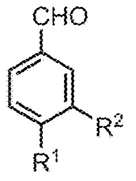

2

2a) $R^1$ = $R^2$ = $OCH_3$
2e) $R^1$ = Cl; $R^2$ = H
2f) $R^1$ = CN; $R^2$ = H
2g) $R^1$ = $SCH_3$; $R^2$ = H

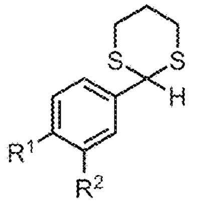

3

3a) $R^1$ = $R^2$ = $OCH_3$
3e) $R^1$ = Cl; $R^2$ = H
3f) $R^1$ = CN; $R^2$ = H
3g) $R^1$ = $SCH_3$; $R^2$ = H

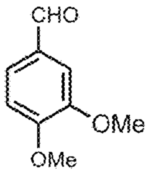

4a

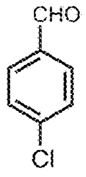

4b

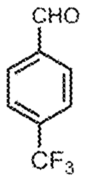

4d

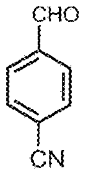

4c

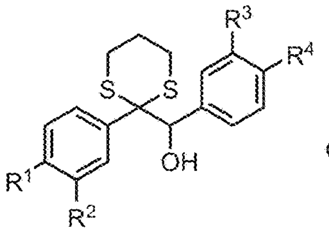

5

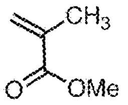

6

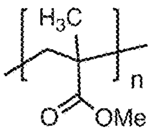

7

5a ;$R^1$ = $R^2$ = $R^3$ = $R^4$ = $OCH_3$
5b ; $R^1$ = $R^2$ = $OCH_3$; $R^3$ = H; $R^4$ = Cl
5c ; $R^1$ = $R^2$ = $OCH_3$; $R^3$ =H, $R^4$ = CN
5d ; $R^1$ = $R^2$ = $OCH_3$; $R^3$ =H, $R^4$ = $CF_3$
5e ; $R^1$ = Cl; $R^2$ = H; $R^3$ =$OCH_3$, $R^4$ = $OCH_3$
5f ; $R^1$ = CN; $R^2$ = H; $R^3$ =$OCH_3$, $R^4$ = $OCH_3$
5g; $R^1$ = $SCH_3$; $R^2$ = H; $R^3$ =$OCH_3$, $R^4$ = $OCH_3$

2a) $R^1 = R^2 = OCH_3$
2e) $R^1 = Cl$; $R^2 = H$
2f) $R^1 = CN$; $R^2 = H$
2g) $R^1 = SCH_3$; $R^2 = H$

3a) $R^1 = R^2 = OCH_3$
3e) $R^1 = Cl$; $R^2 = H$
3f) $R^1 = CN$; $R^2 = H$
3g) $R^1 = SCH_3$; $R^2 = H$

Cyanide free reaction

3 5

3a) $R^1 = R^2 = OCH_3$
3e) $R^1$ = Cl; $R^2$ = H
3f) $R^1$ = CN; $R^2$ = H
3g) $R^1 = SCH_3$; $R^2$ = H

5a ;$R^1 = R^2 = R^3 = R^4 = OCH_3$
5b ; $R^1 = R^2 = OCH_3$; $R^3$ = H; $R^4$ = Cl
5c ; $R^1 = R^2 = OCH_3$; $R^3$ =H, $R^4$ = CN
5d ; $R^1 = R^2 = OCH_3$; $R^3$ =H, $R^4 = CF_3$
5e ; $R^1$ = Cl; $R^2$ = H; $R^3 = OCH_3$, $R^4 = OCH_3$
5f ; $R^1$ = CN; $R^2$ = H; $R^3 = OCH_3$, $R^4 = OCH_3$
5g; $R^1 = SCH_3$; $R^2$ = H; $R^3 = OCH_3$, $R^4 = OCH_3$

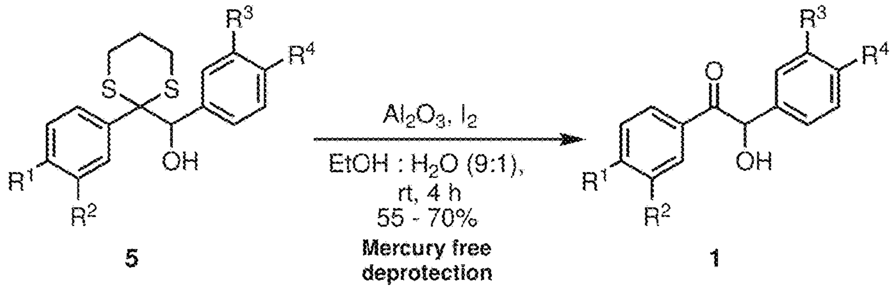

5 1

5a ; $R^1 = R^2 = R^3 = R^4 = OCH_3$
5b ; $R^1 = R^2 = OCH_3$; $R^3 = H$; $R^4 = Cl$
5c ; $R^1 = R^2 = OCH_3$; $R^3 = H$, $R^4 = CN$
5d ; $R^1 = R^2 = OCH_3$; $R^3 = H$, $R^4 = CF_3$
5e ; $R^1 = Cl$; $R^2 = H$; $R^3 = OCH_3$, $R^4 = OCH_3$
5f ; $R^1 = CN$; $R^2 = H$; $R^3 = OCH_3$, $R^4 = OCH_3$
5g; $R^1 = SCH_3$; $R^2 = H$; $R^3 = OCH_3$, $R^4 = OCH_3$

1a ; $R^1 = R^2 = R^3 = R^4 = OCH_3$
1b ; $R^1 = R^2 = OCH_3$; $R^3 = H$; $R^4 = Cl$
1c ; $R^1 = R^2 = OCH_3$; $R^3 = H$, $R^4 = CN$
1d ; $R^1 = R^2 = OCH_3$; $R^3 = H$, $R^4 = CF_3$
1e ; $R^1 = Cl$; $R^2 = H$; $R^3 = OCH_3$, $R^4 = OCH_3$
1f ; $R^1 = CN$; $R^2 = H$; $R^3 = OCH_3$, $R^4 = OCH_3$
1g; $R^1 = SCH_3$; $R^2 = H$; $R^3 = OCH_3$, $R^4 = OCH_3$

FIG. 10

VISIBLE LIGHT ACTIVE BIOMASS DERIVED PHOTOINITIATORS

RELATED APPLICATIONS

This is the national phase application of international application PCT/US2021/032893, filed under the authority of the Patent Cooperation Treaty on May 18, 2021, published; which claims priority to U.S. Provisional Application No. 63/026,970 filed under 35 U.S.C. § 111(b) on May 19, 2020. The entire disclosure of each of the aforementioned applications is incorporated herein by reference in its entirety for all purposes.

STATEMENT REGARDING FEDERALLY SPONSORED RESEARCH

This invention was made with no government support. The government has no rights in this invention.

BACKGROUND

Photoinitiators are widely used for various applications that involves UV curing. These include automobile parts manufacturing, automobile parts, 3D printing, contact lenses, resin curing, silicones, epoxies, dental composites, aircraft parts, and composites. Most conventional photoinitiators require UV light. There is a need in the art for new and improved photoinitiators have features that will be compatible to existing formulations but will have the ability to work under visible light conditions.

SUMMARY

Provided herein is a composition comprising Formula Bz-1:

Formula Bz-1

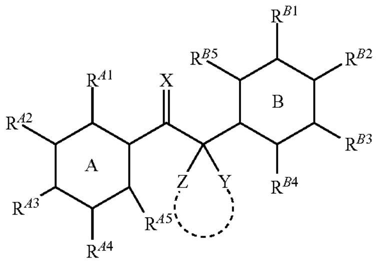

where dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

In certain embodiments, the composition comprises Formula A:

Formula A

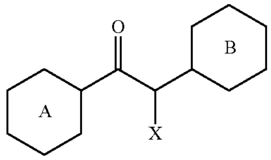

where units A and B represent an alkyl chain, a carbocycle, a heterocyclic moiety, or a combination of C—C or C-heteroatom bonds, optionally substituted with one or more electron withdrawing (e.g., alkoxy) or electron donating substituents (e.g., halogens). X can feature an alkoxy, halo, SH, S-alkyl, carboxy, aryloxy, or hetero-atom attached to a carbocycle or a heterocycle. In certain embodiments, at least one of the units A, B, or X is derived from bio-mass.

In certain embodiments, the composition comprises bis-(dimethoxy)-benzoin 1a:

1a

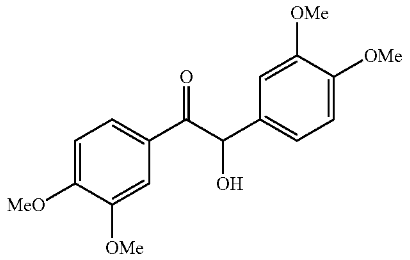

In certain embodiments, the composition comprises para-chlorobenzyl-(dimethoxy)-benzoin 1b:

1b

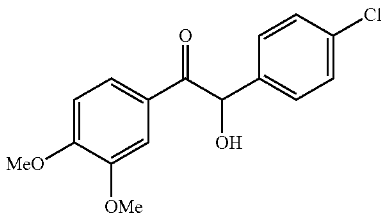

In certain embodiments, the composition comprises para-cyanobenzyl-(dimethoxy)-benzoin 1c:

1c

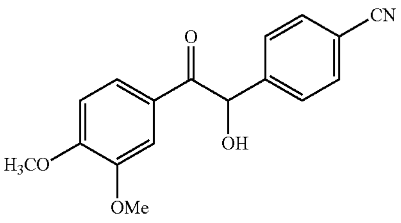

In certain embodiments, the composition comprises para-trifluoromethylbenzyl-(dimethoxy)-benzoin 1d:

1d

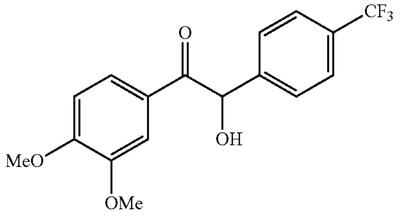

In certain embodiments, the composition comprises para-chlorobenzoyl-(dimethoxy)-benzoin 1e:

1e

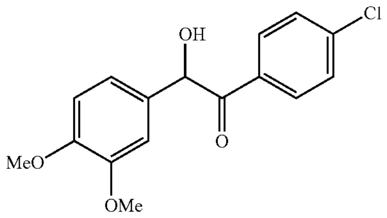

In certain embodiments, the composition comprises para-thiomethylbenzyl-(dimethoxy)-benzoin 1f:

1f

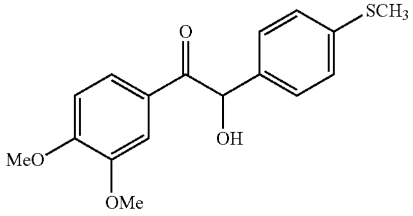

In certain embodiments, the composition comprises para-thiomethylbenzoyl-(dimethoxy)-benzoin 1g:

1g

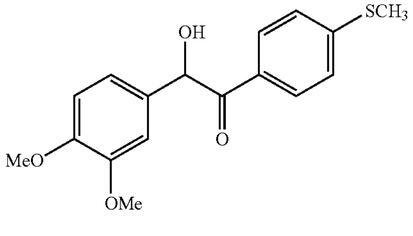

In certain embodiments, the composition comprises compound para-fluorobenzyl-(dimethoxy)-benzoin 1i:

1i

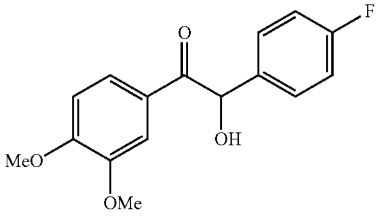

In certain embodiments, the composition comprises compound para-fluorolbenzoyl-(dimethoxy)-benzoin 1j:

1j

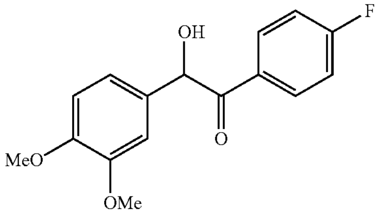

Further provided is a composition comprising Formula Bz-2 or Formula Bz-3:

Formula Bz-2

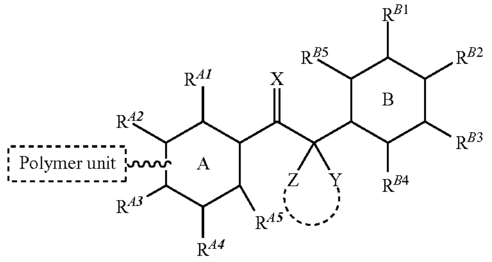

Formula Bz-3

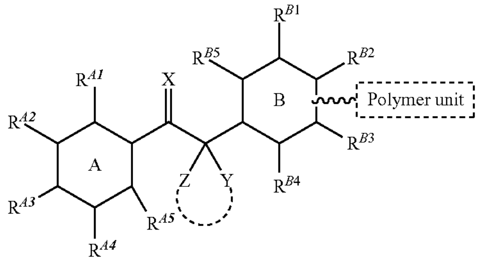

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitrites, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is vinyl, stryl, acryl, or cyclic monomers selected from lactones (cyclic esters), epoxides, lactides, lactams, silicon-containing cyclic monomers, and cyclic carbonates.

In certain embodiments, the composition comprises Bz-2a:

Bz-2a

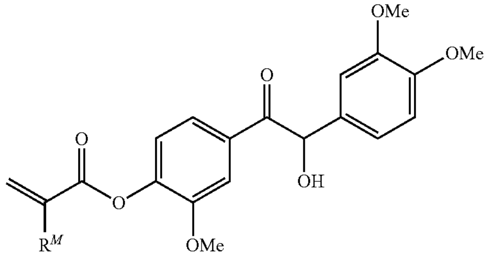

where $R^M$ is alkyl, aryl, or heteroaryl.

In particular embodiments, the composition comprises Bz-2a-I:

Bz-2a-I

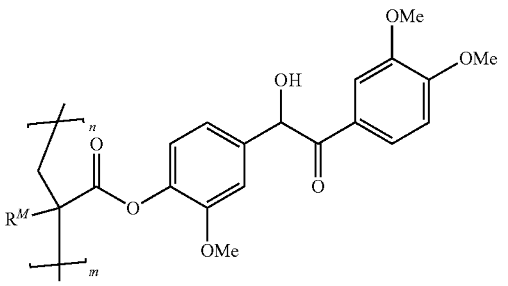

wherein m and n are each integers.

In certain embodiments, the composition comprises compound Bz-2b:

Bz-2b

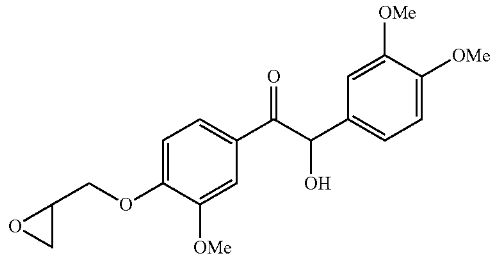

In certain embodiments, the composition comprises Bz-2b-I:

Bz-2b-I

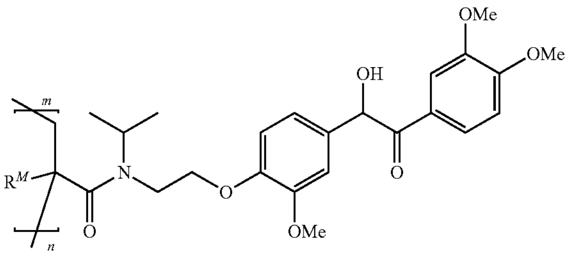

wherein m and n are each integers.

In certain embodiments, the composition comprises compound Bz-2b:

Bz-2c

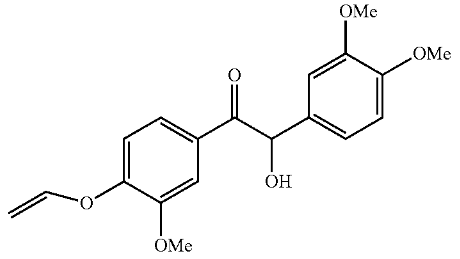

In certain embodiments, the composition comprises compound Bz-2d:

Bz-2d

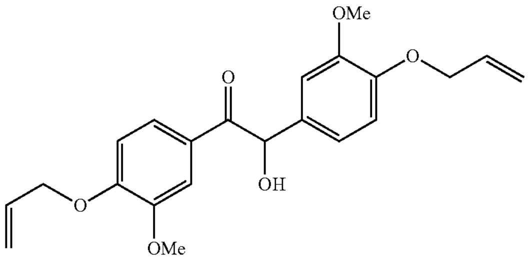

In certain embodiments, the composition comprises Bz-3a:

Bz-3a

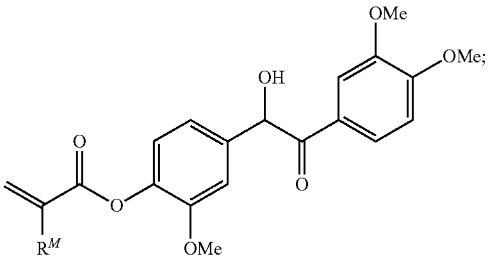

wherein $R^M$ is alkyl, aryl, or heteroaryl.

In particular embodiments, the composition comprises Bz-3a-I:

Bz-3a-I
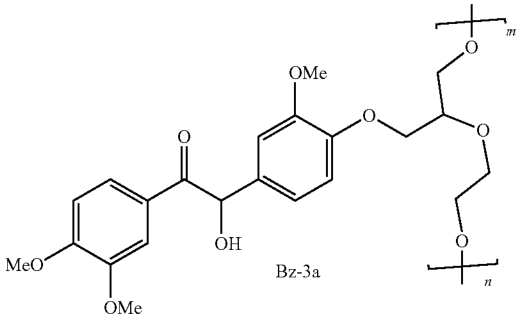
Bz-3a
wherein m and n are each integers.
In certain embodiments, the composition comprises compound Bz-3b:
Bz-3b
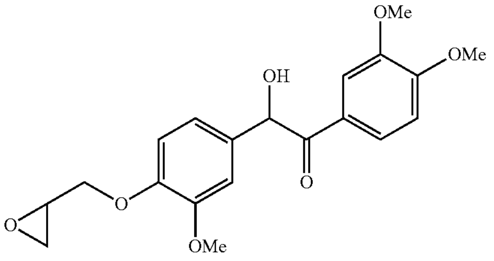
In certain embodiments, the composition comprises compound Bz-3c:
Bz-3c
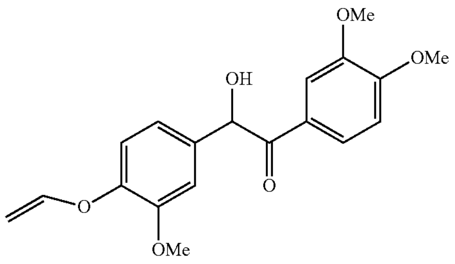
In certain embodiments, the composition comprises compound Bz-3d:
Bz-3d
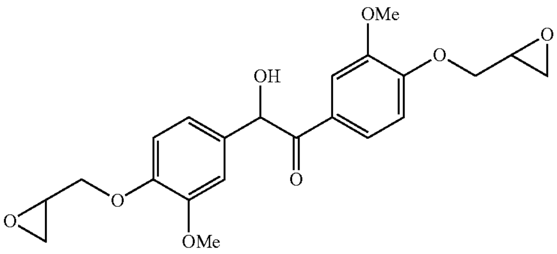
Further provided is a composition comprising Formula Bz-4 or Formula Bz-5:
Formula Bz-4
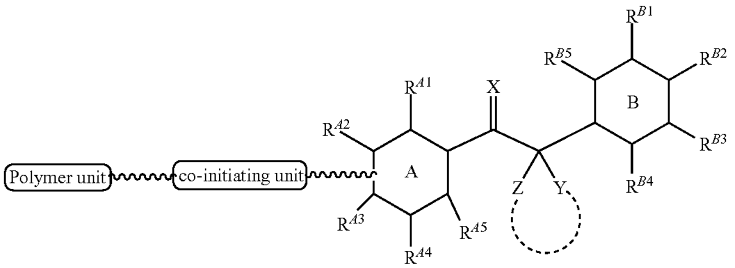
Formula Bz-5
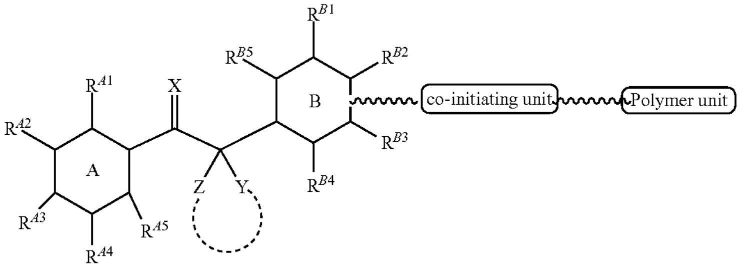

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitrites, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, a thiol, or any hydrogen atom donor; and the polymer unit is vinyl, styryl, acryl, or cyclic monomers selected from lactones (cyclic esters), epoxides, lactides, lactams, silicon-containing cyclic monomers, and cyclic carbonates.

In certain embodiments, the composition comprises compound Bz-4a:

Further provided is a composition comprising Formula Bz-6 or Formula Bz-7:

Formula Bz-6

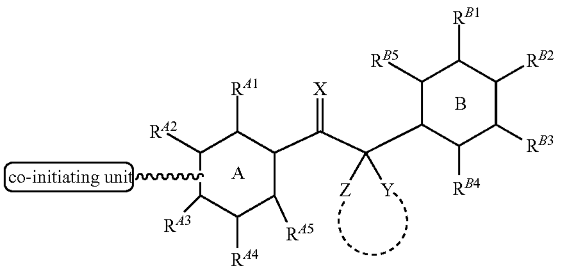

Bz-4a

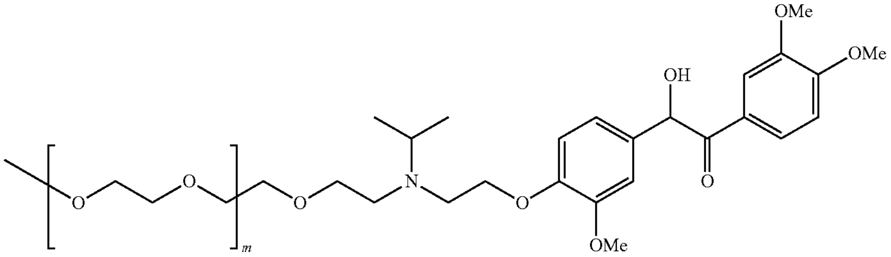

wherein m is an integer.

In certain embodiments, the composition comprises compound Bz-5a:

Bz-5a

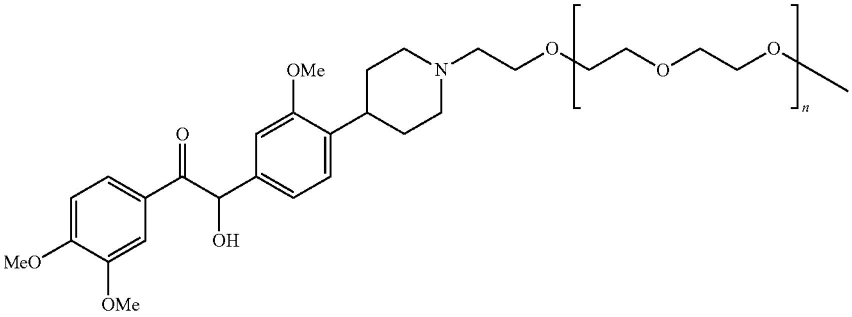

wherein n is an integer.

-continued

Formula Bz-7

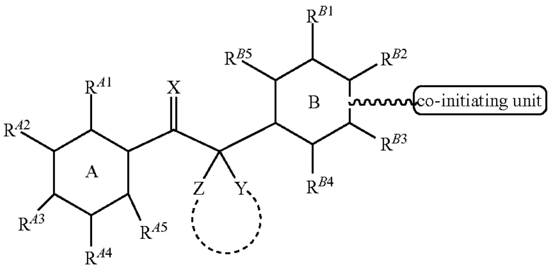

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, a thiol, or any hydrogen atom donor.

In certain embodiments, the composition comprises compound Bz-6a:

Bz-6a

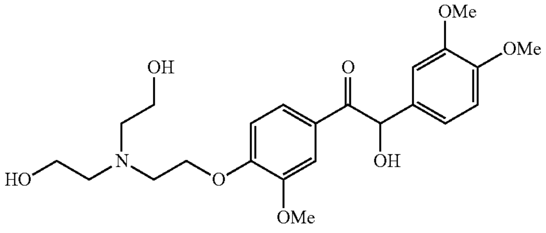

In certain embodiments, the composition comprises compound Bz-6b:

Bz-6b

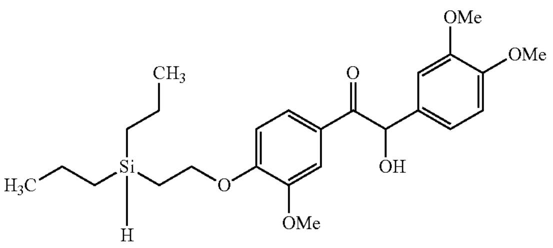

In certain embodiments, the composition comprises compound Bz-6c:

Bz-6a

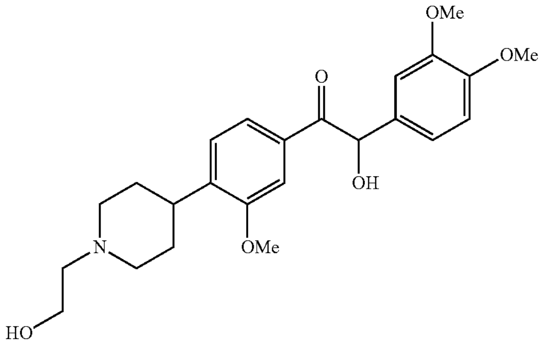

In certain embodiments, the composition comprises compound Bz-6d:

Bz-6d

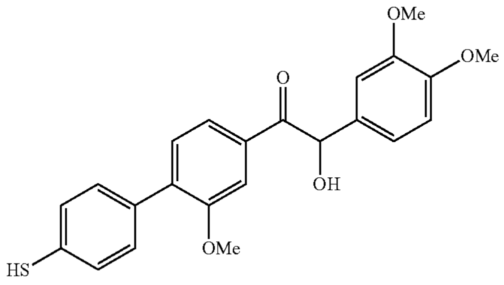

In certain embodiments, the composition comprises compound Bz-7a:

Bz-7a

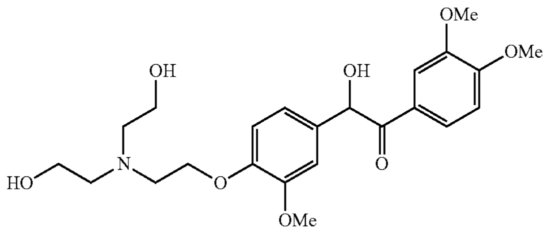

In certain embodiments, the composition comprises compound Bz-7b:

Bz-7

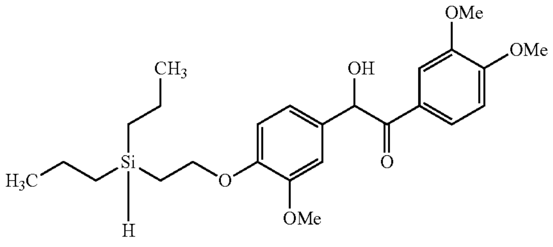

In certain embodiments, the composition comprises compound Bz-7c:

Bz-7c

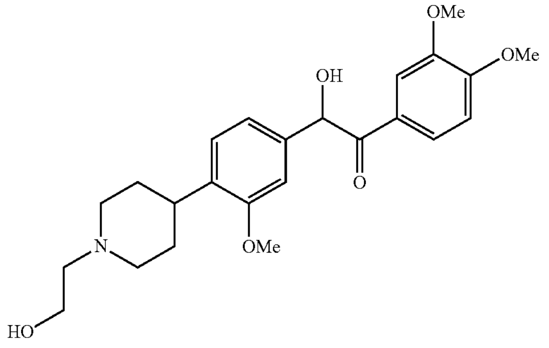

In certain embodiments, the composition comprises compound Bz-7d:

Bz-7d

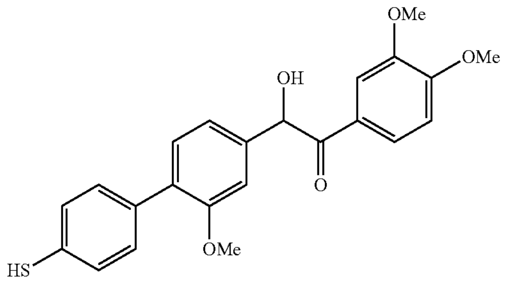

Further provided is a method for making a polymer, the method comprising exposing a photoinitiator and a monomer to light to produce a polymer, wherein the photoinitiator is a biomass derived benzoin derivative. In certain embodiments, the polymer is colorless or transparent.

In certain embodiments, the photoinitiator comprises Formula Bz-1:

Formula Bz-1

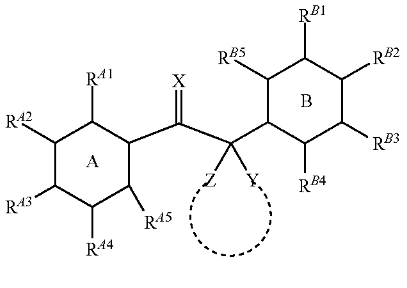

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

In certain embodiments, the photoinitiator comprises Formula A:

Formula A

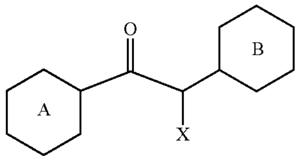

where units A and B represent an alkyl chain, a carbocycle, a heterocyclic moiety, or a combination of C—C or C-heteroatom bonds, optionally substituted with one or more electron withdrawing (e.g., alkoxy) or electron donating substituents (e.g., halogens). X can feature an alkoxy, halo, SH, S-alkyl, carboxy, aryloxy, or hetero-atom attached to a carbocycle or a heterocycle.

In certain embodiments, the photoinitiator comprises bis-(dimethoxy)-benzoin 1a:

1a

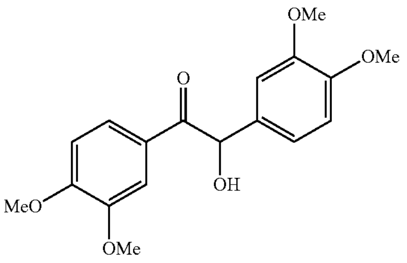

In certain embodiments, the photoinitiator comprises para-chlorobenzyl-(dimethoxy)-benzoin 1b:

1b

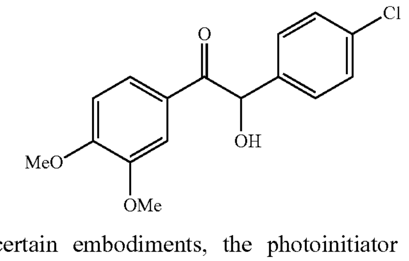

In certain embodiments, the photoinitiator comprises para-cyanobenzyl-(dimethoxy)-benzoin 1c:

1c

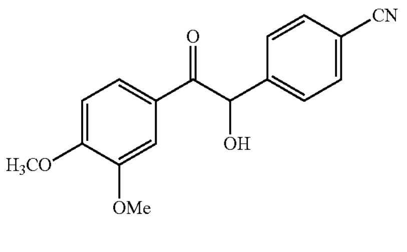

In certain embodiments, the photoinitiator comprises para-trifluoromethylbenzyl-(dimethoxy)-benzoin 1d:

1d

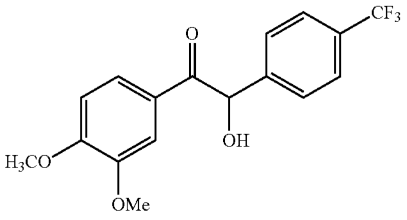

In certain embodiments, the photoinitiator comprises para-chlorobenzoyl-(dimethoxy)-benzoin 1e:

1e

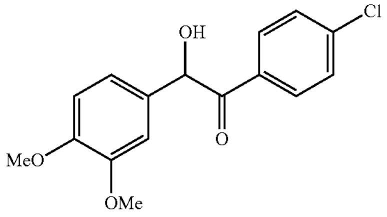

In certain embodiments, the photoinitiator comprises para-thiomethylbenzyl-(dimethoxy)-benzoin 1f:

1f

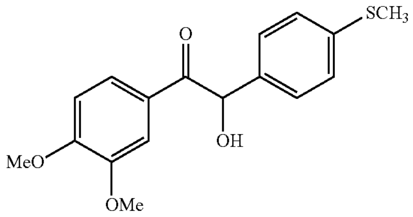

In certain embodiments, the photoinitiator comprises para-thiomethylbenzoyl-(dimethoxy)-benzoin 1g:

1g

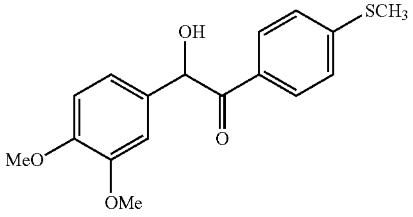

In certain embodiments, the photoinitiator comprises compound para-fluorobenzyl-(dimethoxy)-benzoin 1i:

1i

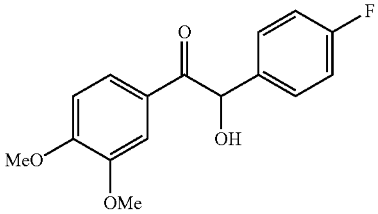

In certain embodiments, the photoinitiator comprises compound para-fluorobenzoyl-(dimethoxy)-benzoin 1j:

1j

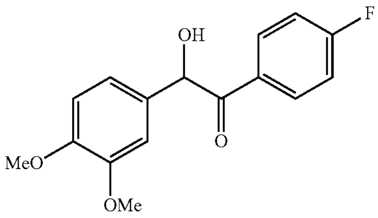

In certain embodiments, the photoinitiator comprises Formula Bz-2 or Formula Bz-3:

Formula Bz-2

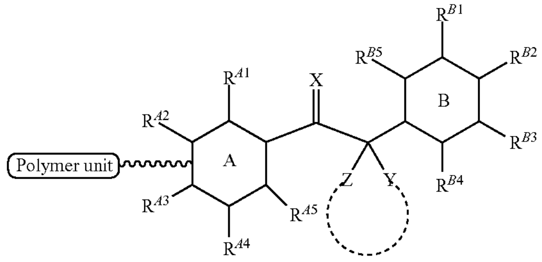

Formula Bz-3

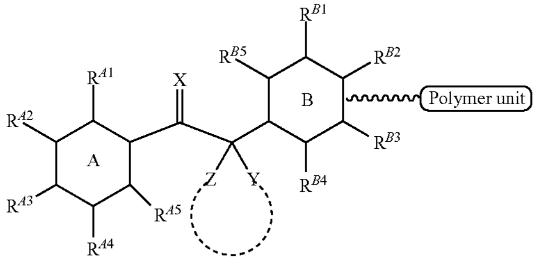

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is vinyl, stryl, acryl, or cyclic monomers selected from lactones (cyclic esters), epoxides, lactides, lactams, silicon-containing cyclic monomers, and cyclic carbonates.

In certain embodiments, the photoinitiator comprises Bz-2a:

Bz-2a

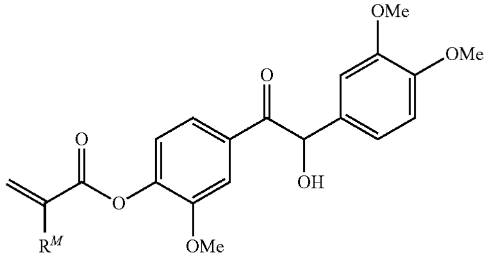

where $R^M$ is alkyl, aryl, or heteroaryl.

In certain embodiments, the photoinitiator comprises Bz-2a-I:

Bz-2a-1

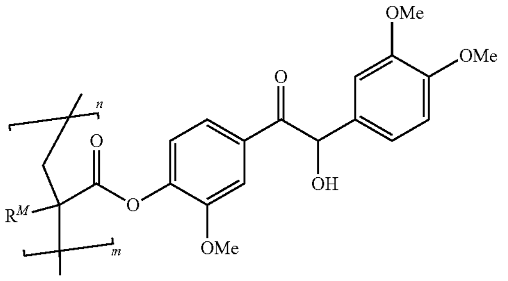

wherein m is an integer.

In certain embodiments, the photoinitiator comprises compound Bz-2b:

Bz-2b

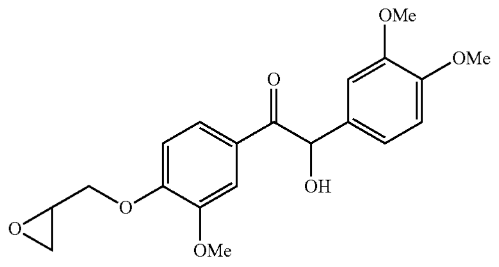

In certain embodiments, the photoinitiator comprises Bz-2b-I:

Bz-2b-I

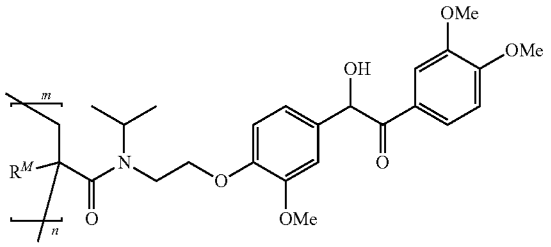

wherein m and n are each integers.

In certain embodiments, the photoinitiator comprises compound Bz-2c:

Bz-2c

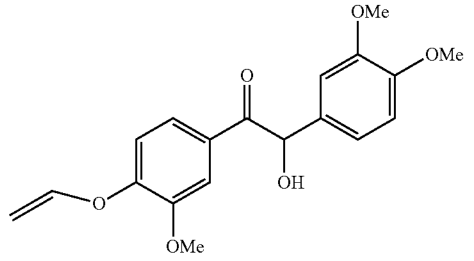

In certain embodiments, the photoinitiator comprises compound Bz-2d:

Bz-2d

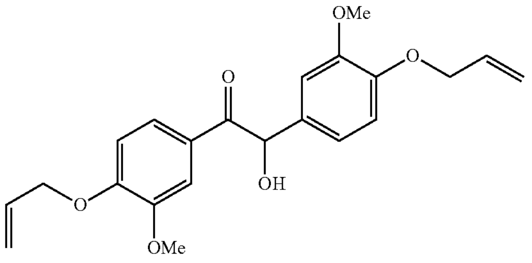

In certain embodiments, the photoinitiator comprises Bz-3a:

Bz-3a

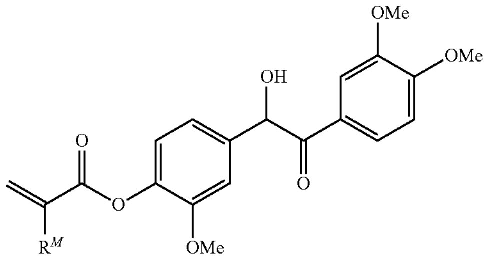

wherein $R^M$ is alkyl, aryl, or heteroaryl.

In particular embodiments, the photoinitiator comprises Bz-3a-I:

Bz-3a-I
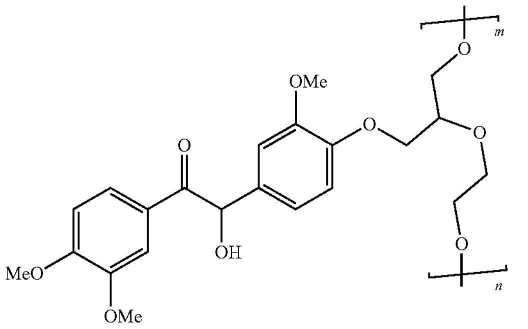
Bz-3a
wherein m and n are each integers.
In certain embodiments, the photoinitiator comprises compound Bz-3b:
Bz-3b
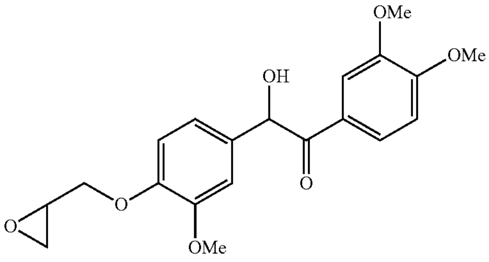
In certain embodiments, the photoinitiator comprises compound Bz-3c:
Bz-3c
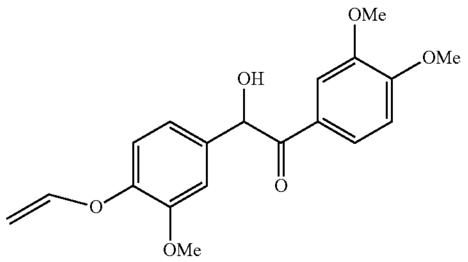
In certain embodiments, the photoinitiator comprises compound Bz-3d:
Bz-3d
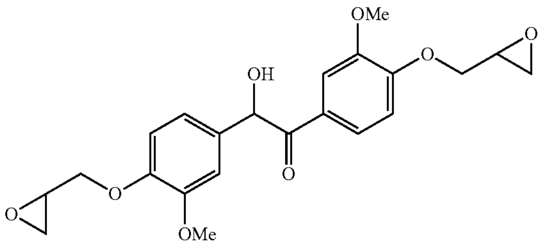
In certain embodiments, the photoinitiator comprises Formula Bz-4 or Formula Bz-5:
Formula Bz-4
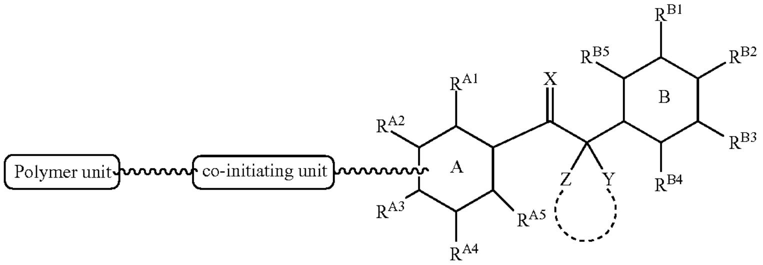
Formula Bz-5
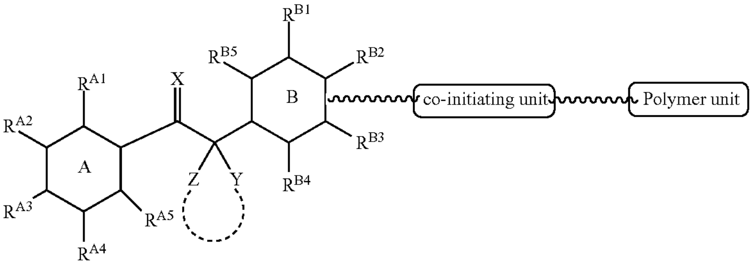

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, a thiol, or any hydrogen atom donor; and the polymer unit is vinyl, stryl, acryl, or cyclic monomers selected from lactones (cyclic esters), epoxides, lactides, lactams, silicon-containing cyclic monomers, and cyclic carbonates.

In certain embodiments, the photoinitiator comprises compound Bz-4a:

Bz-4a

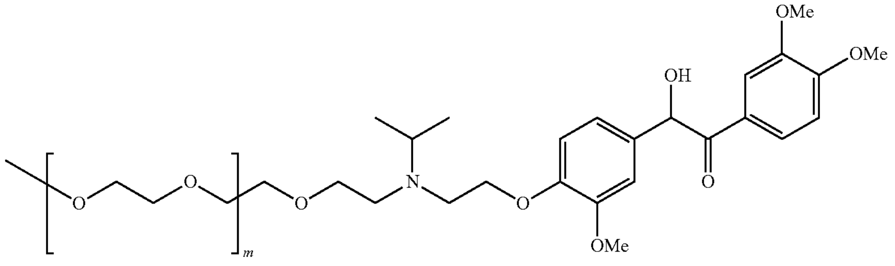

wherein m is an integer.

In certain embodiments, the photoinitiator comprises compound Bz-5a:

Bz-5a

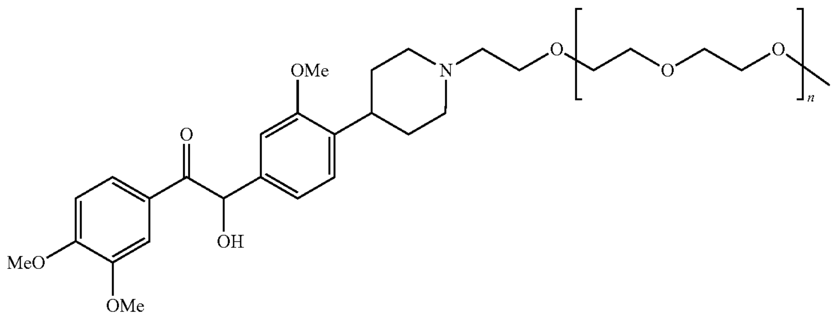

wherein n is an integer.

In certain embodiments, the photoinitiator comprises Formula Bz-6 or Formula Bz-7:

Formula Bz-6

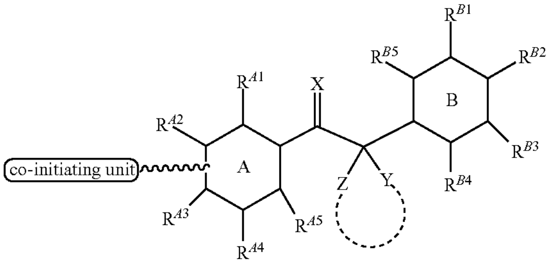

-continued

Formula Bz-7

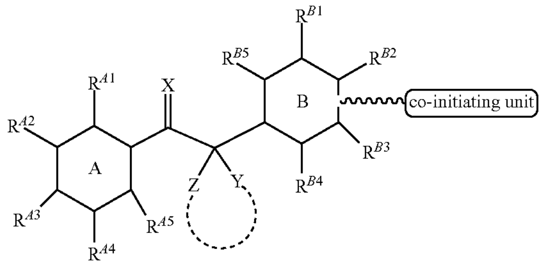

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitrites, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, a thiol, or any hydrogen atom donor.

In certain embodiments, the photoinitiator comprises compound Bz-6a:

Bz-6a

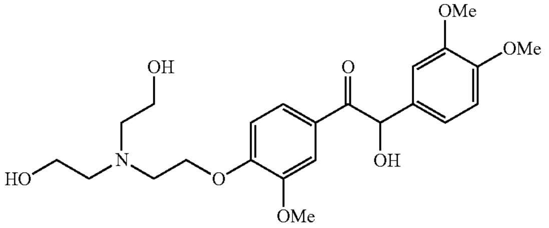

In certain embodiments, the photoinitiator comprises compound Bz-6b:

Bz-6b

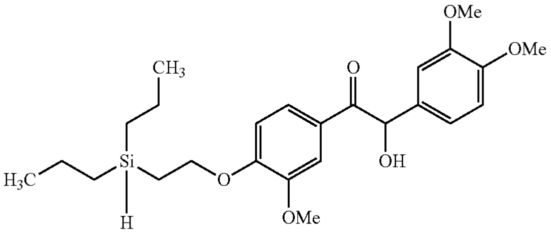

In certain embodiments, the photoinitiator comprises compound Bz-6c:

Bz-6a

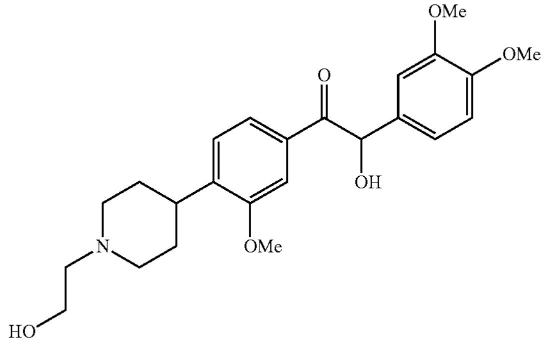

In certain embodiments, the photoinitiator comprises compound Bz-6d:

Bz-6d

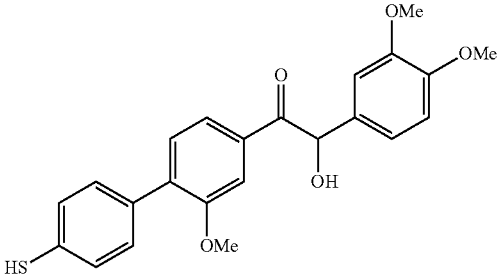

In certain embodiments, the photoinitiator comprises compound Bz-7a:

Bz-7a

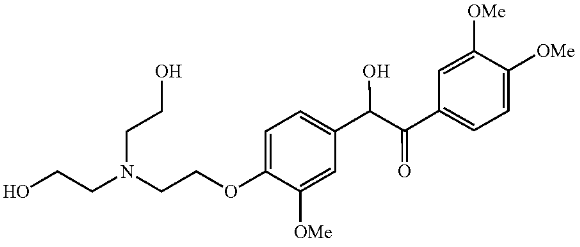

In certain embodiments, the photoinitiator comprises compound Bz-7b:

Bz-7

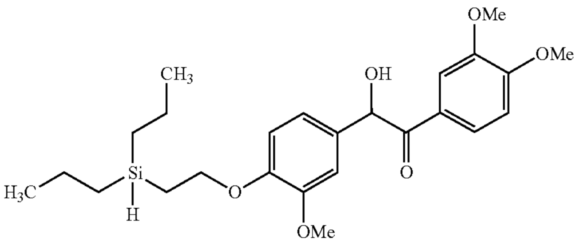

In certain embodiments, the photoinitiator comprises compound Bz-7c:

Bz-7c

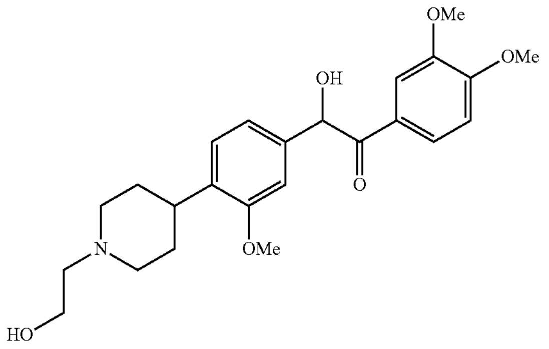

In certain embodiments, the photoinitiator comprises compound Bz-7d:

Bz-7d

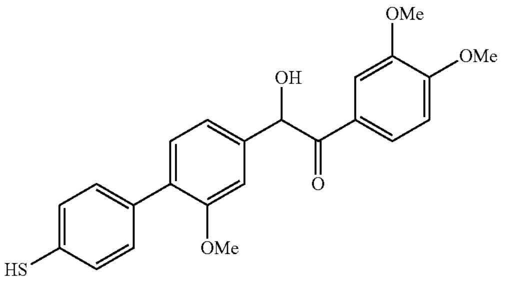

In certain embodiments, the photoinitiator is prepared from biomass. In certain embodiments, the light is visible light. In certain embodiments, the light is purple light. In certain embodiments, the light is blue light. In certain embodiments, the light is green light.

In certain embodiments, the monomer is methylmethacrylate 6:

6

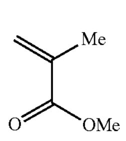

In particular embodiments, the polymer is polymer 7:

7

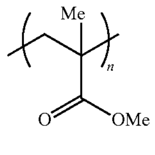

where n is an integer.

In certain embodiments, no co-initiator is needed and just the photoinitiator is sufficient to effect polymerization in the presence of light (called type I conditions). In certain embodiments, a co-initiator is exposed to the light along with the photoinitiator and the monomer (called the type II conditions). In particular embodiments, the co-initiator comprises triethanol amine.

In certain embodiments, the light is a 50 $mW/cm^2$ light.

In certain embodiments, the polymer is used to make a dental composite or to prepare a bone substitute material or automobile parts or aerospace parts.

Further provided is a kit for making a polymer, the kit comprising a first container housing a monomer, and a second container housing biomass derived benzoin or biomass derived benzoin and triethanol amine derivative.

Further provided is a photoinitiator comprising a biomass derived benzoin derivative capable of initiating a polymerization of a monomer into a transparent polymer upon exposure to visible light.

Further provided is the use of biomass derived benzoin derivative as a photoinitiator.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A: UV-Vis absorption spectra of photoinitiators 1a-1b with concentration of 5 mM in MeCN. FIG. 4B UV-Vis spectra of photoinitiators recorded for 1a-1g with same optical density (~0.2) at ~390 nm.

FIG. 7: Chemical structures of benzoin photoinitiators, monomers, and corresponding polymers.

FIG. 10: Scheme 7: Synthesis of benzoin derivatives 1a-1g.

FIG. 14A-14B: $^1H$ NMR spectrum (FIG. 14A) and $^{13}C$ NMR spectrum (FIG. 14B) of dithiane protected dimethoxybenzaldehyde 3a.

FIG. 18A-18B: $^{1}H$ NMR spectrum (FIG. 18A) and $^{13}C$ NMR spectrum (FIG. 18B) of dimethoxy derived benzyl alcohol 5a.

FIG. 25A-25B: $^{1}H$ NMR spectrum (FIG. 25A) and $^{13}C$ NMR spectrum (FIG. 25B) of bis-(dimethoxy)-phenylbenzoin 1a.

DETAILED DESCRIPTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The impact of smart materials in day-to-day life keeps expanding due to their enhanced performance, versatility, and practicality. Most often these fossil materials rely on fossil fuels to enhance and sustain their unique features. This reliance on fossil fuels for developing modern materials has initiated the need to look for alternative sources for sustaining development with minimal environmental impact. A key aspect to enable industries to move towards sustainable solutions is to develop systems that have similar or enhanced functionalities but are environmentally benign. In addition, the new systems should be able to substitute the existing industrial processes without causing huge economic burden for the switch from fossil fuel derived methodology to a greener process.

Figure 1:
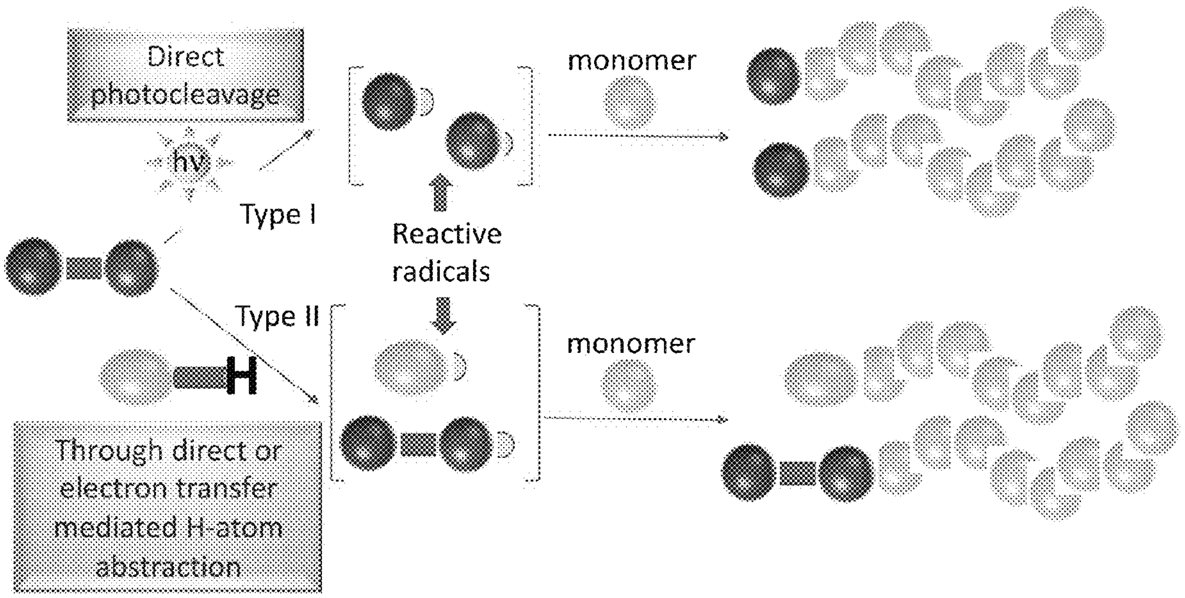
FIG. 1: Type I and Type II photo-initiating system for polymerization.

Bio-mass derived photo-initiators have been developed, as their relevance is accentuated due their widespread use in various industrial processes such as polymerization, photo-curing, and development of various smart materials. There exists a number of industrially employed photo-initiators, such as benzoin ethers, acyl phosphines thioxanthones, and benzophenones, to simply name a few. Light activation of photo-initiators can be broadly classified as type I or type II process leading to reactive radicals that initiates the polymerization of the monomers (FIG. 1). Type I photochemistry depends on direct bond cleavage (e.g., α-cleavage). On the other hand, type II photochemistry involves the generation of radicals either through atom abstraction (typically hydrogen atom) or through electron transfer initiated proton transfer (i.e., net hydrogen atom transfer). To make use of the functionalities provided by nature and tailor them to respond to light, it is necessary to modify the system so that an appropriate chromophore is accessed, and to fine-tune its photochemical and photophysical properties. The present disclosure provides bio-based derived benzoin type photo-initiators that can be tailored for both Type I and Type II photo-polymerization processes.

In general, the photoinitiators described herein have Formula Bz-1:

Formula Bz-1

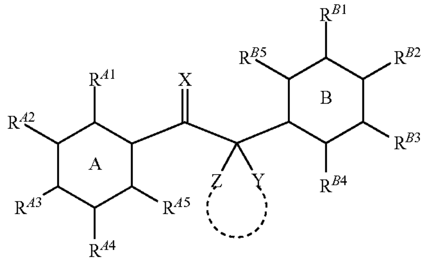

where dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes. In some cases, the photoinitiators have Formula A:

Formula A

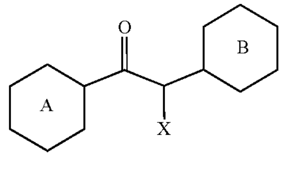

where units A and B represent an alkyl chain, a carbocycle, a heterocyclic moiety, or a combination of C—C or C-heteroatom bonds, optionally substituted with one or more electron withdrawing (e.g., alkoxy) or electron donating substituents (e.g., halogens). X can feature an alkoxy, halo, SH, S-alkyl, carboxy, aryloxy, or hereo-atom attached to a carbocycle or a heterocycle. In some examples, at least one of the units A, B, or X is derived from bio-mass. Non-limiting examples of photoinitiators having Formula A are compounds 1a-1g (FIG. 2) and 1i, 1j.

The photoinitiators herein may also include a polymer unit, such as Formula Bz-2 or Formula Bz-3:

Formula Bz-2

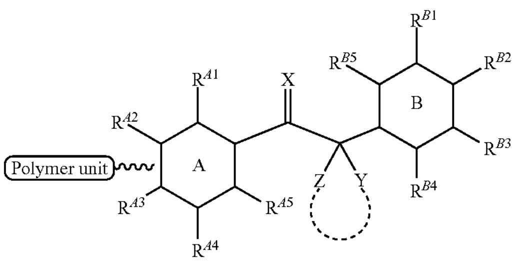

Formula Bz-3

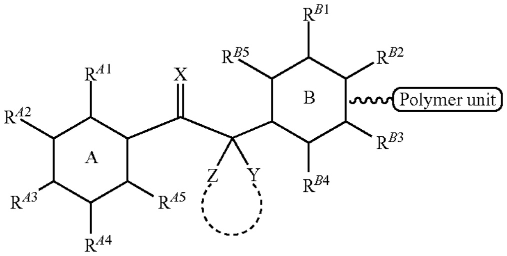

where dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is vinyl, stryl, acryl, or cyclic monomers such as lactones (cyclic esters), epoxides, lactides, lactams, silicon-containing cyclic monomers, cyclic carbonates, or others. Non-limiting examples of such photoinitiators include Bz-2a, Bz-2b, Bz-2c, Bz-2d, Bz-3a, Bz-3b, Bz-3c, and Bz-3d.

Furthermore, the photoinitiators herein may also include a co-initiating unit, such as in Formula Bz-6 or Formula Bz-7:

Formula Bz-6

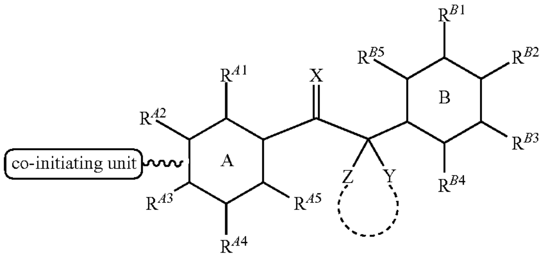

Formula Bz-7

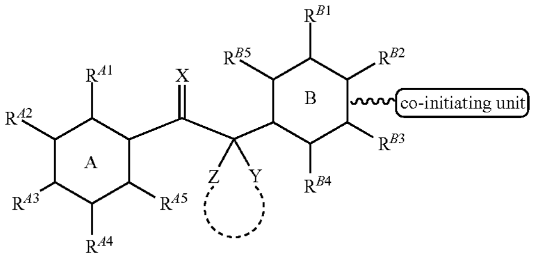

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitrites, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, a thiol, or any hydrogen atom donor. Non-limiting examples of such photoinitiators include Bz-6a, Bz-6b, Bz-6c, Bz-6d, Bz-7a, Bz-7b, Bz-7c, and Bz-7d.

Additionally, the photoinitiators herein may include both a co-initiating unit and a polymer unit, such as in Formula Bz-4 or Formula Bz-5:

Formula Bz-4

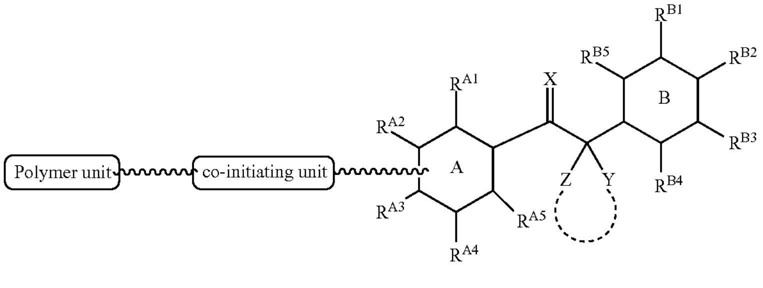

-continued

Formula Bz-5

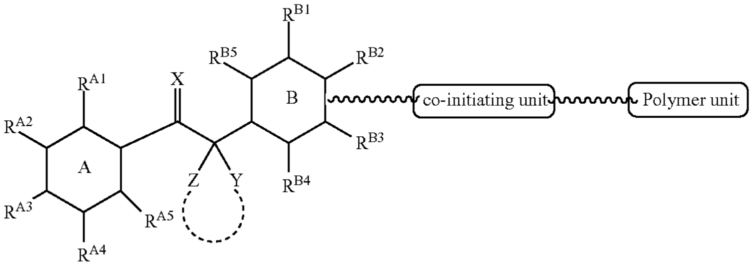

wherein dashed lines indicate optional bonds; X=O, S, NH, Ge, NC(O)—O—$R^C$, N—O—C(O)$R^C$, or NO—$R^C$, wherein $R^C$ is alkyl, aryl, or heteroaryl; A or B is a ring derived from biomass; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, a thiol, or any hydrogen atom donor; and the polymer unit is vinyl, stryl, acryl, or cyclic monomers like lactones (cyclic esters) epoxides, lactides, lactams, silicon-containing cyclic monomers, cyclic carbonates, or others. Non-limiting examples of such photoinitiators include Bz-4a and Bz-5a.

Benzoin type chromophores are well known to undergo α-cleavage typically featuring an nπ* excited state (typical irradiation wavelength 330-250 nm). This industrially relevant chromophore was tailored from biomass to enable photopolymerization under visible light illumination. In line with the principles of green chemistry, benzoin photoinitiators 1a-1g were synthesized (Scheme 1) from veratraldehyde 2a, a feedstock chemical derived from lignin. To accomplish the synthesis, the aldehyde functionality was protected with 1,3-propane dithiol in the presence of iodine to yield dithiane protected aldehyde derivative 3. Treatment of dithiane with alkyl lithium generated the corresponding carbanion and the subsequent nucleophilic addition to the benzaldehyde derivatives 4 yielded benzyl alcohol 5 with isolated yields ranging from ~55-70%. The deprotection of the dithiane from 5 was performed through a mercury free deprotection strategy involving iodine/alumina in ethanol-water (9:1) as solvent at room temperature to access the desired benzoin photoinitiators 1a-1g. Based on the developed synthetic protocol, two distinct sets of photo-initiators were developed, as different excited state features were anticipated. In the first set of photo-initiators 1a-1d, the benzoyl functionality features dimethoxy substituents in both the meta- and para-positions. In the second set of photo-initiators 1e-1g, the position of the carbonyl and hydroxyl groups were exchanged when compared to 1a-1d.

Figure 2:
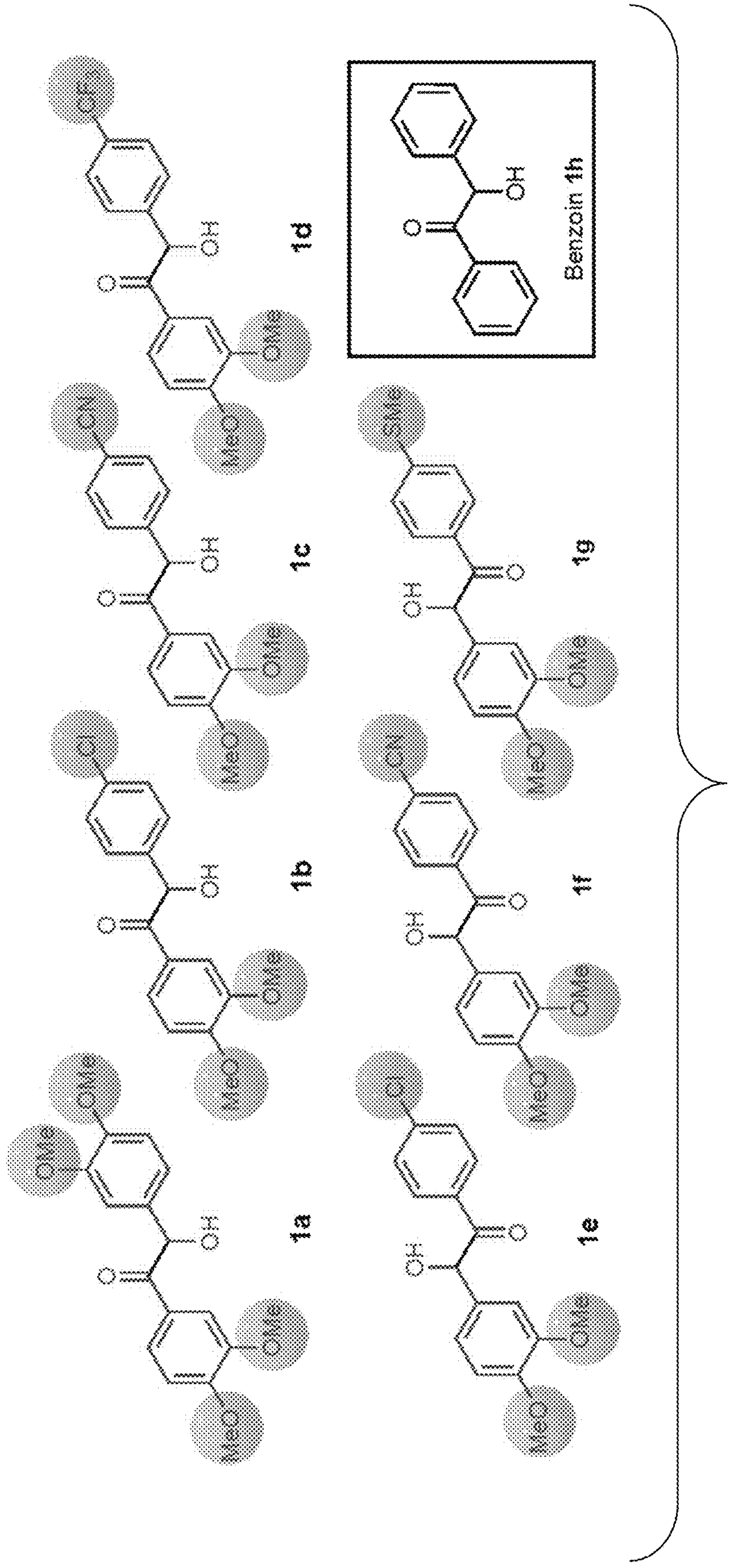
FIG. 2: Scheme 1: Visible light active benzoin photoinitiators derived from biomass.
Figure 3:
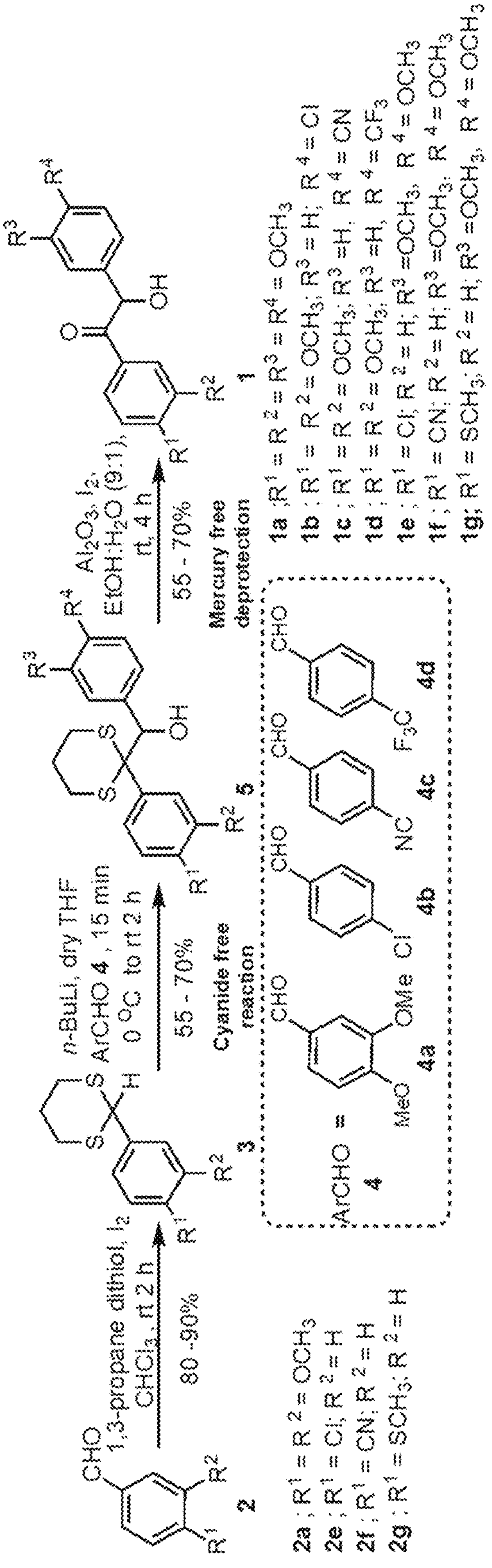
FIG. 3: Scheme 2: Synthesis of visible light active benzoin photo-initiators derived from biomass.
Figure 4A:
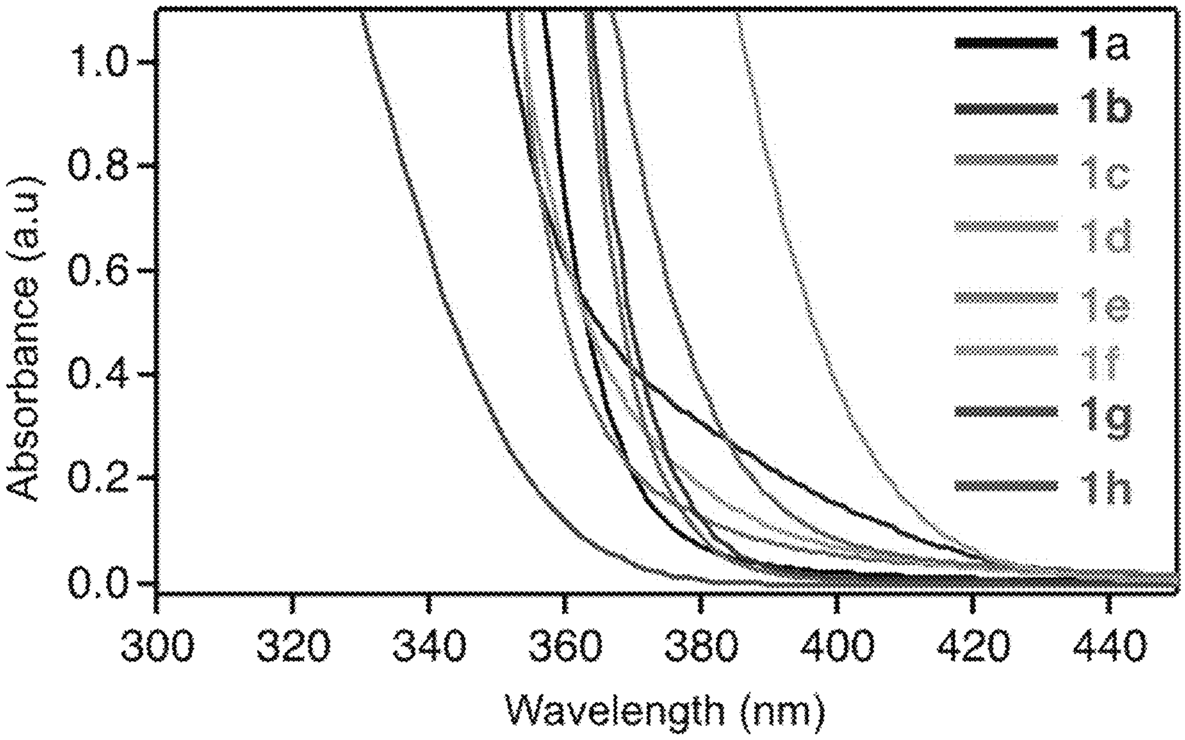
FIG. 4A-4B.
Figure 4B:
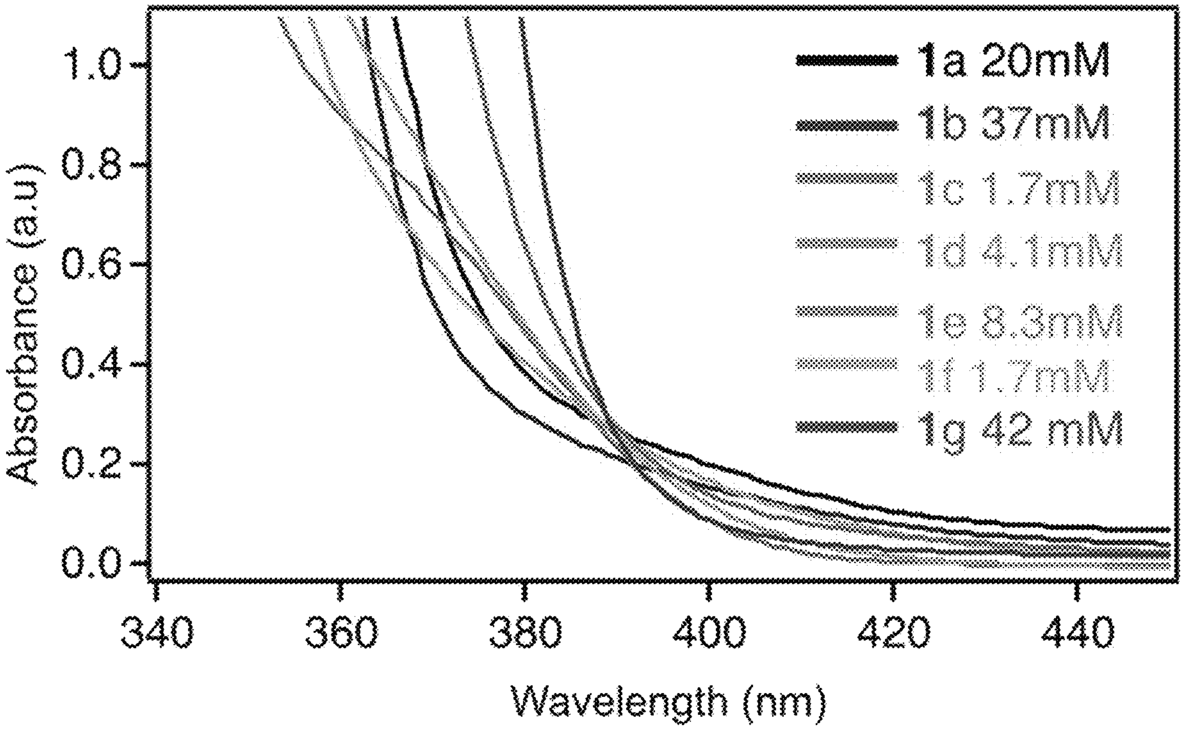
Figure 5:
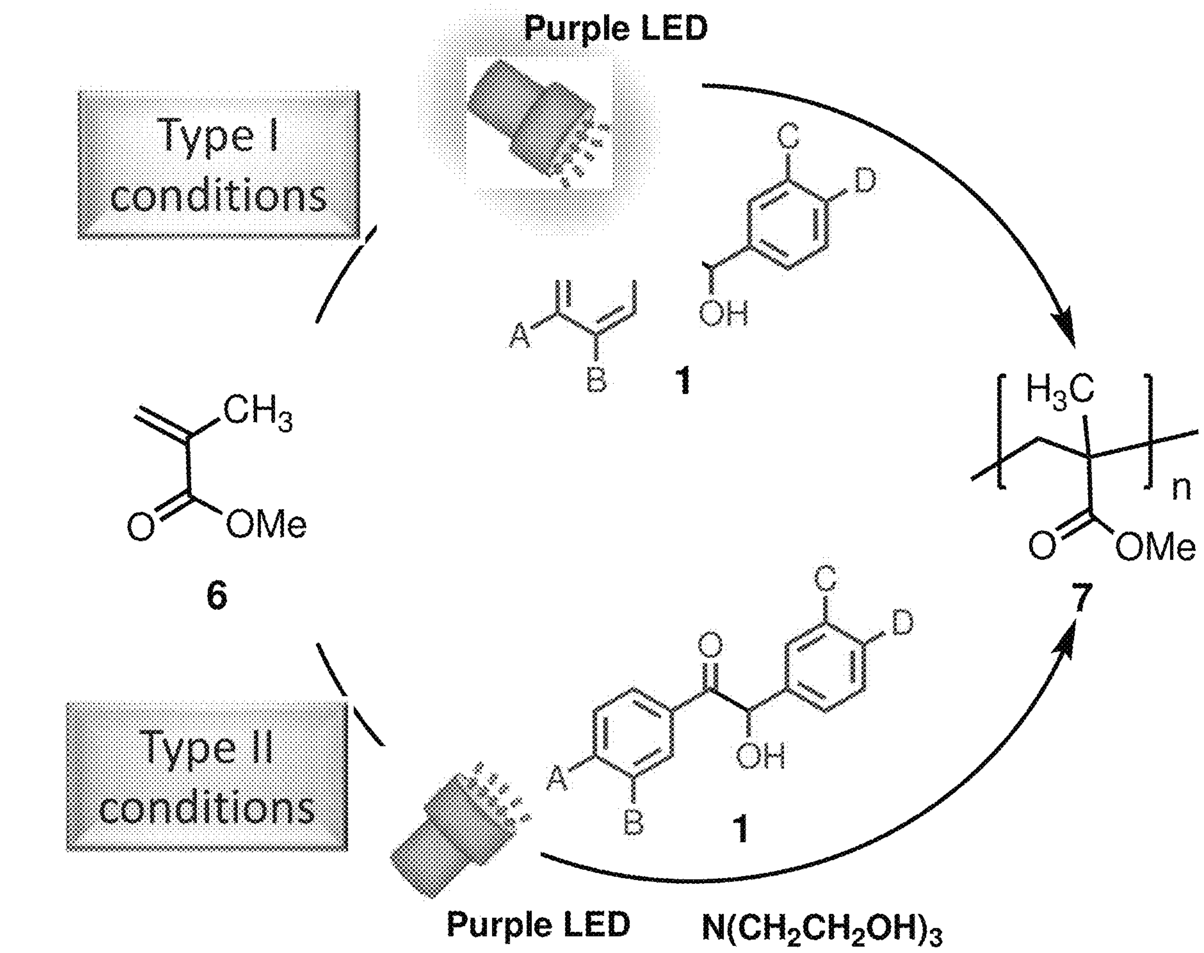
FIG. 5: Scheme 3: Photopolymerization with visible light through Type I and Type II methods.

The investigation began by evaluating the UV-Vis absorbance of all the biomass derived benzoin photoinitiators 1a-1g. The absorptivity of the synthesized bio-mass derived photoinitiators was compared with industrially used benzoin 1b (FIG. 2). Inspection of the UV-Vis spectra of biomass derived photoinitiators 1a-1g at a concentration 5 mM in MeCN showed an onset of absorption varying from ~380 nm (for 1c) to ~425 nm (for 1f). This was in stark contrast to benzoin 1b as its onset was around 370 nm at the same concentration. This clearly showed that the new set of photoinitiators are amenable to visible light irradiation.

The photopolymerization efficiency of the benzoin photoinitiators was evaluated using methylmethacrylate 6 as the model system (Scheme 3). The molecular weight distributions of the resultant poly(methyl methacrylate) PMMA 7 was ascertained by gel permeation chromatography (GPC). In order to investigate free-radical polymerization of methylmethacrylate (3.1 M), benzoin photoinitiators 1a-1g were evaluated by employing them at a low concentration of 5 mM (i.e., $6\times10^{-4}$ mol % of the photoinitiator). As the performance of photoinitiators depends on the concentration, it became critical to evaluate the efficiency of all the photoinitiators with identical constant optical density. To achieve this, UV-Vis studies were performed (FIG. 2B), and the photoinitiators concentrations were fine-tuned such that they have the same optical density at irradiation wavelength (~390 nm). Inspection of FIG. 2B shows that the nature of substituents on the benzoin photoinitiator has a significant effect on the optical density (OD) at ~390 nm and this necessitated employing different concentrations to achieve an OD of ~0.2.

The initial screening of methylmethacrylate polymerization began without any co-initiators (Table-1) by employing photoinitiator 1a that was derived from simple veratraldehyde derivative, which gave the methacrylate polymer 7 at ~6% conversion (Table 1, entry 1). A conversion of ~3% was observed when chloro-derivative 1b (Table 1, entry 2) was employed as a photoinitiator. Benzoins 1a-1d, featuring substitution at the benzyl functionality, gave less monomer conversions, while Benzoins 1e-1g, featuring substitution at the benzoyl functionality, gave higher conversions. For example, chloro-substitution at the para-position of the benzyl functionality (benzoin 1b) resulted in ~3% of polymer conversion, while the corresponding para-chloro-substituted benzoin 1e gave 35% conversion (Table 1, compare entries 2 and 5). Similarly, cyano-substitution at the para-position of the benzyl functionality (benzoin 1c) resulted in inefficient polymerization and the polymer formed was hard to isolate while the corresponding para-cyano-substituted benzoin 1f gave 20% conversion (Table 1, compare entries 3 and 6). The thio-methyl substituted benzoin 1g (Table 1, entry 7) was found to be the efficient photoinitiator with a conversion of 37% in the absence of a typical co-initiator.

TABLE 1

Biomass derived photoinitiators for methacrylateacrylate polymerization without co-initiator

| Entry | PI | PI Concentration | % Conversion [b] | Mn | Mw | PDI |
|---|---|---|---|---|---|---|
| 1 | 1a | 20 mM | 5.8 | 73,903 | 1,32,461 | 1.8 |
| 2 | 1b | 37 mM | 2.9 | 65,795 | 1,42,369 | 2.1 |
| 3[c] | 1c | 1.7 mM | — | — | — | — |
| 4 | 1d | 4.1 mM | 2.2 | 1,11,361 | 2,70,814 | 2.4 |
| 5 | 1e | 8.3 mM | 35 | 45,771 | 84,639 | 1.8 |
| 6 | 1f | 1.7 mM | 20 | 65,281 | 1,16,302 | 1.7 |
| 7 | 1g | 42 mM | 37 | 32,103 | 72,554 | 2.2 |

[a]M = Monomer; PI = Photoinitiator. PI concentrations were prepared to have optical density of ~0.2 at 390 nm. [Monomer] = 3.12 M. Solvent = MeCN. Photopolymerization were carried out with a purple LED strip (wrapped around a pyrex jar) illumination with a flux density of 1.5 mW/cm$^2$. Ee = Flux density (mW/cm$^2$) measured by Newport/spectra physics 407A Portable Laser Power Meter by keeping the sample at a distance of ~2 cm from the light source. Irradiation was performed for 4 h.

[b] % conversion carry an error of 5% (average of three runs) and are determined gravimetrically by taking into account of isolated polymers 7. The values reported are an average of three runs.

[c]Turbid solution was formed on addition of cold methanol indicating less polymerization.

(Note:
Benzoin 1h is insoluble in MeCN while adjusting the OD of ~0.2 at ~390 nm.)

To compare the efficiency of benzoin photoinitiators efficiency in the Type I and Type II process (Schemes 3 and 4), photopolymerization of methylmethacrylate 6 was performed in the presence of co-initiator (Scheme 3). Unsubstituted benzoins undergo α-cleavage from short lived triplet excited states. It was believed that substituted benzoins might have longer lived triplet excited states that can react with the amine co-initiators producing a amino radicals (Scheme 4). A commonly used type II amine co-initiator, triethanolamine, was employed at a concentration equal to the concentration of the benzoin photoinitiator (~1.7 mM), and photopolymerization was performed at ~390 nm for 4 h at room temperature. As seen from Table 2, the results were in accordance with the type-II mechanism for photopolymerization of acrylates in the presence of triethanolamine co-initiator. Taking into consideration of photoinitiator concentration (~1.7 mM) and its molar extinction coefficient ε ($M^{-1}$ $cm^{-1}$), 1c that features a cyano-substituent on the para-benzyl functionality (Table 2, entry 3) and 1f that features a cyano-substituent on the para-benzoyl functionality (Table 2, entry 6) gave 14% and 45% conversions, respectively. This clearly showcased that the electron withdrawing substituents on the benzoyl part of the benzoic photoinitiator is more effective towards methylmethacrylate polymerization than substitution on the benzyl functionality. The chloro-substituted derivatives 1b and 1e (Table 2, entries 2 and 5) gave high polymer formation with isolated yields (by gravimetric analysis) of 56% and 64%, respectively. A ~27% monomer conversion was achieved with trifluromethyl derivative 1d, whereas methoxy-substituted benzoin 1a (Table 1, entry 1) gave ~37%. Inspection of Table 2 reveals that 1g with thio-methyl substitution at the benzoyl functionality gave a conversion of 85%, placing that as the best photoinitiator under the evaluated conditions (Table 2, entry 7).

TABLE 2

Biomass derived photoinitiators for acrylate polymerization at same optical density[a] and in the presence of co-initiator using purple LED

| Entry | PI | [PI] | ε ($M^{-1}$ $cm^{-1}$) | % Conversion [b] | Mw | Mn | PDI |
|---|---|---|---|---|---|---|---|
| 1 | 1a | 20 mM | 10.0 | 37 | 1,58,015 | 74,787 | 2.1 |
| 2 | 1b | 37 mM | 5.40 | 56 | 85,268 | 37,143 | 2.3 |
| 3 | 1c | 1.7 mM | 200 | 14 | 3,76,813 | 1,64,001 | 2.3 |
| 4 | 1d | 4.1 mM | 50.0 | 27 | 2,10,963 | 80,051 | 2.6 |
| 5 | 1e | 8.3 mM | 25.0 | 64 | 65,627 | 33,663 | 1.9 |
| 6 | 1f | 1.7 mM | 200 | 45 | 14,156 | 62,768 | 2.2 |
| 7 | 1g | 42 mM | 4.80 | 85 | 35,050 | 16,124 | 2.1 |
| 8 | 1h[c] | — | — | — | — | — | — |

[a]M = Monomer; PI = Photoinitiator; CI = co-initiator [CI] = triethanol amine employed in equimolar concentrations with respective to PI's. [Monomer] = 3.12 M. Solvent = MeCN concentrations of photoinitiators are prepared accordingly to achieve the optical density around ~0.2 at a wavelength ~390 nm. Irradiation was performed for 4 h.

[b] % conversion carry an error of 5% (average of three runs) and are determined gravimetrically by taking into account of isolated polymers 7. The values reported are an average of three runs.

[c]Benzoin 1h is insoluble in MeCN while adjusting the OD of ~0.2 at ~390 nm.

TABLE 3

Bio-mass derived photoinitators for acrylate polymerization at same concentration in the presence of triethanol amine as co-initiator using purple LED

| Entry | PI | % Conversion [b] | Mn | Mw | PDI |
|---|---|---|---|---|---|
| 1 | 1a | 19 | 91,960 | 11,295 | 2.6 |
| 2 | 1b | 13 | 1,64,586 | 11,597 | 2.5 |
| 3 | 1c | 22 | 78,808 | 11,529 | 2.7 |
| 4 | 1d | 28 | 80,552 | 17,421 | 2.3 |
| 5 | 1e | 51 | 53,251 | 32,144 | 2.0 |
| 6 | 1f | 53 | 33,011 | 10,936 | 2.2 |
| 7 | 1g | 45 | 67,817 | 5,872 | 1.9 |
| 8 | 1h | 30 | 1,04,671 | 1,91,908 | 1.8 |

[a] M = Monomer; PI = Photoinitiator; CI = co-initiator = triethanol amine. [PI] = 5 mM, [CI] = 5 mM, [Monomer] = 3.12 M. Photopolymerization were carried out with a purple LED strip ~390 nm (wrapped around a pyrex jar) illumination with a flux density of 1.5 mW/cm$^2$. Ee = Flux density (mW/cm$^2$) measured by Newport/spectra physics 407A Portable Laser Power Meter by keeping the sample at a distance of ~2 cm from the light source. Irradiation was performed for 4 h.

[b] % conversion carry an error of 5% (average of three runs) and are determined gravimetrically by taking into account of isolated polymers 7.

To have a comparative study between the photoinitiators, equimolar concentration of photoinitiators was employed in the photopolymerization of methylmethacrylate 6 (Table 3). The chloro-substituted derivatives 1b and 1e (Table 3; entry 2 and 5) gave 13% and 51% monomer conversion, respectively. The thio-methyl substituent on the para benzoyl derivative 1g (Table 3, entry 6) gave a high conversion of 45% concomitant with the previous data (Tables 1 and 2, entry 6). The cyano-substituent in both para-benzyl 1c (Table 3, entry 3) and para-benzoyl functionality 1f (Table 3, entry 6) gave high monomer conversions 22% and 53%, respectively, confirming the electron withdrawing group efficiency towards photoinitiation. The trifluoromethyl benzoin derivative 1d (Table 3, entry 4) gave the highest monomer conversion with respect to the substituents containing para-benzyl substitution (1a-1d), while methoxy-substituted benzoin 1a (Table 3, entry 1) gave moderate conversion of 19%. Following the trend of high percentage of monomer conversions with photoinitiators (Tables 2 and 3), in the presence of triethanol amine, 1e-1g (Table 3, entries 5-7) gave high monomer conversions surpassing the monomer conversion by simple benzoin 1 (Table 3, entry 8).

The bio-mass derived benzoin undergoes photodissociation reaction via Norrish type I α-cleavage, resulting in reactive radicals that initiate photo-polymerization (Scheme 4). In the presence of triethanol amines, long lived triplets of benzoins undergo electron transfer followed by proton transfer, resulting in reactive radicals that initiates photo-polymerization.

The examples herein confirm that the biomass derived benzoin photoinitiators, when derivatized, can be used as type I and type II photoinitiators for free radical polymerization. The photoinitiators can also work under visible light irradiation with much less concentration than the industrially preferred regular benzoin that operate near the UV region. These have been further confirmed by performing photopolymerization of acrylate yielding a high monomer conversion.

General Methods

All commercially obtained reagents/solvents were used as received; chemicals were purchased from Alfa Aesar®, Sigma-Aldrich®, Acros Organics®, TCI America®, and Oakwood® Products, and were used as received without further purification. Spectrophotometric grade solvents (e.g., acetonitrile, ethanol) were purchased from Sigma-Aldrich® and used without further purification for emission measurements. Unless stated otherwise, reactions were conducted in oven-dried glassware under nitrogen atmosphere. $^1$H-NMR and $^{13}$C-NMR spectra were recorded on Bruker 500 MHz (125 MHz for $^{13}$C) spectrometers. Data from the $^1$H-NMR spectroscopy are reported as chemical shift (δ ppm) with the corresponding integration values. Coupling constants (J) are reported in hertz (Hz). Standard abbreviations indicating multiplicity were used as follows: s (singlet), b (broad), d (doublet), t (triplet), q (quartet), m (multiplet), and virt (virtual). Data for $^{13}$C NMR spectra are reported in terms of chemical shift (δ ppm).

When necessary, the compounds were purified by combiflash equipped with dual wavelength UV-Vis absorbance detector (Teledyne ISCO) using hexanes:ethyl acetate as the mobile phase and Redisep® cartridge filled with silica (Teledyne ISCO) as the stationary phase. In some cases, compounds were purified by column chromatography on silica gel (Sorbent Technologies®, silica gel standard grade: porosity 60 Å, particle size: 230×400 mesh, surface area: 500-600 m$^2$/g, bulk density: 0.4 g/mL, pH range: 6.5-7.5). Unless indicated, the Retention Factor ($R_f$) values were recorded using a 5-50% hexanes:ethyl acetate as the mobile phase and on Sorbent Technologies®, silica Gel TLC plates (200 mm thickness w/UV254).

Photophysical Methods

Spectrophotometric solvents (Sigma-Aldrich®) were used whenever necessary unless or otherwise mentioned. UV quality fluorimeter cells (with range until 190 nm) were purchased from Luzchem®. Absorbance measurements were performed using a Cary 300 UV-Vis spectrophotometer.

Gel Permeations Chromatography (GPC) Analysis

Polymer sample analysis was performed on EcoSEC GPC System (HLC-8320) equipped with a dual flow refractive index detector (RI) detector. Separation of injections occurred over a column bank consisting of two 67.8 mm ID×30 cm, 5 μm particle size TSKgel® multiporeH xL (exclusion limit 6×104 g/mol), and one 6 mm ID×15 cm, 4 μm particle size TSKgel SuperH-RC (exclusion limit 5×105 g/mol) columns (Tosoh Bioscience LLC). Tetrahydrofuran (THF) (HPLC grade, EMD Omnisolv®) was used as mobile phase and solvents for sample preparation were at flow rate of 1 mL/min. Detector, pump oven, and column oven were maintained at 40° C. Polystyrene kits with PStQuick C (Lot No: PSQ-D02C) and PStQuick C (Lot No: PSQ-C04C). All the molecular weight values (Mw, Mn, and PDI) results are calculated based on a polystyrene calibration curve. Concentration of polymer samples for GPC analysis: 1 mg/ml in THF and soaked the samples overnight. The saturated compounds were filtered through 25 mm, 0.2 μm PTFE membrane filter.

Chemical Structures of Benzoin Photoinitiators, Monomer and Polymers

Chemical structures of benzoin photoinitiators, monomer and polymers FIG. 7.

General Procedure for the Synthesis of Benzoin Derivatives

Synthesis of Dithiane Derivatives 3a, 3e-3g

Figure 8:
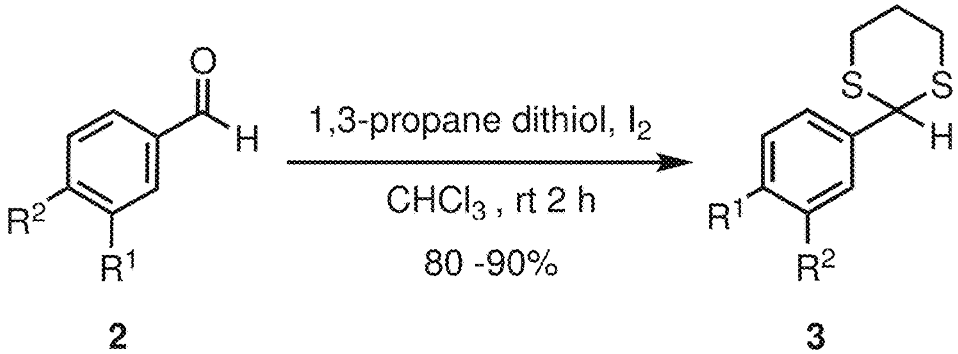
FIG. 8: Scheme 5: Synthesis of dithiane derivatives 3a, 3e-3g.

The synthesis of dithiane derivatives 3a, 3e-3g is depicted in FIG. 8.

To a solution of benzaldehyde derivative 2 (1.0 equiv) Iodine (0.1 equiv) was dissolved in $CHCl_3$ (45 mL) and 1,3-propane dithiol (1.4 equiv) was added and the resulting mixture was stirred for 2 h at room temperature. After the completion of reaction, the solution was diluted with $CHCl_3$ (3×50 mL) and quenched with NaOH (2.5 M, 25 mL) and $Na_2SO_3$ (0.1 M, 25 mL), respectively. The obtained organic layer was washed with brine solution. The combined organic layer was dried over anhyd. $Na_2SO_4$, and solvent was removed under reduced pressure to get the crude product. The crude product was purified by Combiflash using hexanes:ethyl acetate mixture.

3a

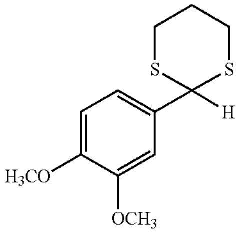

Figure 14A:
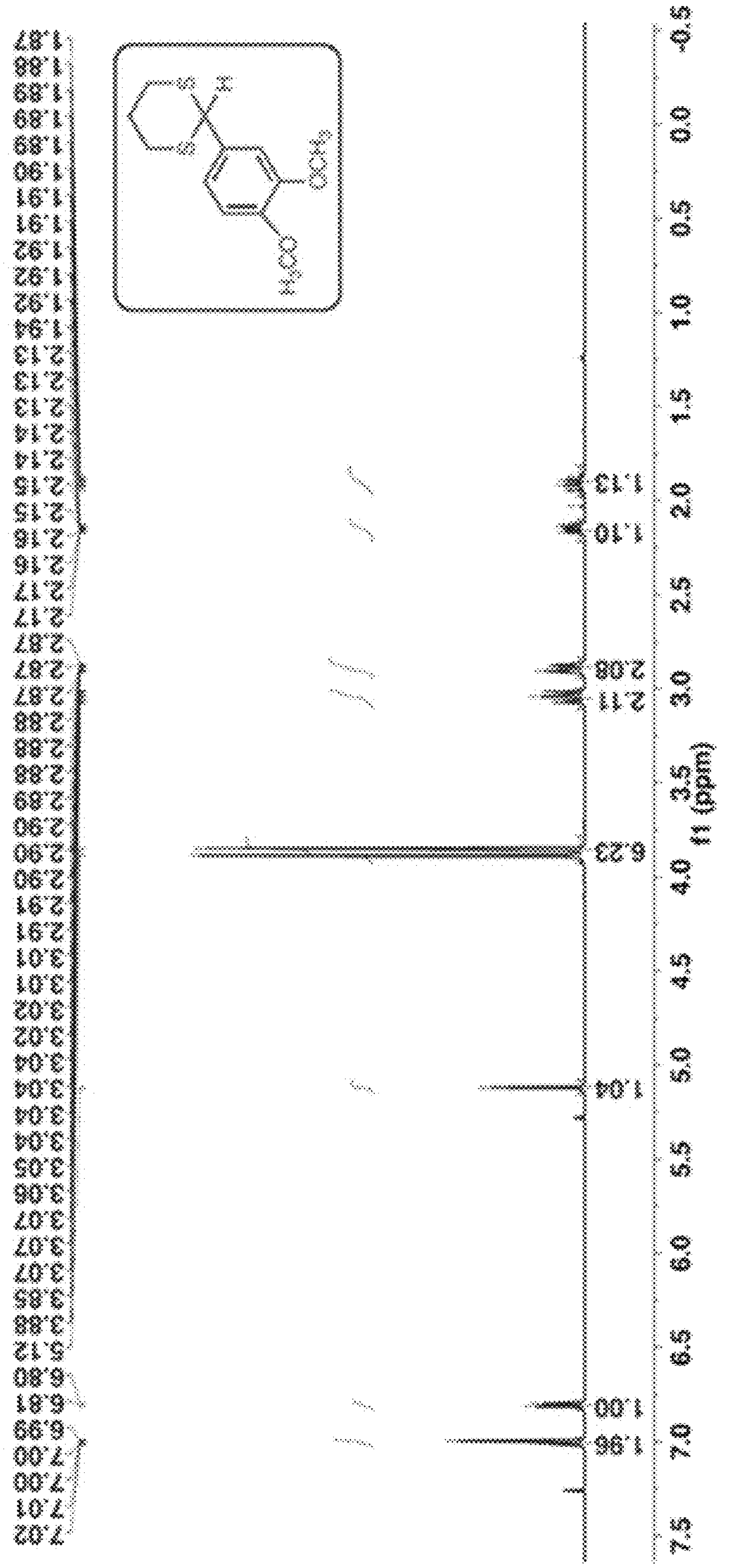
Figure 14B:
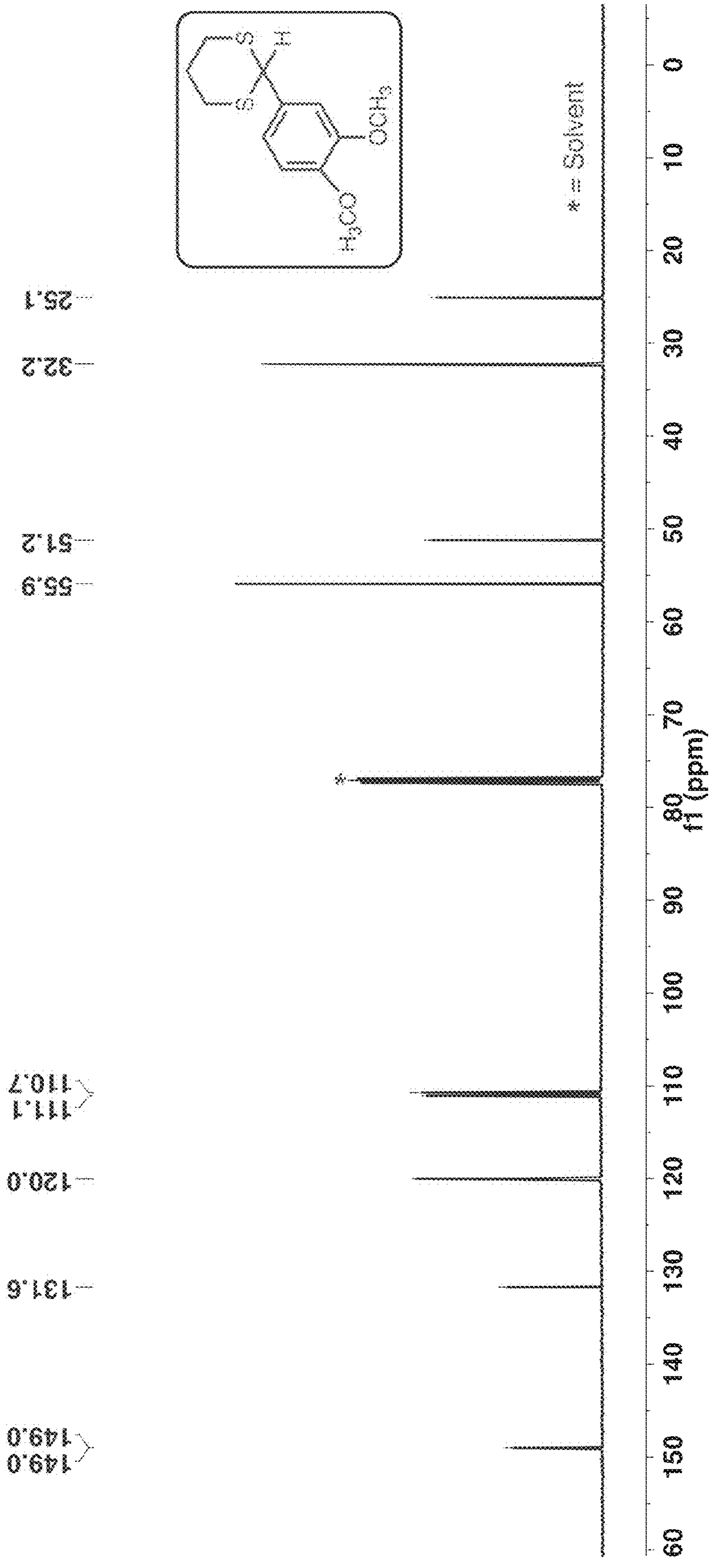

$R_f$=0.47 (30% ethyl acetate: 70% hexanes) for 3a, (Yield=89%). $^{1}$H NMR (500 MHz, $CDCl_3$, δ ppm) 7.03-6.98 (m, 2H), 6.81 (d, J=8.0 Hz, 1H), 5.12 (s, 1H), 3.87 (d, J=17.5 Hz, 6H), 3.11-3.00 (m, 2H), 2.94-2.83 (m, 2H), 2.15 (dtt, J=13.9, 4.6, 2.5 Hz, 1H), 1.98-1.82 (m, 1H). $^{13}$C NMR (125 MHz, $CDCl_3$, δ ppm) 149.0, 149.0, 131.7, 120.0, 111.1, 110.7, 55.9, 51.2, 32.2, 25.1. FIGS. 14A-14B show the $^{1}$H NMR spectrum (FIG. 14A) and $^{13}$C NMR spectrum (FIG. 14B) of dithiane protected dimethoxybenzaldehyde 3a.

3e

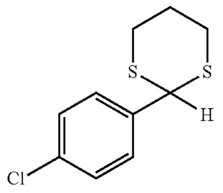

Figure 15A:
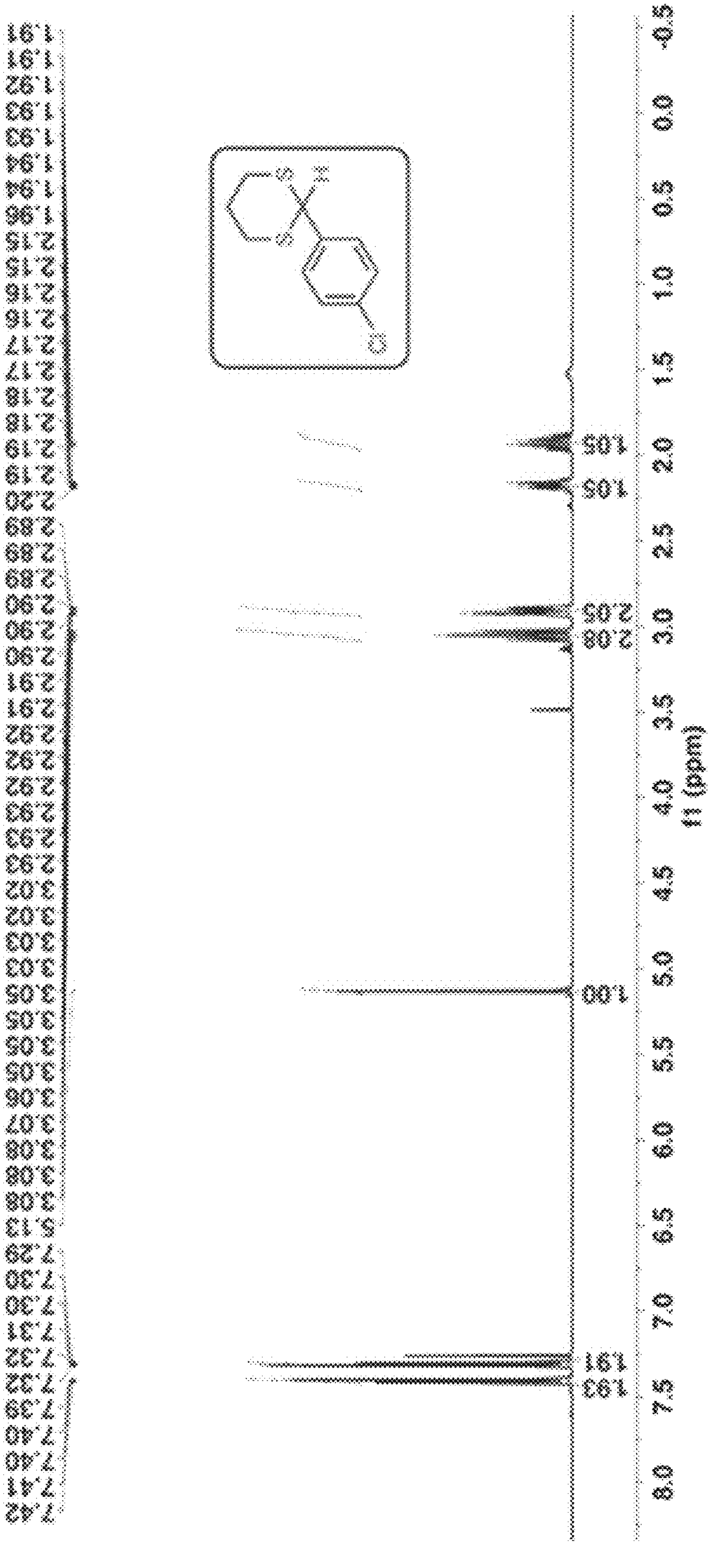
FIG. 15A-15B: $^1H$ NMR spectrum (FIG. 15A) and $^{13}C$ NMR spectrum (FIG. 15B) of dithiane protected chlorobenzaldehyde 3e.
Figure 15B:
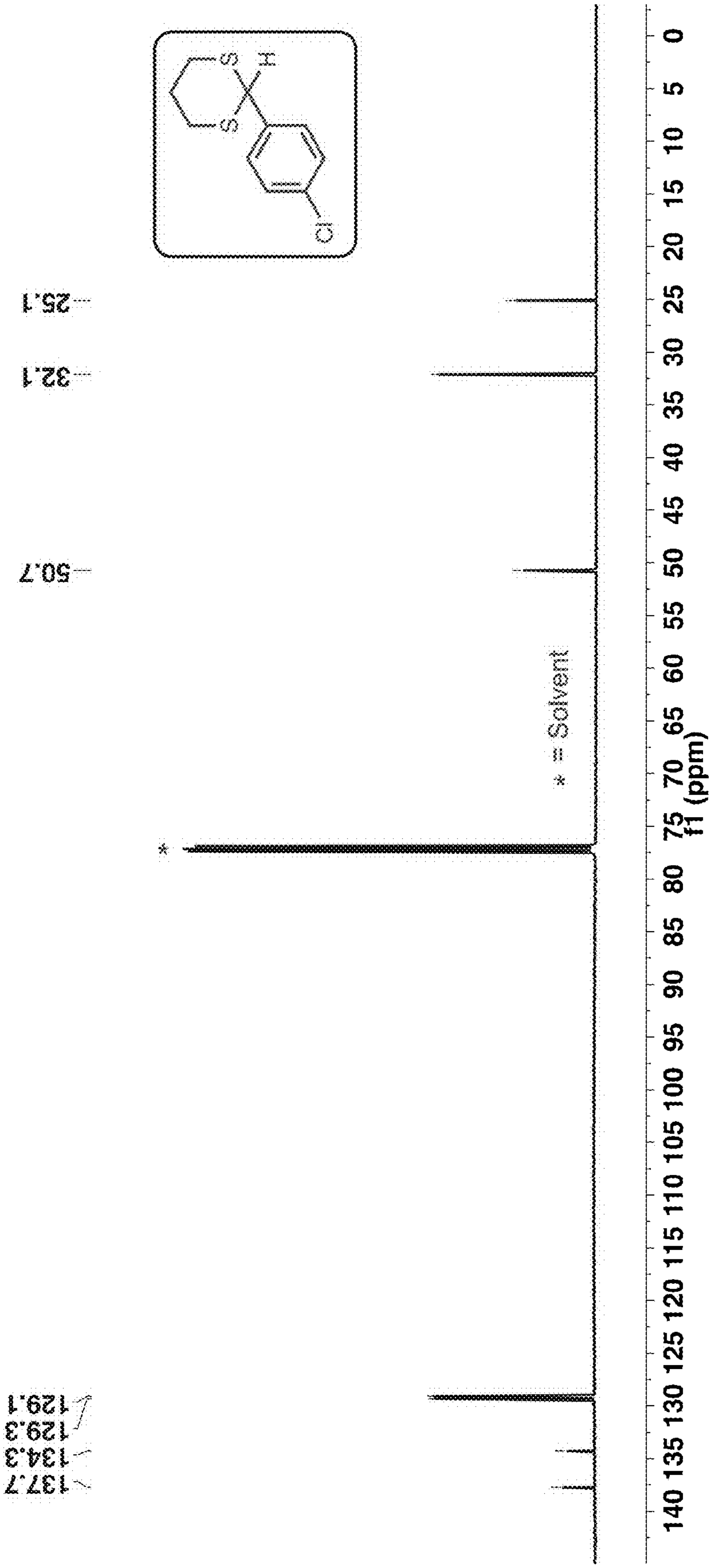

$R_f$=0.35 (30% ethyl acetate: 70% hexanes) for 3e, (Yield=90%). $^{1}$H NMR (500 MHz, $CDCl_3$, δ ppm) 7.43-7.39 (m, 2H), 7.33-7.29 (m, 2H), 5.13 (s, 1H), 3.09-3.01 (m, 2H), 2.91 (dddd, J=13.5, 4.4, 3.0, 1.0 Hz, 2H), 2.17 (dtt, J=14.0, 4.6, 2.4 Hz, 1H), 1.92 (dtt, J=14.2, 12.4, 3.1 Hz, 1H). $^{13}$C NMR (125 MHz, $CDCl_3$, δ ppm) 137.7, 134.3, 129.3, 129.1, 50.7, 32.1, 25.1. FIGS. 15A-15B show the $^{1}$H NMR spectrum (FIG. 15A) and $^{13}$C NMR spectrum (FIG. 15B) of dithiane protected chlorobenzaldehyde 3e.

3f

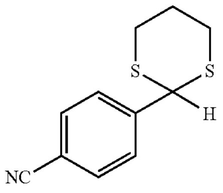

Figure 16A:
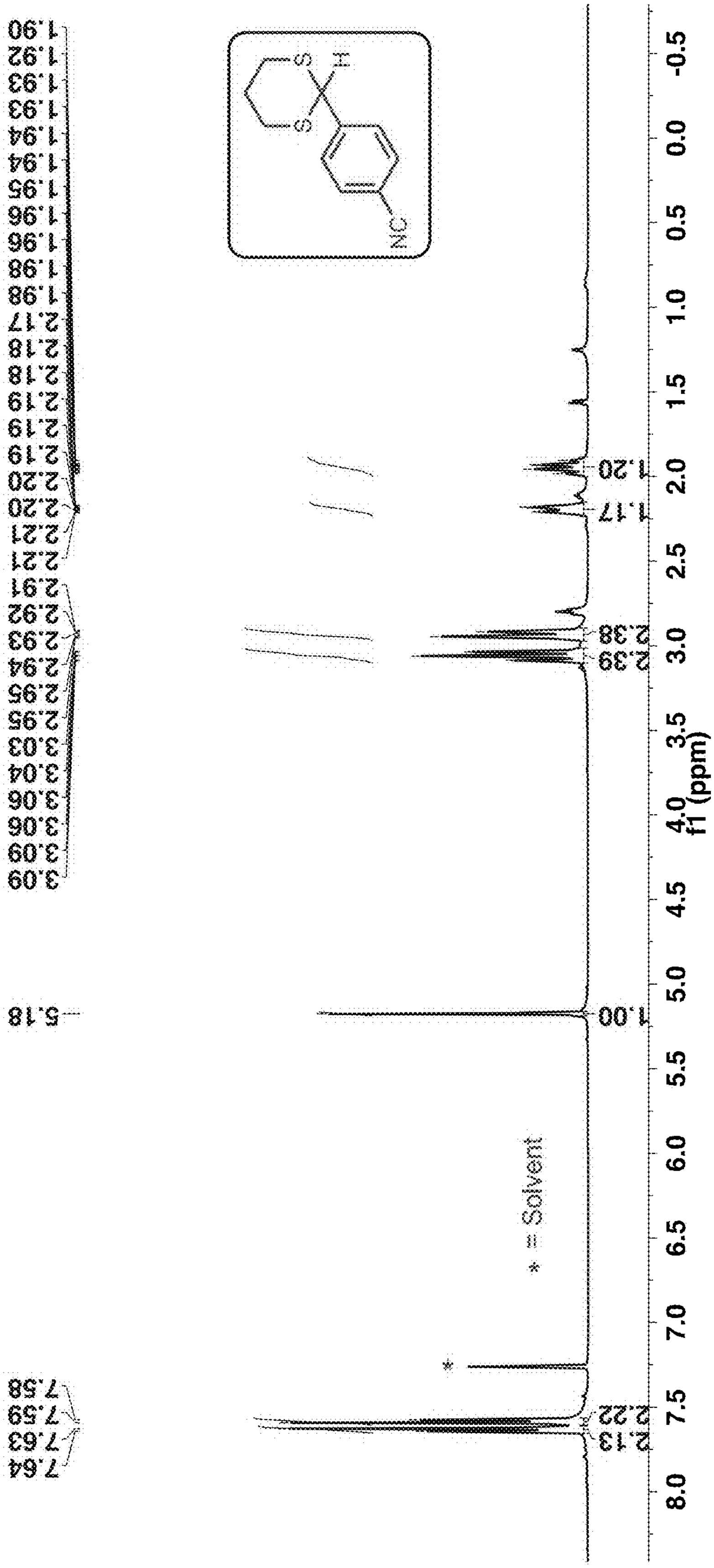
FIG. 16A-16B: $^1H$ NMR spectrum (FIG. 16A) and $^{13}C$ NMR spectrum (FIG. 16B) of dithiane protected cyanobenzaldehyde 3f.
Figure 16B:
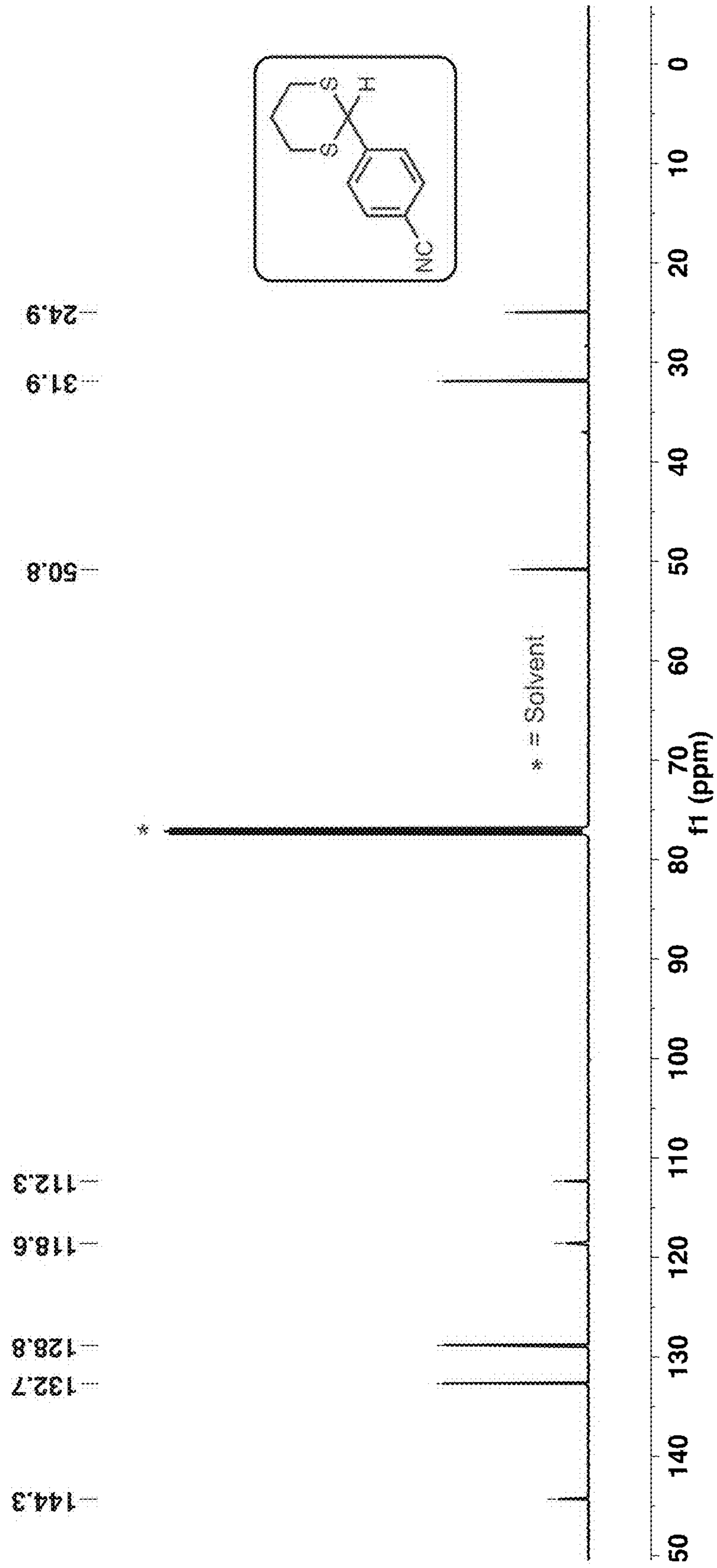

$R_f$=0.40 (15% ethyl acetate: 75% hexanes) for 3f, (Yield=85%). $^{1}$H NMR (500 MHz, $CDCl_3$, δ ppm) 7.64 (d, J=8.0 Hz, 2H), 7.58 (d, J=8.1 Hz, 2H), 5.18 (s, 1H), 3.06 (td, J=13.1, 11.9, 2.3 Hz, 2H), 2.93 (dt, J=14.3, 3.8 Hz, 2H), 2.19 (ddt, J=11.7, 4.6, 2.3 Hz, 1H), 2.01-1.86 (m, 1H). $^{13}$C NMR (125 MHz, $CDCl_3$, δ ppm) 144.3, 132.7, 128.8, 118.6, 112.3, 50.8, 31.9, 24.9. FIGS. 16A-16B show the $^{1}$H NMR spectrum (FIG. 16A) and $^{13}$C NMR spectrum (FIG. 16B) of dithiane protected cyanobenzaldehyde 3f.

3g

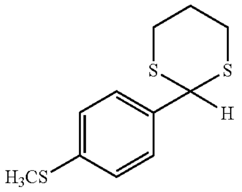

Figure 17A:
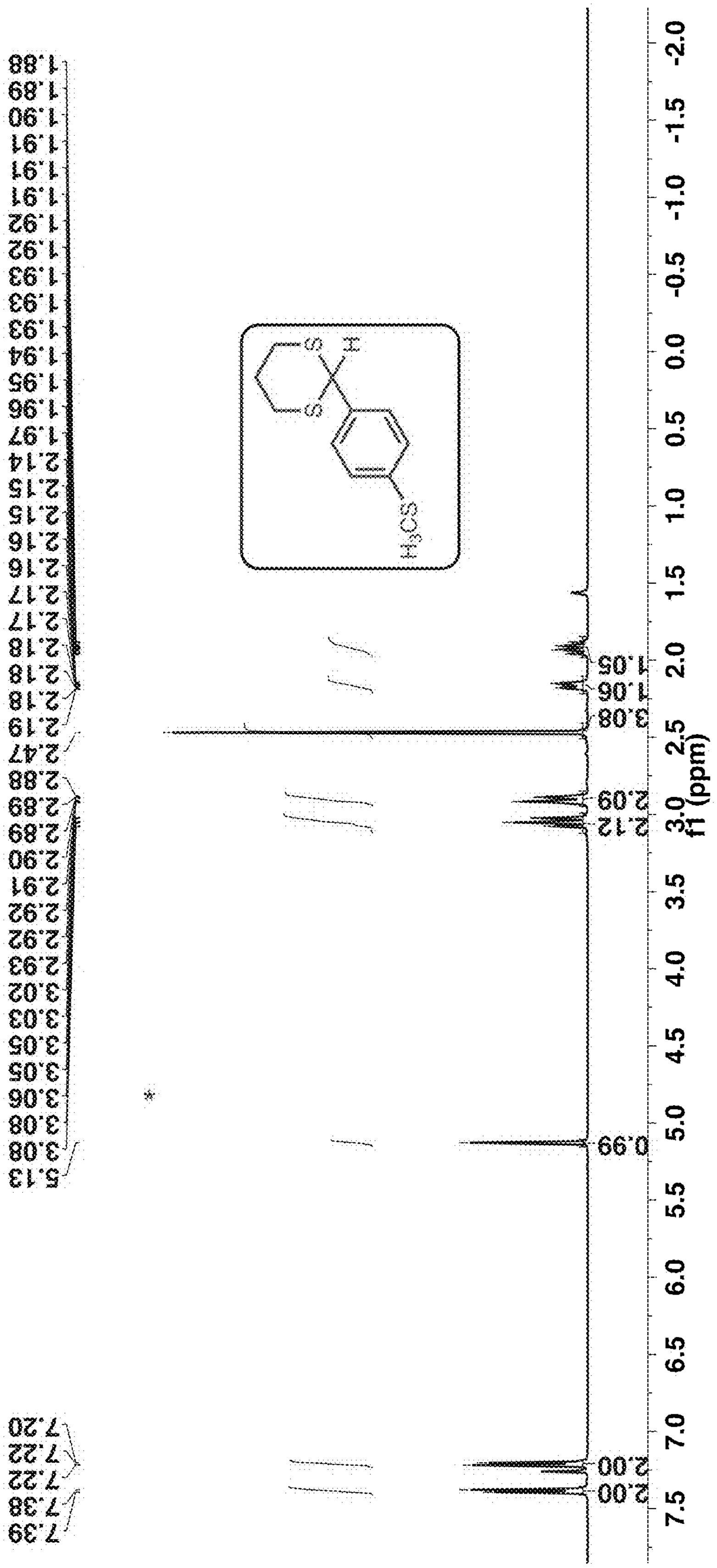
FIG. 17A-17B: $^1H$ NMR spectrum (FIG. 17A) and $^{13}C$ NMR spectrum (FIG. 17B) of dithiane protected dimethoxybenzaldehyde 3g.
Figure 17B:
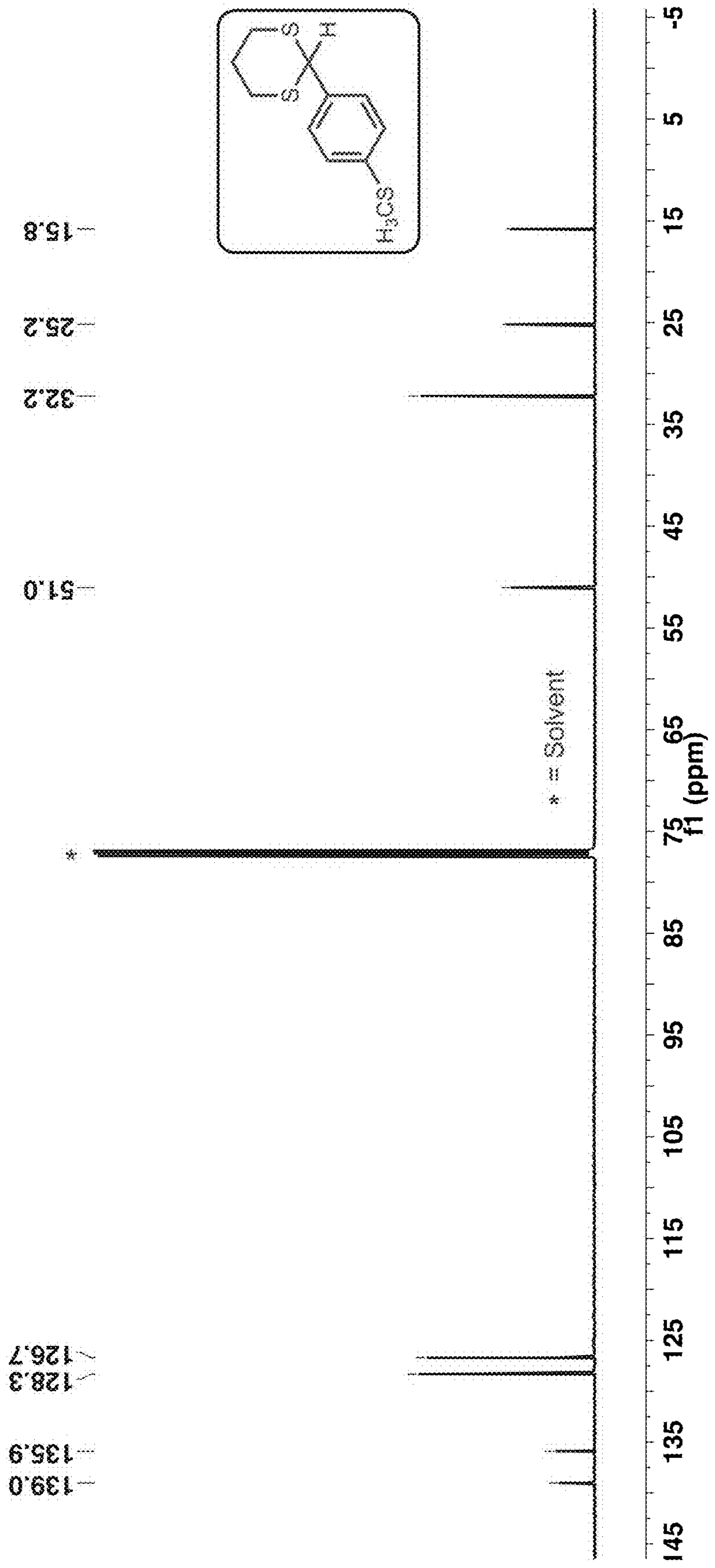

$R_f$=0.40 (20% ethyl acetate: 80% hexanes) for 3g, (Yield=87%). $^{1}$H NMR (500 MHz, $CDCl_3$, δ ppm) 7.39 (d, J=8.4 Hz, 2H), 7.23-7.18 (m, 2H), 5.13 (s, 1H), 3.05 (ddd, J=14.8, 12.5, 2.4 Hz, 2H), 2.95-2.85 (m, 2H), 2.47 (s, 3H), 2.22-2.10 (m, 1H), 1.98-1.85 (m, 1H). $^{13}$C NMR (125 MHz, $CDCl_3$, δ ppm) 139.0, 135.9, 128.3, 126.7, 51.0, 32.2, 25.2, 15.8. FIGS. 17A-17B show the $^{1}$H NMR spectrum (FIG. 17A) and $^{13}$C NMR spectrum (FIG. 17B) of dithiane protected dimethoxybenzaldehyde 3g.

Synthesis of Hydroxy Derivatives 5a-5g

Figure 9:
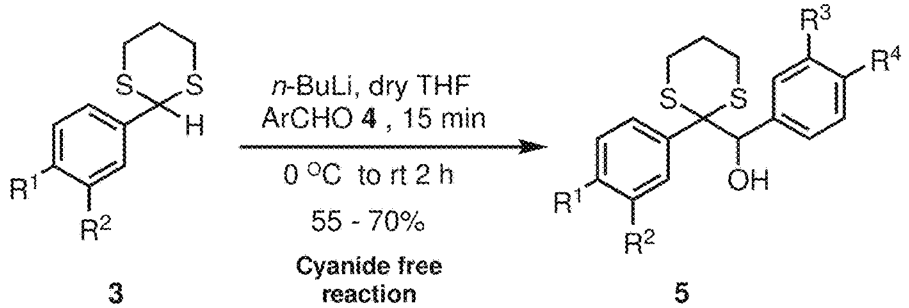
FIG. 9: Scheme 6: Synthesis of hydroxy derivatives 5a-5g.

The synthesis of hydroxy derivatives 5a-5g is depicted in FIG. 9.

To a solution of 3 (1.0 equiv) in dry THF (30 mL) at 0° C., n-BuLi (1.6 mM in hexane, 1.5 equiv) was added slowly over 15 min. The resulting mixture was allowed to stir at 0° C. for 30 minutes. A solution of benzaldehyde derivative 4 (in dry THF) was added slowly. The mixture was then brought to room temperature and stirred for 2 h. After completion of reaction, the mixture was quenched with saturated $NH_4Cl$ solution and washed with brine and ethyl acetate (3×50 mL). The combined organic layers were dried over anhyd. $Na_2SO_4$. Ethyl acetate was removed under reduced pressure to get the crude product. The crude product was purified by combiflash using hexanes:ethyl acetate mixture.

5a

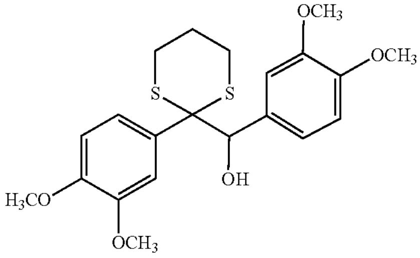

Figure 18A:
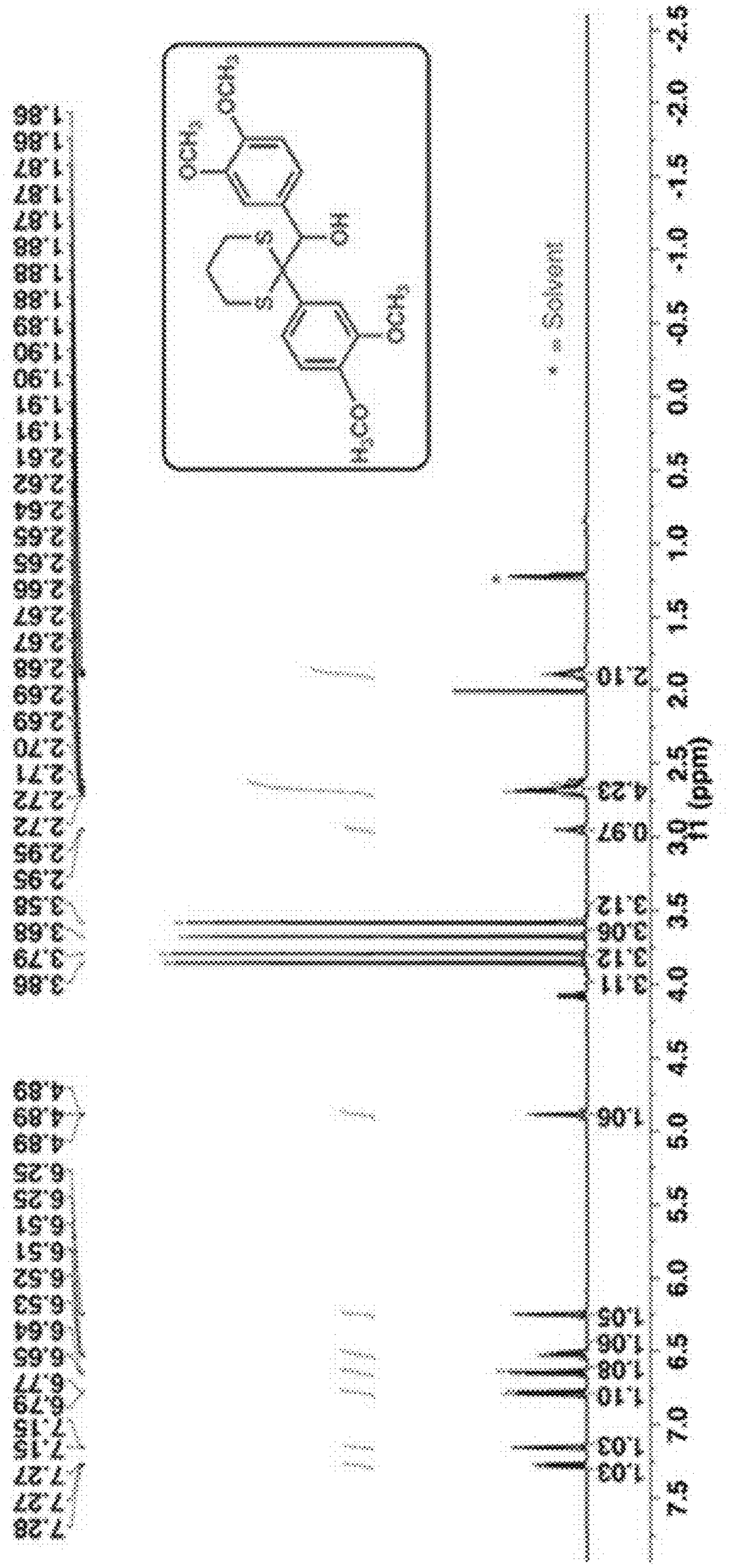
Figure 18B:
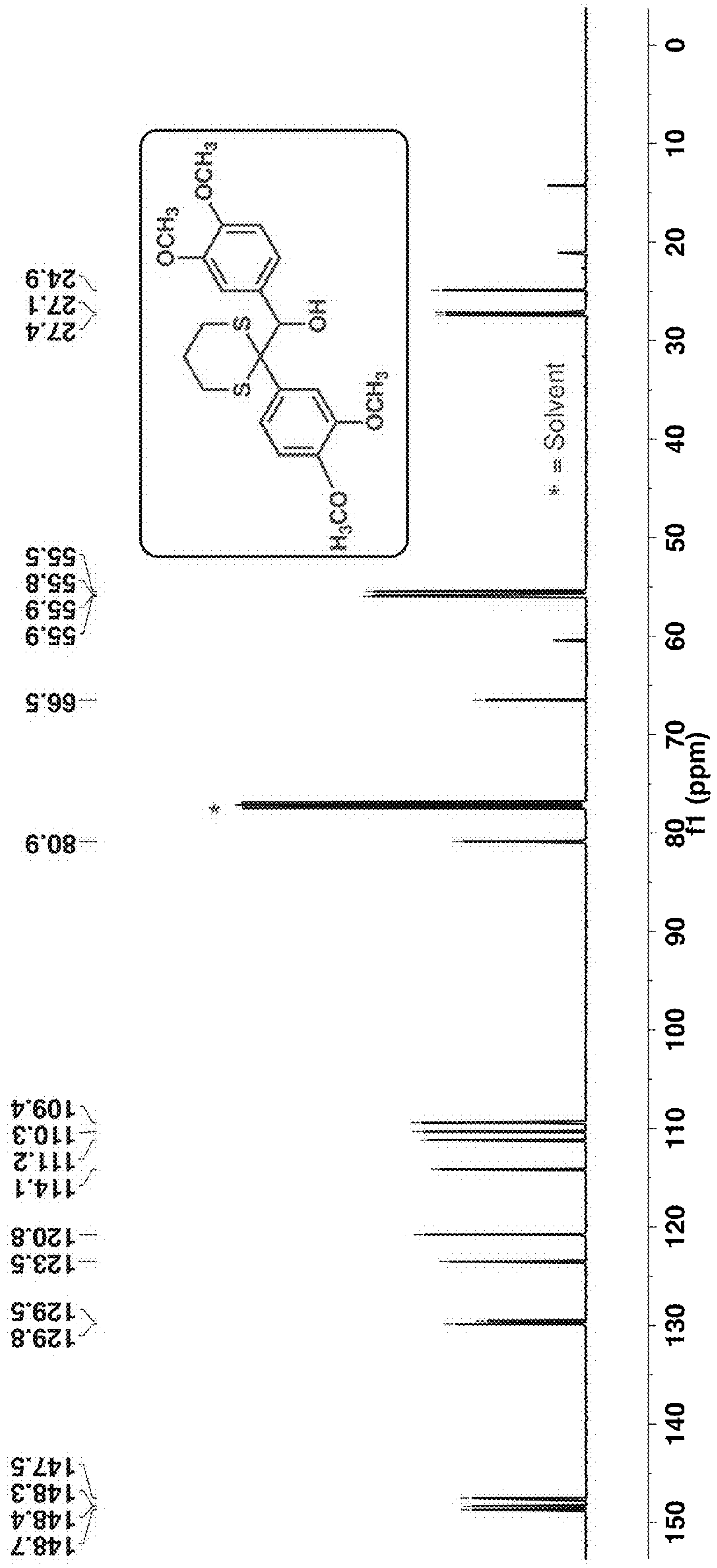

$R_f$=0.25 (50% ethyl acetate: 50% hexanes) for 5a, (Yield=70%). $^{1}$H NMR (500 MHz, $CDCl_3$, δ ppm) 7.28 (dd, J=8.5, 2.3 Hz, 1H), 7.15 (d, J=2.3 Hz, 1H), 6.78 (d, J=8.5 Hz, 1H), 6.65 (d, J=8.3 Hz, 1H), 6.52 (dd, J=8.3, 2.1 Hz, 1H), 6.25 (d, J=2.0 Hz, 1H), 4.93-4.85 (m, 1H), 3.86 (s, 3H), 3.79 (s, 3H), 3.68 (s, 3H), 3.58 (s, 3H), 2.95 (d, J=3.4 Hz, 1H), 2.72-2.61 (m, 4H), 1.93-1.84 (m, 2H). $^{13}$C NMR (125 MHz, $CDCl_3$, δ ppm) 148.7, 148.4, 148.3, 147.5, 129.8, 129.5, 123.5, 120.8, 114.1, 111.2, 110.3, 109.4, 80.9, 66.5, 55.9, 55.9, 55.8, 55.5, 27.4, 27.1, 24.9. FIGS. 18A-18B show the $^{1}$H NMR spectrum (FIG. 18A) and $^{13}$C NMR spectrum (FIG. 18B) of dimethoxy derived benzyl alcohol 5a.

5b

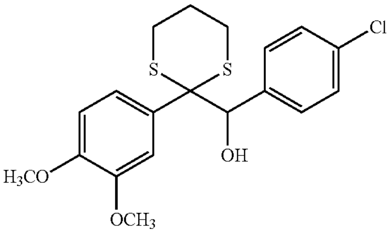

Figure 19A:
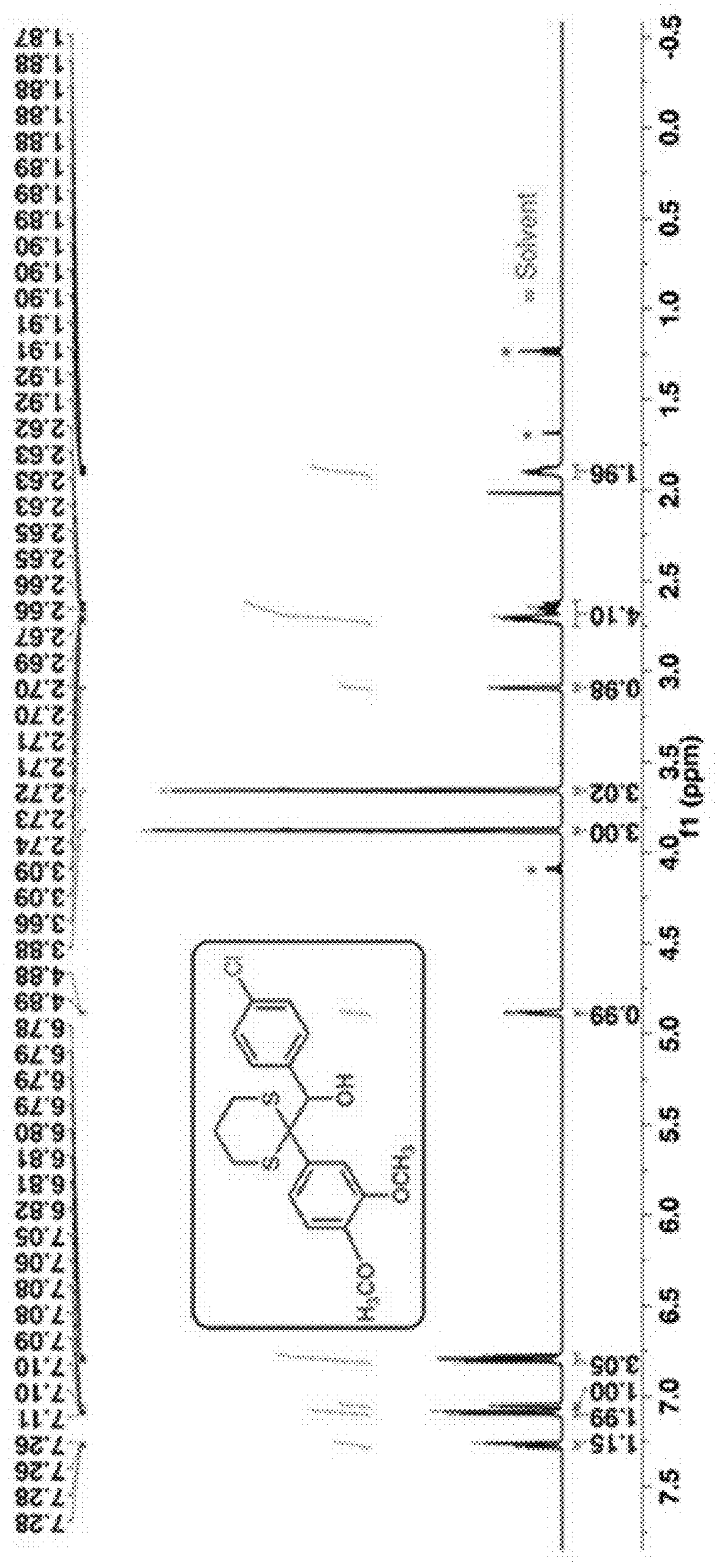
FIGS. 19A-19B: $^{1}H$ NMR spectrum (FIG. 19A) and $^{13}C$ NMR spectrum (FIG. 19B) of chloro benzyl alcohol 5b.
Figure 19B:
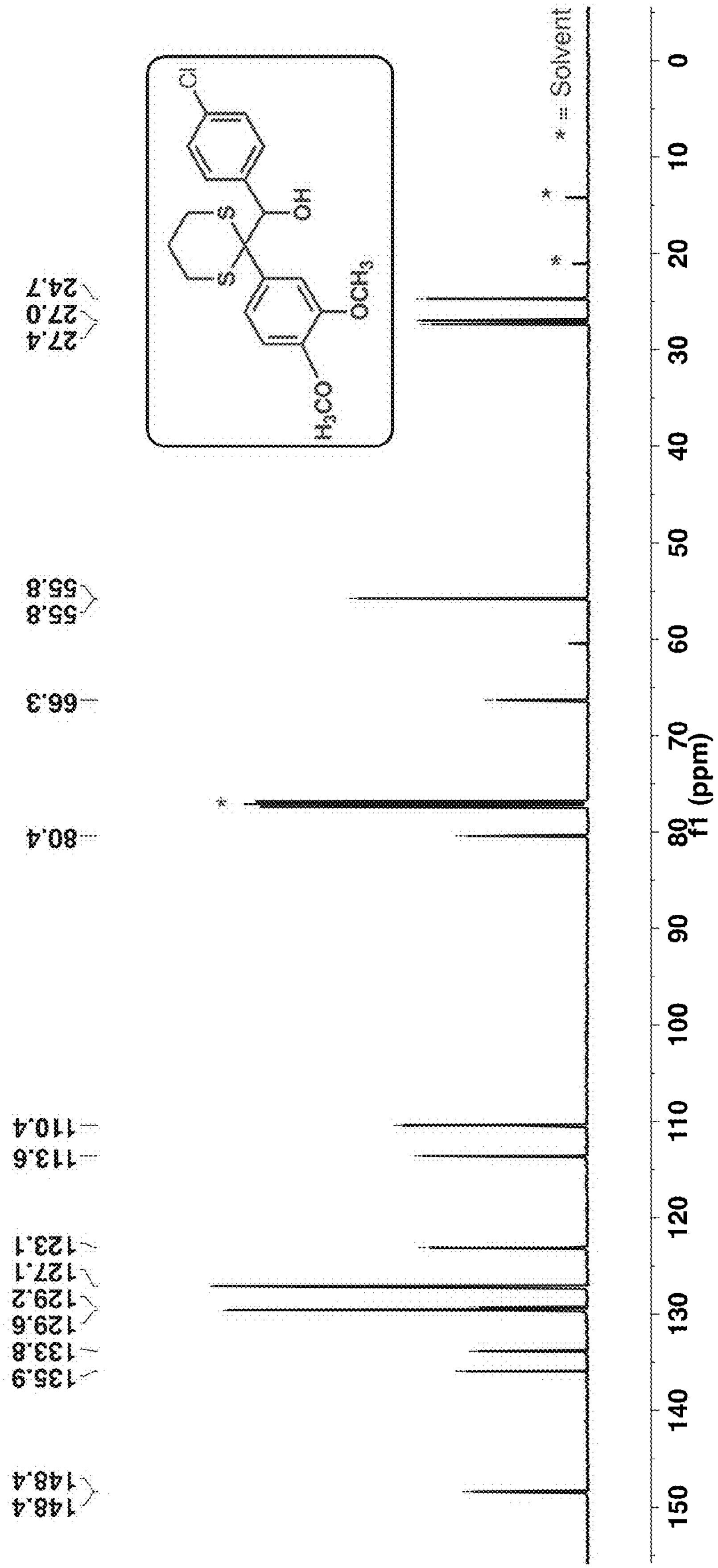

$R_f$=0.45 (30% ethyl acetate: 70% hexanes) for 5b, (Yield=68%). $^1$H NMR (500 MHz, $CDCl_3$, δ ppm) 7.29-7.25 (m, 1H), 7.11-7.07 (m, 2H), 7.05 (d, J=2.3 Hz, 1H), 6.79 (dd, J=8.5, 7.7 Hz, 3H), 4.88 (d, J=3.5 Hz, 1H), 3.88 (s, 3H), 3.66 (s, 3H), 3.09 (d, J=3.6 Hz, 1H), 2.75-2.61 (m, 4H), 1.93-1.86 (m, 2H). $^{13}$C NMR (125 MHz, $CDCl_3$, δ ppm) 148.4, 148.4, 135.9, 133.8, 129.6, 129.2, 127.1, 123.1, 113.6, 110.4, 80.4, 66.3, 55.8, 55.8, 27.4, 27.0, 24.7. FIGS. 19A-19B show the $^1$H NMR spectrum (FIG. 19A) and $^{13}$C NMR spectrum (FIG. 19B) of chloro benzyl alcohol 5b.

5c

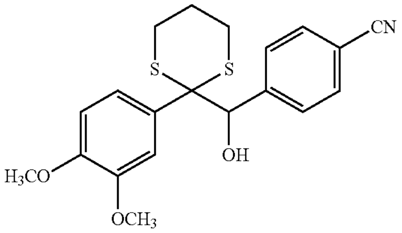

Figure 20A:
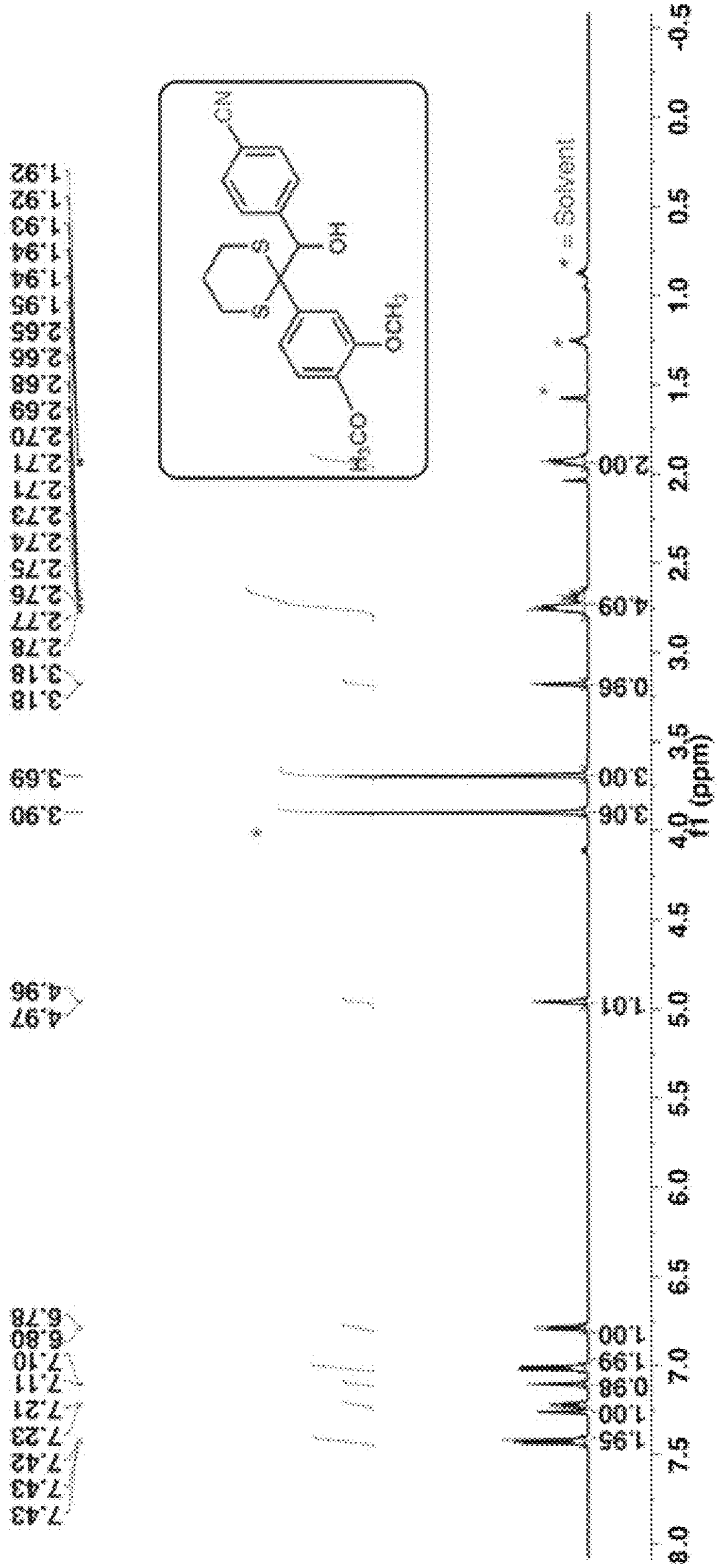
FIG. 20A-20B: $^{1}H$ NMR spectrum (FIG. 20A) and $^{13}C$ NMR spectrum (FIG. 20B) of cyano benzyl alcohol 5c.
Figure 20B:
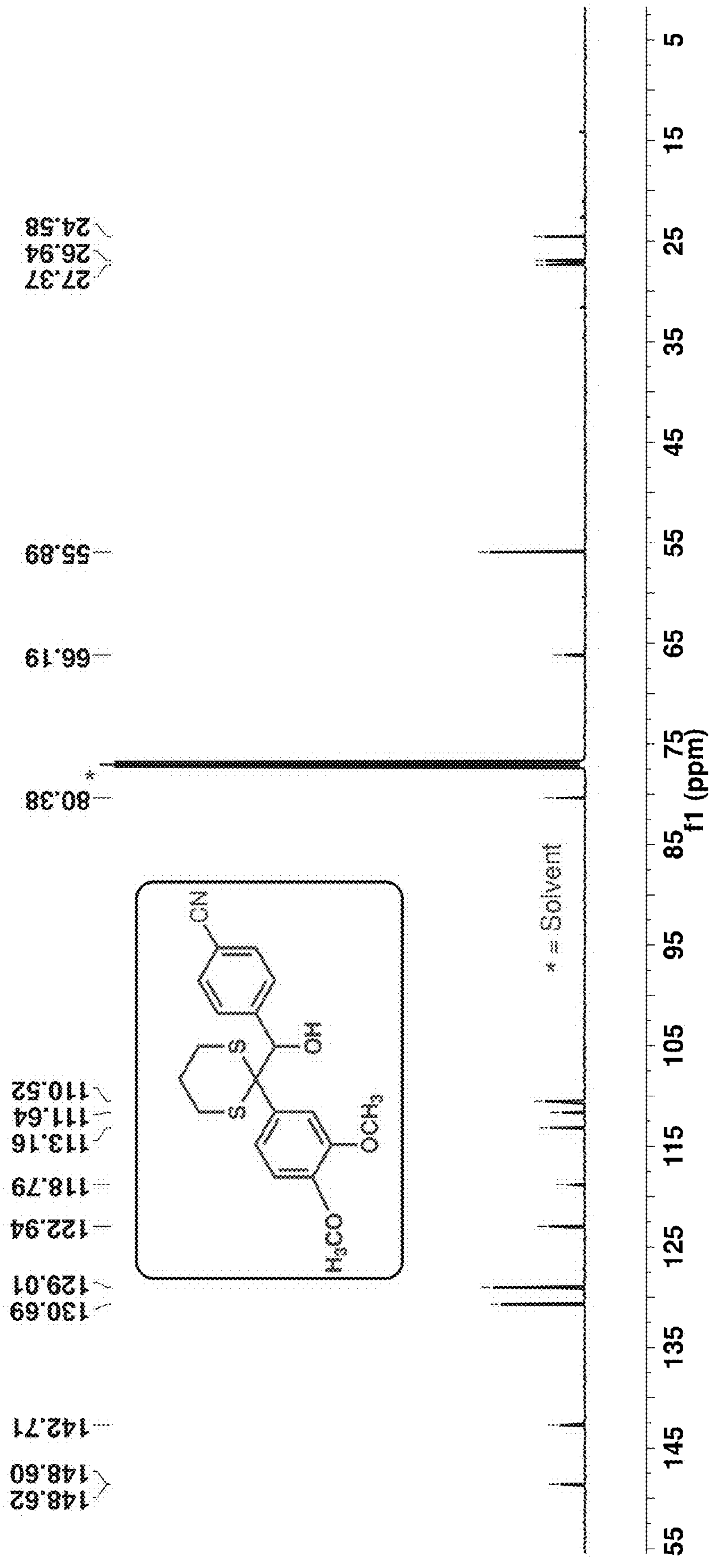

$R_f$=0.30 (30% ethyl acetate: 70% hexanes) for 5c, (Yield=65%). $^1$H NMR (500 MHz, $CDCl_3$, δ ppm) 7.43 (d, J=8.3 Hz, 2H), 7.22 (dd, J=8.5, 2.3 Hz, 1H), 7.11 (d, J=2.2 Hz, 1H), 7.03-6.99 (m, 2H), 6.79 (d, J=8.5 Hz, 1H), 4.96 (d, J=3.2 Hz, 1H), 3.90 (s, 3H), 3.69 (s, 3H), 3.18 (d, J=3.3 Hz, 1H), 2.82-2.58 (m, 4H), 1.99-1.87 (m, 2H). $^{13}$C NMR (125 MHz, $CDCl_3$, δ ppm) 148.6, 148.6, 142.7, 130.7, 129.0, 122.9, 118.7, 113.1, 111.6, 110.5, 80.3, 66.1, 55.8, 27.3, 26.9, 24.5. FIG. 20A-20B show the $^1$H NMR spectrum (FIG. 20A) and $^{13}$C NMR spectrum (FIG. 20B) of cyano benzyl alcohol 5c.

5d

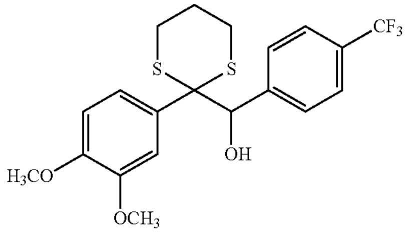

Figure 21A:
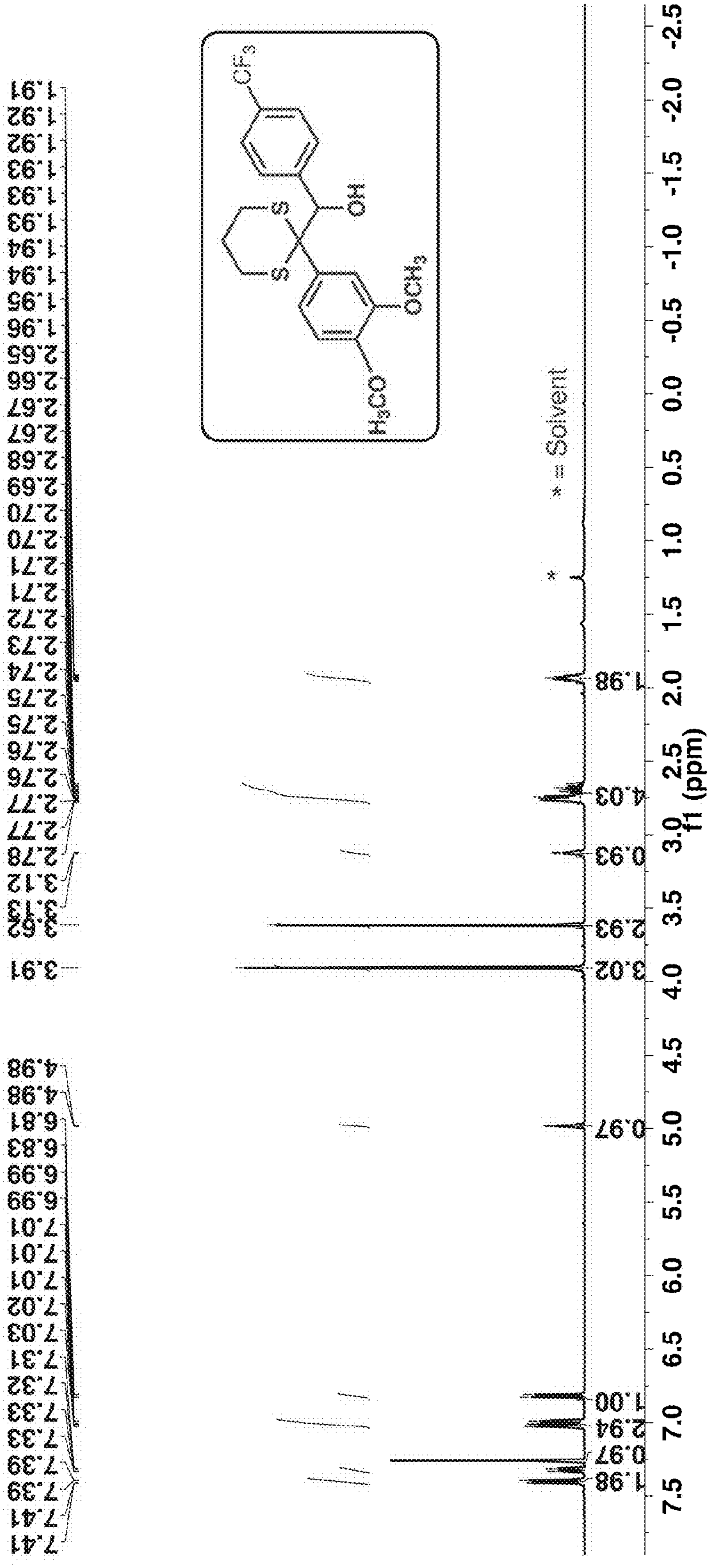
FIG. 21A-21B: $^{1}H$ NMR spectrum (FIG. 21A) and $^{13}C$ NMR spectrum (FIG. 21B) of trifluoromethyl benzyl alcohol 5d.
Figure 21B:
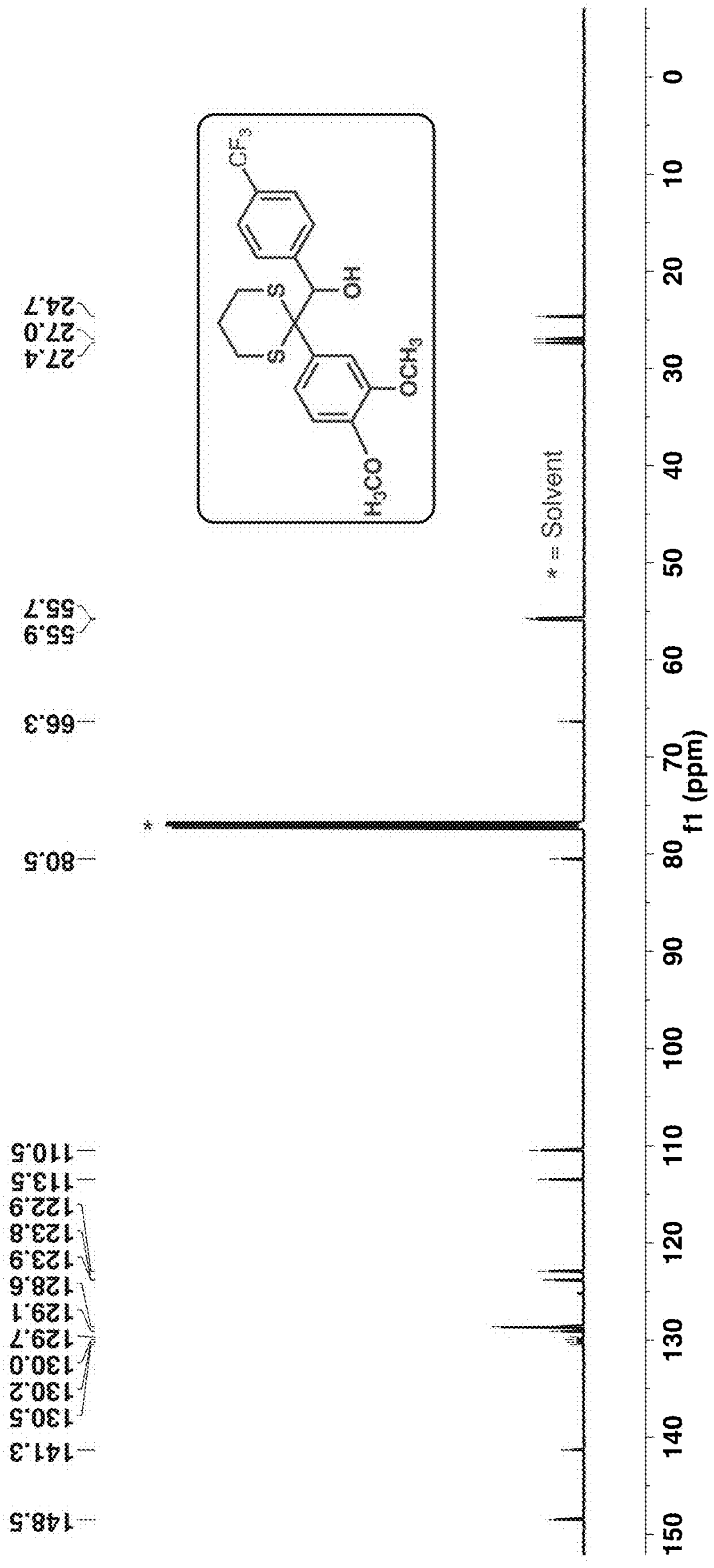

$R_f$=0.35 (30% ethyl acetate: 70% hexanes) for 5d, (Yield=60%). $^1$H NMR (500 MHz, $CDCl_3$, δ ppm) 7.42-7.38 (m, 2H), 7.32 (dd, J=8.5, 2.3 Hz, 1H), 7.04-6.98 (m, 3H), 6.82 (d, J=8.5 Hz, 1H), 4.98 (d, J=2.6 Hz, 1H), 3.91 (s, 3H), 3.62 (s, 3H), 3.12 (d, J=3.4 Hz, 1H), 2.79-2.65 (m, 4H), 1.97-1.90 (m, 2H). $^{13}$C NMR (125 MHz, $CDCl_3$, δ ppm) 148.5, 141.3, 130.5, 130.2, 130.0, 129.7, 129.1, 128.6, 123.9, 123.8, 122.9, 113.5, 110.5, 80.5, 66.3, 55.9, 55.7, 27.4, 27.0, 24.7. FIGS. 21A-21B show the $^1$H NMR spectrum (FIG. 21A) and $^{13}$C NMR spectrum (FIG. 21B) of trifluoromethyl benzyl alcohol 5d.

5e

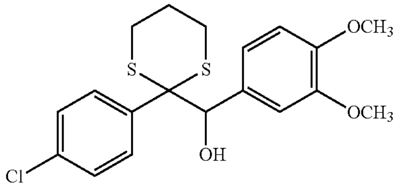

Figure 22A:
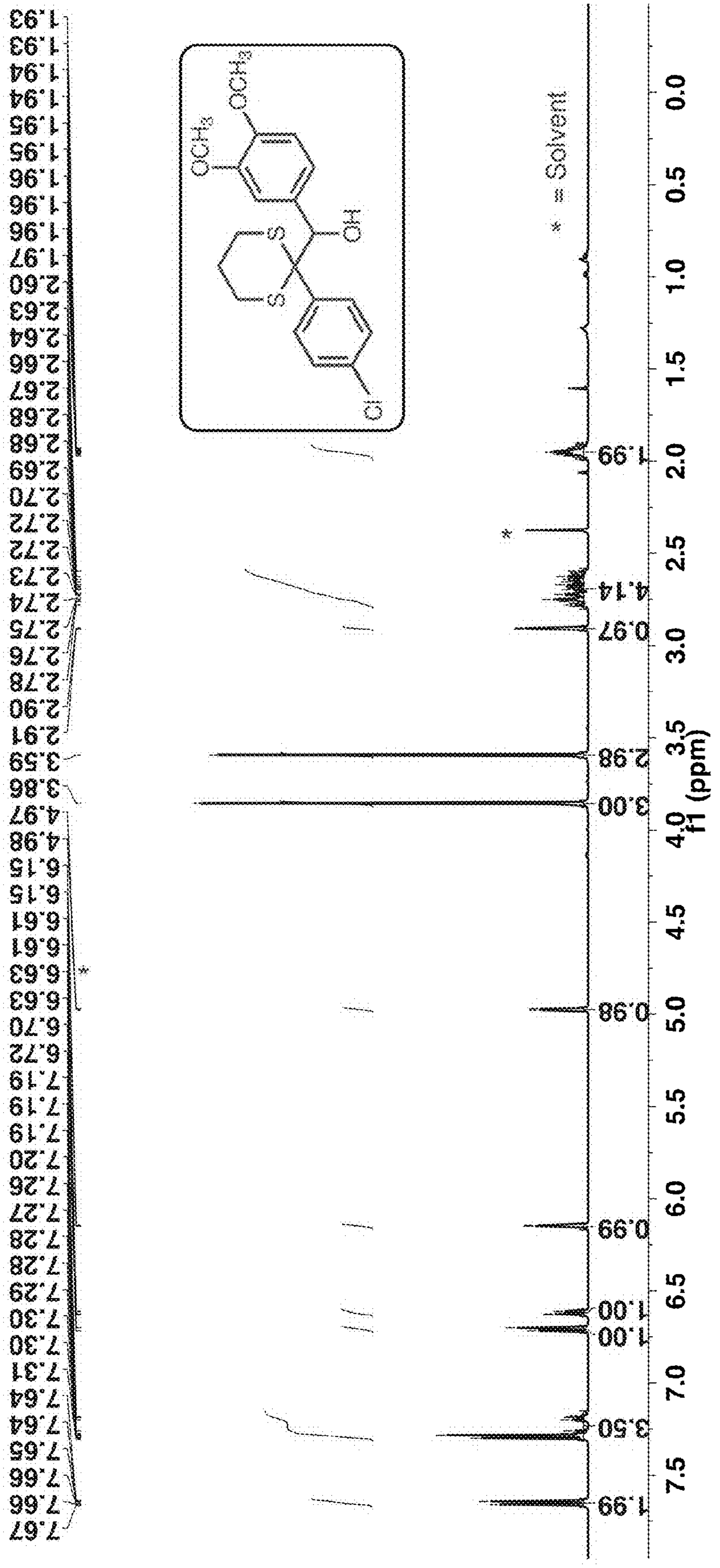
FIG. 22A-22B: $^{1}H$ NMR spectrum (FIG. 22A) and $^{13}C$ NMR spectrum (FIG. 22B) of chloro derived benzyl alcohol 5e.
Figure 22B:
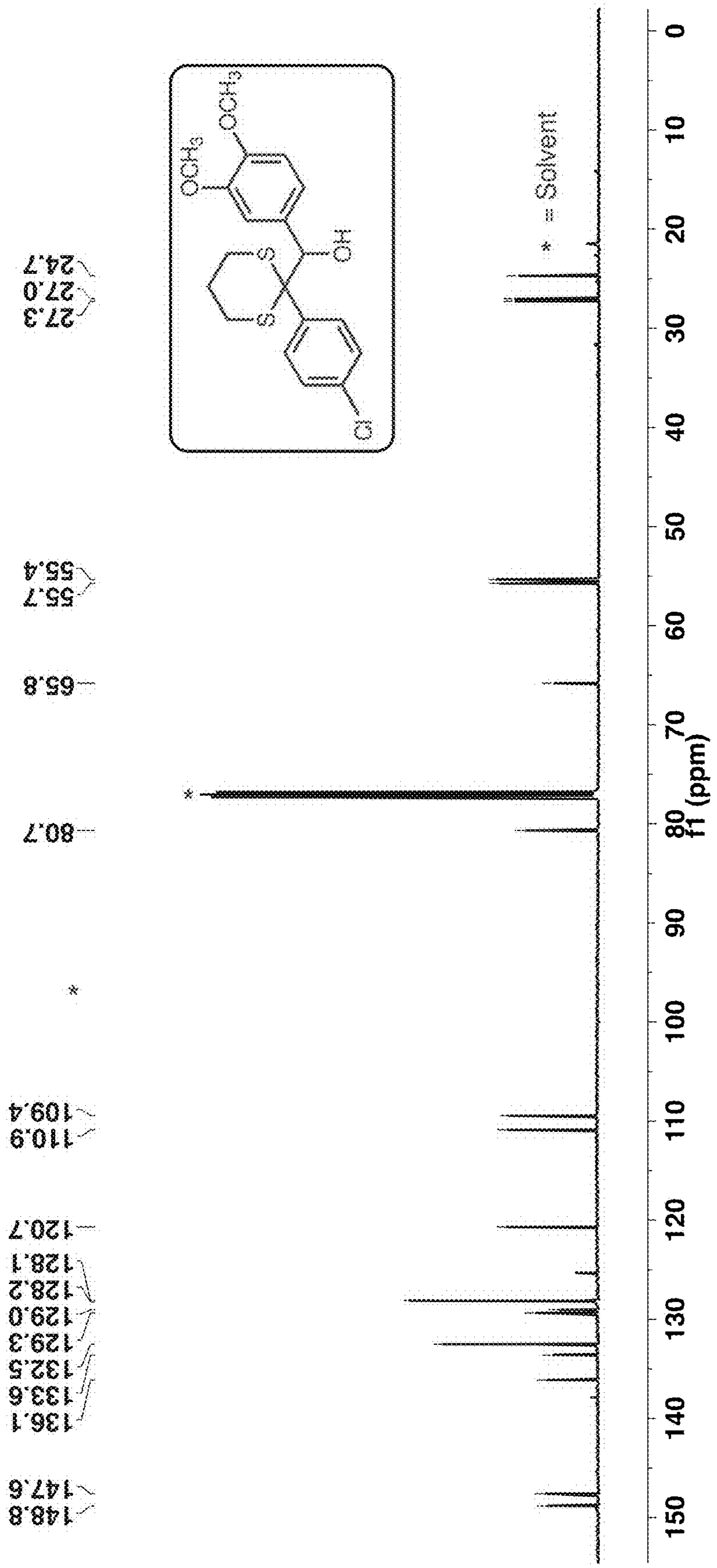

$R_f$=0.35 (30% ethyl acetate: 70% hexanes) for 5e, (Yield=65%). $^1$H NMR (500 MHz, $CDCl_3$, δ ppm) 7.67-7.63 (m, 2H), 7.32-7.15 (m, 2H), 6.71 (d, J=8.3 Hz, 1H), 6.62 (dd, J=8.3, 1.8 Hz, 1H), 6.15 (d, J=1.9 Hz, 1H), 4.97 (d, J=3.2 Hz, 1H), 3.86 (s, 3H), 3.59 (s, 3H), 2.91 (d, J=3.3 Hz, 1H), 2.80-2.58 (m, 4H), 1.95 (tdt, J=10.5, 7.4, 3.8 Hz, 2H). $^{13}$C NMR (125 MHz, $CDCl_3$, δ ppm) 148.8, 147.6, 136.1, 133.6, 132.5, 129.3, 129.0, 128.2, 128.1, 120.7, 110.9, 109.4, 80.7, 65.8, 55.7, 55.4, 27.3, 27.0, 24.7. FIGS. 22A-22B show the $^1$H NMR spectrum (FIG. 22A) and $^{13}$C NMR spectrum (FIG. 22B) of chloro derived benzyl alcohol 5e.

5f

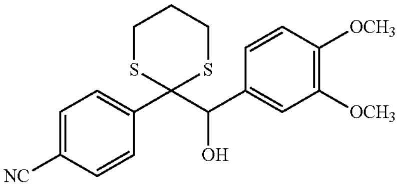

Figure 23A:
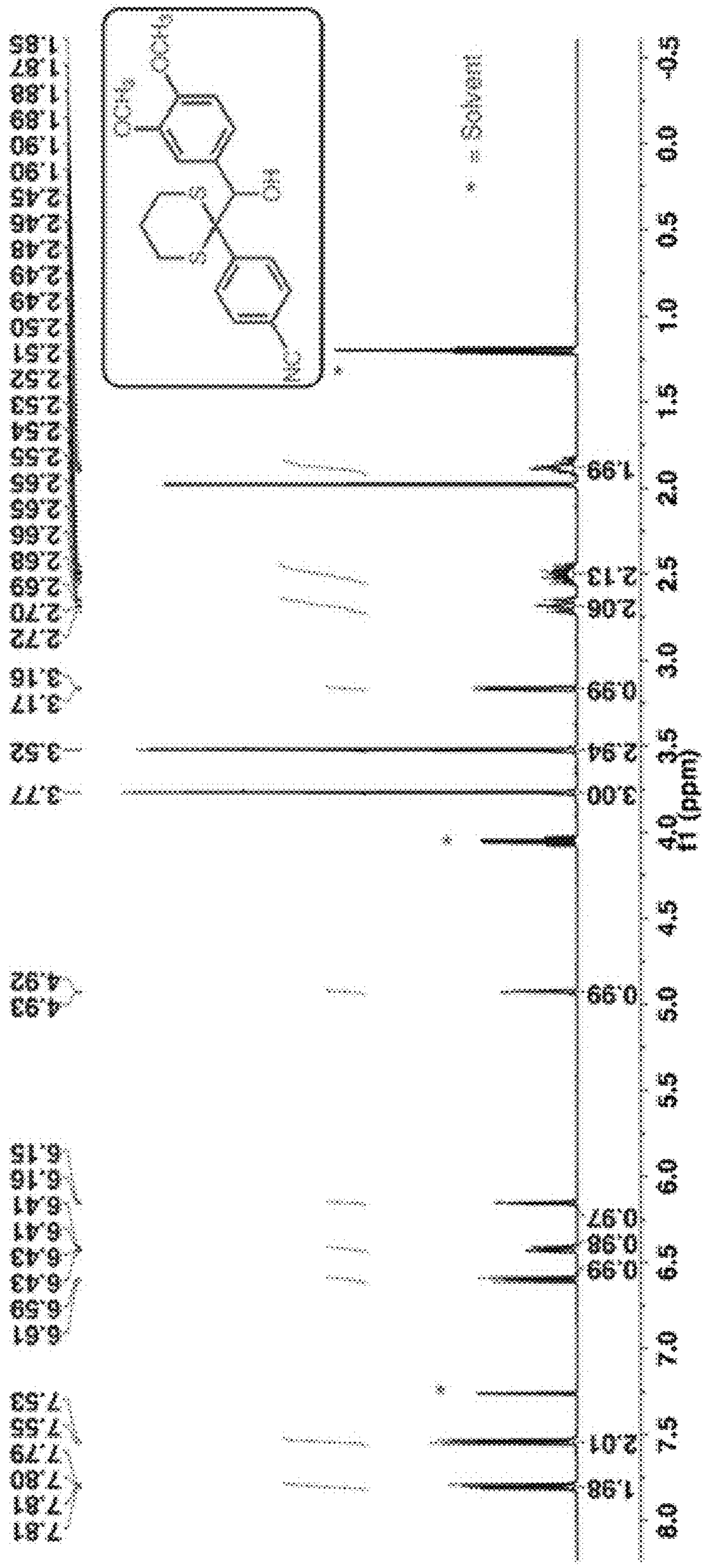
FIG. 23A-23B: $^{1}H$ NMR spectrum (FIG. 23A) and $^{13}C$ NMR spectrum (FIG. 23B) of cyano derived benzyl alcohol 5f.
Figure 23B:
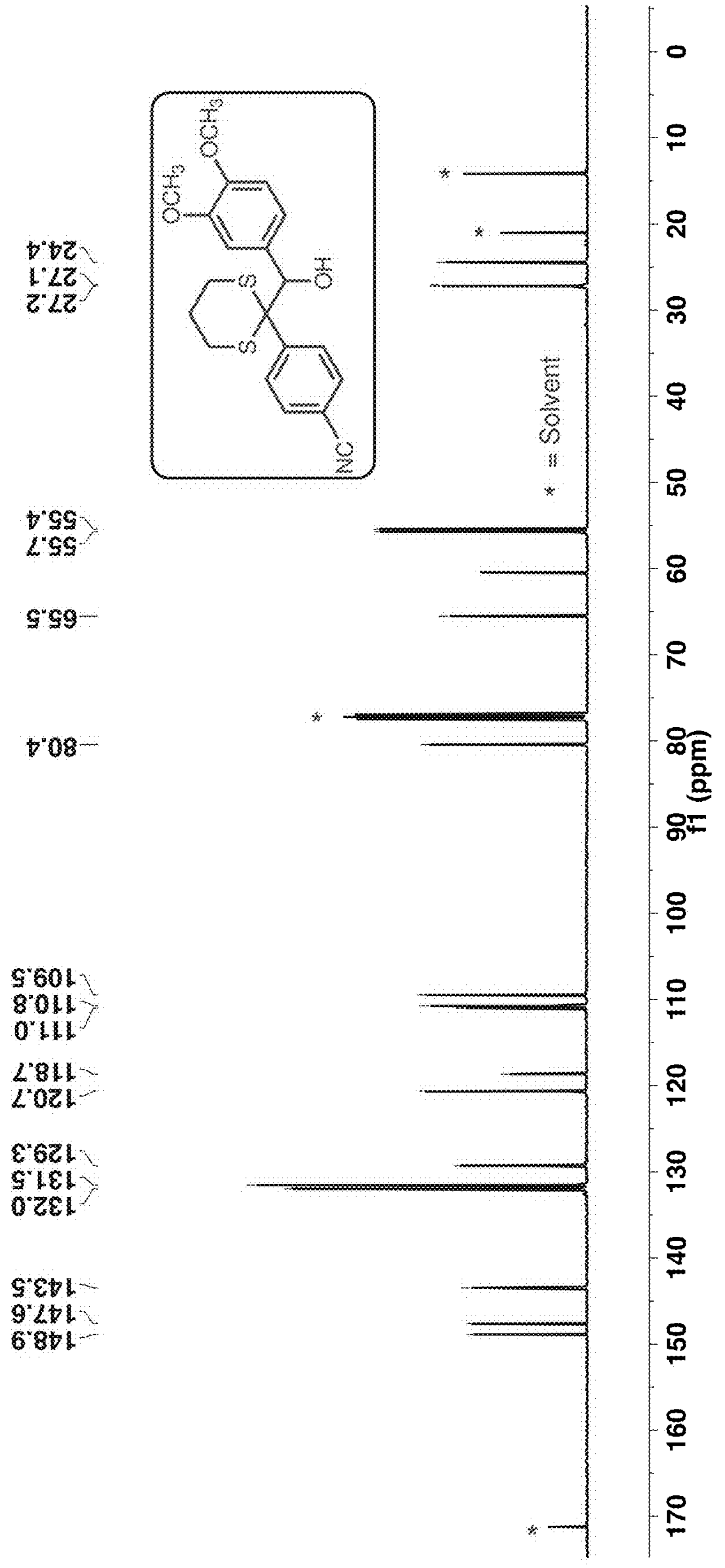

$R_f$=0.45 (20% ethyl acetate: 80% hexanes) for 5f, (Yield=50%). $^1$H NMR (500 MHz, $CDCl_3$, δ ppm) 7.83-7.78 (m, 2H), 7.54 (d, J=8.8 Hz, 2H), 6.60 (d, J=8.3 Hz, 1H), 6.42 (dd, J=8.3, 1.9 Hz, 1H), 6.15 (d, J=2.0 Hz, 1H), 4.93 (d, J=3.4 Hz, 1H), 3.77 (s, 3H), 3.52 (s, 3H), 3.17 (d, J=3.4 Hz, 1H), 2.69 (ddt, J=17.9, 14.3, 3.4 Hz, 2H), 2.56-2.44 (m, 2H), 1.93-1.84 (m, 2H). $^{13}$C NMR (125 MHz, $CDCl_3$, δ ppm) 148.9, 147.6, 143.5, 132.0, 131.5, 129.3, 120.7, 118.7, 111.0, 110.8, 109.5, 80.4, 65.5, 55.7, 55.4, 27.2, 27.1, 24.4. FIGS. 23A-23B show the $^1$H NMR spectrum (FIG. 23A) and $^{13}$C NMR spectrum (FIG. 23B) of cyano derived benzyl alcohol 5f.

5g

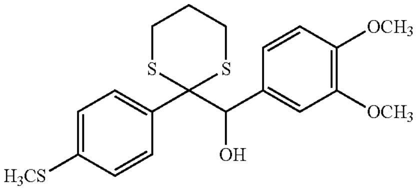

Figure 24A:
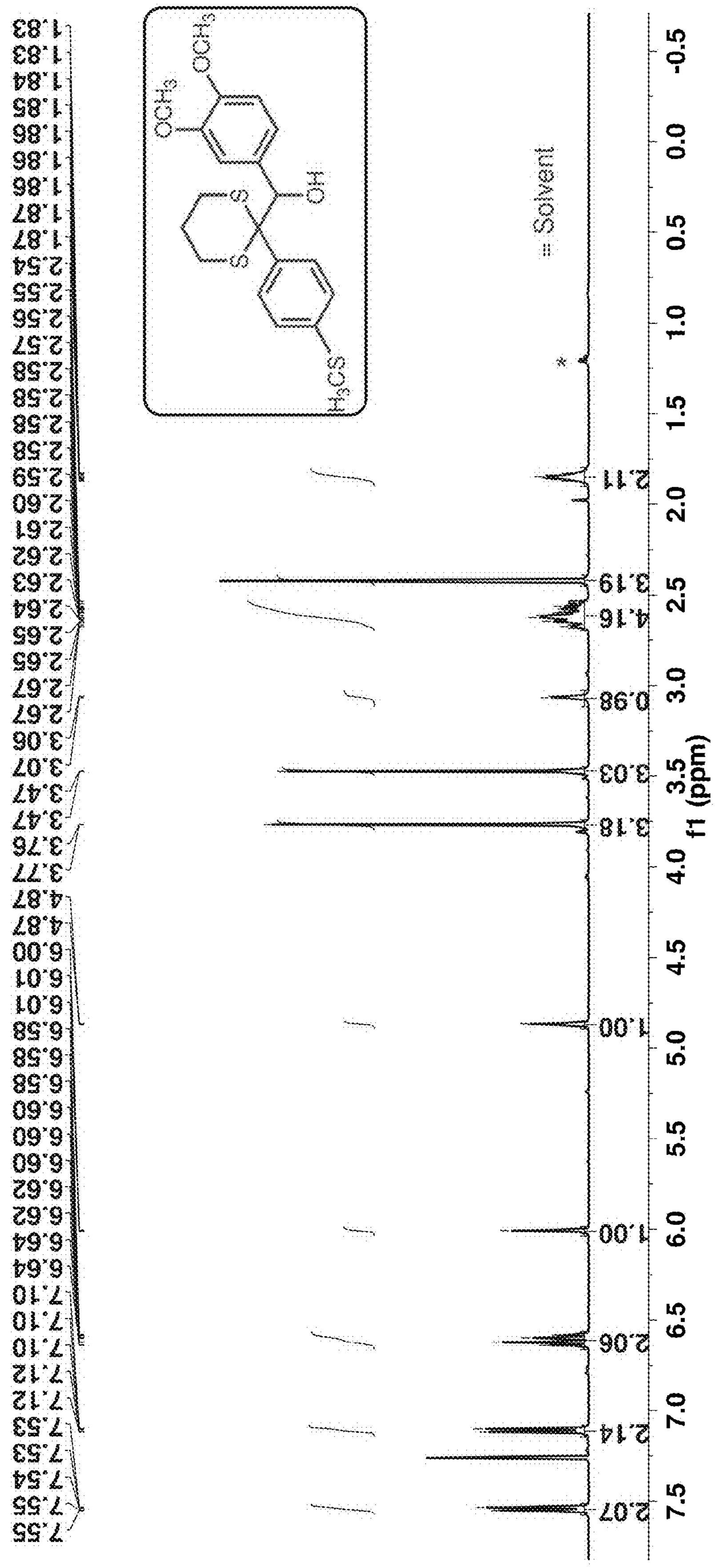
FIG. 24A-24B: $^{1}H$ NMR spectrum (FIG. 24A) and $^{13}C$ NMR spectrum (FIG. 24B) of cyano benzyl alcohol 5g.
Figure 24B:
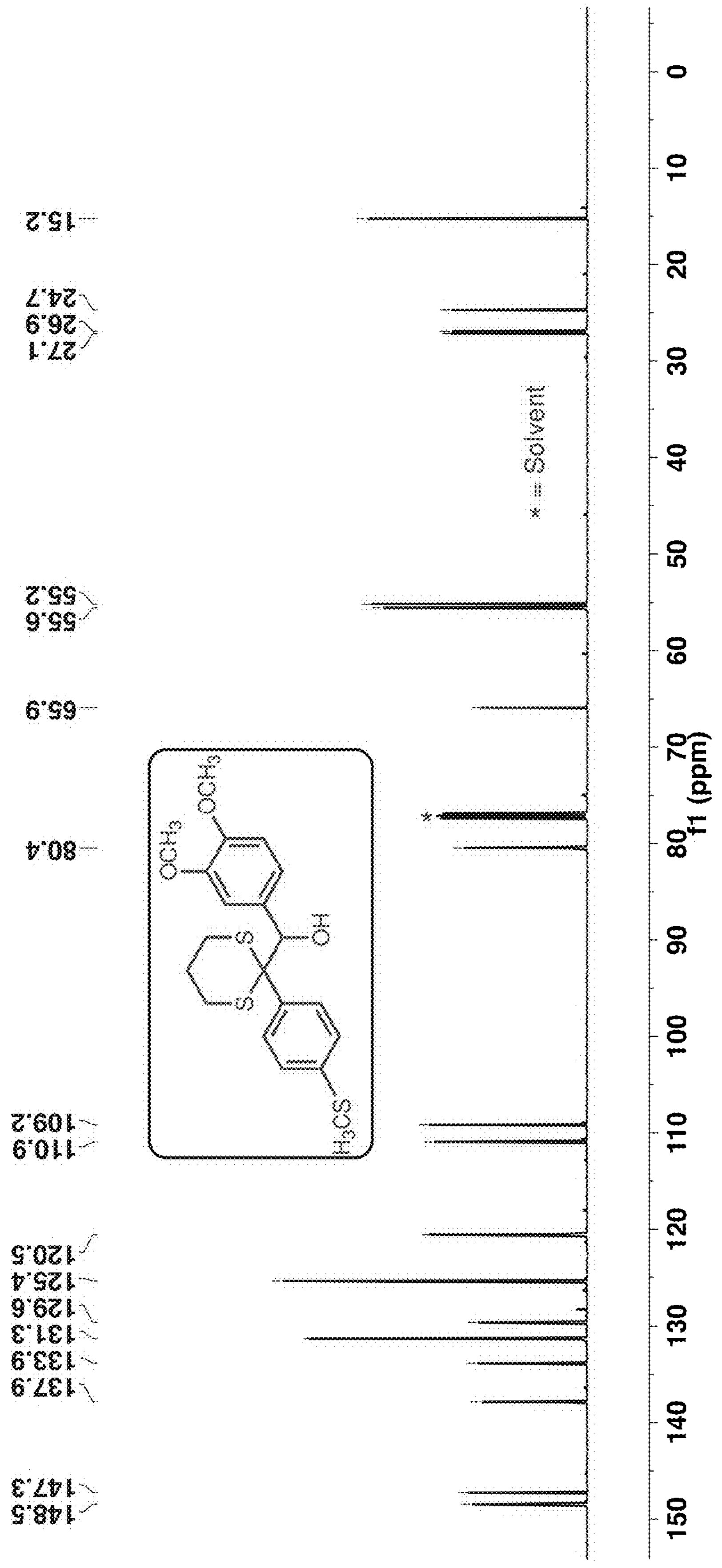

$R_f$=0.48 (20% ethyl acetate: 70% hexanes) for 5g (Yield=68%). $^1$H NMR (500 MHz, $CDCl_3$, δ ppm) 7.58-7.51 (m, 2H), 7.14-7.08 (m, 2H), 6.66-6.56 (m, 2H), 6.01 (d, J=1.8 Hz, 1H), 4.87 (d, J=2.4 Hz, 1H), 3.77 (s, 3H), 3.47 (s, 3H), 3.06 (d, J=3.3 Hz, 1H), 2.70-2.54 (m, 4H), 2.42 (s, 3H), 1.85 (tq, J=6.6, 3.3, 2.8 Hz, 2H). $^{13}$C NMR (125 MHz, $CDCl_3$, δ ppm) 148.5, 147.3, 137.9, 133.9, 131.3, 129.6, 125.4, 120.5, 110.9, 109.2, 80.4, 65.9, 55.6, 55.2, 27.1, 26.9, 24.7, 15.2. FIGS. 24A-24B show the $^{1}$H NMR spectrum (FIG. 24A) and $^{13}$C NMR spectrum (FIG. 24B) of cyano benzyl alcohol 5g.

Synthesis of Benzoin Derivatives 1a-1g

The synthesis of benzoin derivatives 1a-1g is depicted in FIG. 10.

Deprotection of dithiane protecting group was carried out. To a solution of hydroxy derivative 5 (1.0 equiv) in EtOH (30 mL), freshly prepared catalyst (1.4 equiv iodine adsorbed on 7.5 equiv $Al_2O_3$) was added and the mixture and was stirred for 20 minutes at room temperature. Water (3 mL) was added to the reaction mixture and continued stirring for ~4 h. After the completion of reaction, the mixture was filtered through celite bed and washed with ethyl acetate (2×20 mL). The organic layers were washed with saturated sodium bisulfate solution (10 mL) and ethyl acetate (10 mL). Further the combined organic layer was dried over anhyd. $Na_2SO_4$, filtered, and the solvent was removed under reduced pressure. The obtained crude product was purified by combiflash using hexanes:ethyl acetate mixture.

1a

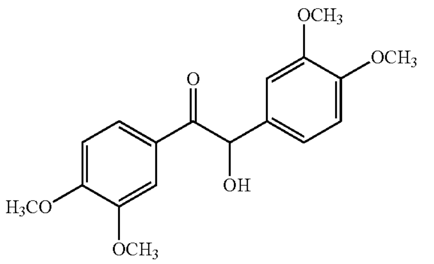

Figure 25A:
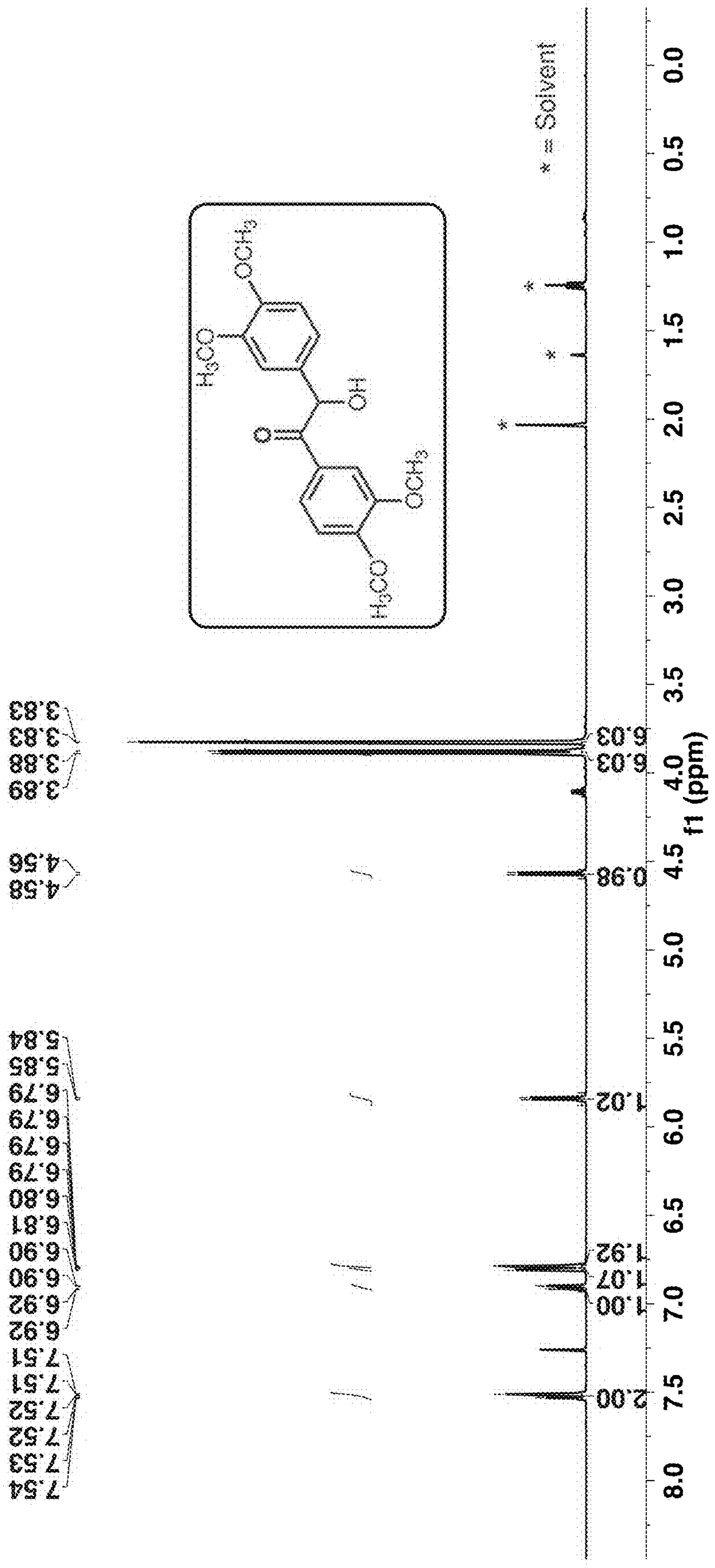
Figure 25B:
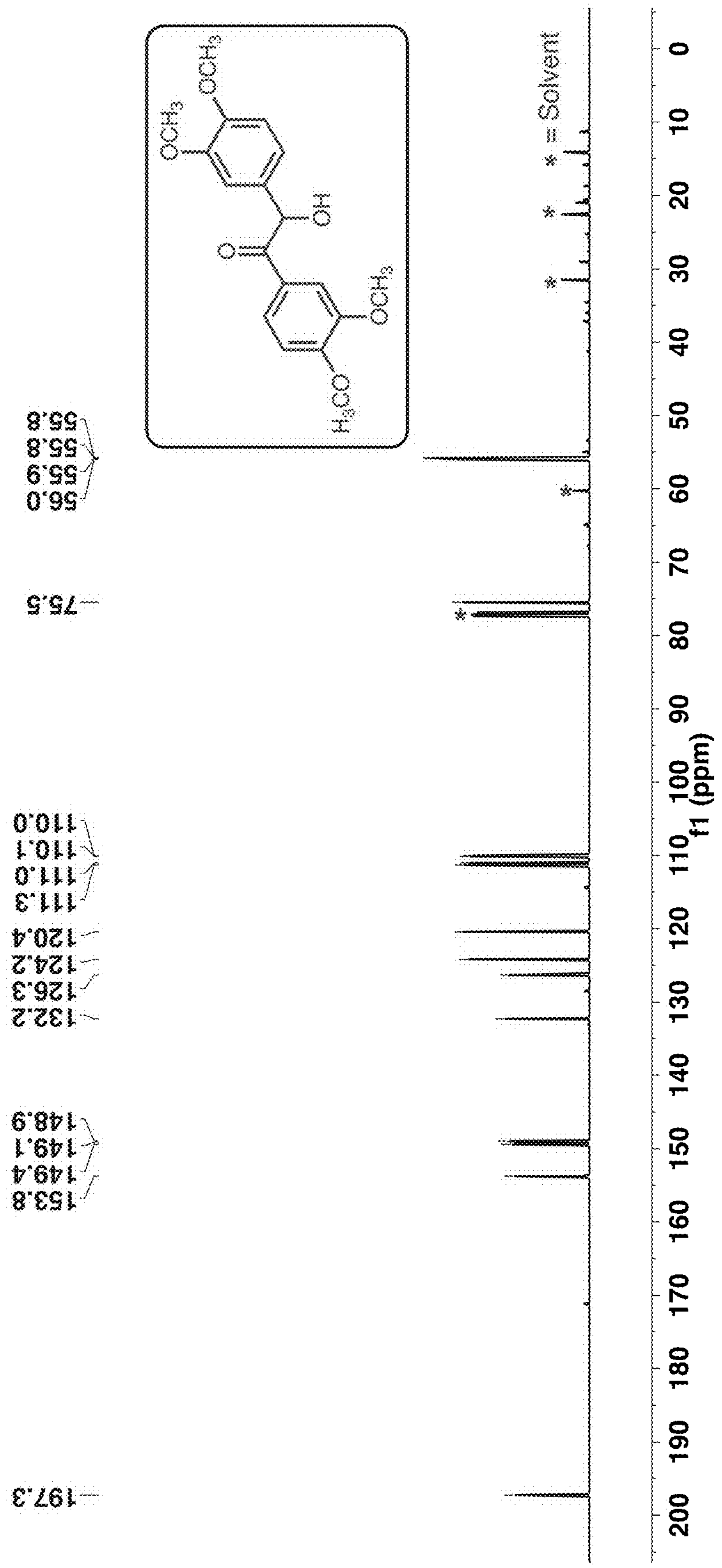

$R_f$=0.45 (50% ethyl acetate: 50% hexanes) for 1a, (Yield=65%). $^{1}$H NMR (500 MHz, $CDCl_3$, δ ppm) 7.55-7.49 (m, 2H), 6.91 (dd, J=8.2, 2.1 Hz, 1H), 6.81 (d, J=3.9 Hz, 1H), 6.79 (dd, J=3.1, 0.9 Hz, 2H), 5.84 (d, J=6.0 Hz, 1H), 4.57 (d, J=6.0 Hz, 1H), 3.88 (d, J=7.4 Hz, 6H), 3.83 (d, J=1.4 Hz, 6H). $^{13}$C NMR (125 MHz, $CDCl_3$, δ ppm) 197.3, 153.8, 149.4, 149.1, 148.9, 132.2, 126.3, 124.2, 120.4, 111.3, 111.0, 110.1, 110.0, 75.5, 56.0, 55.9, 55.8, 55.8. FIGS. 25A-25B show the $^{1}$H NMR spectrum (FIG. 25A) and $^{13}$C NMR spectrum (FIG. 25B) of bis-(dimethoxy)-phenylbenzoin 1a.

1b

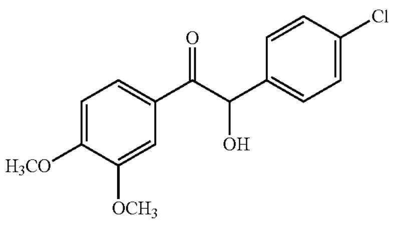

Figure 26A:
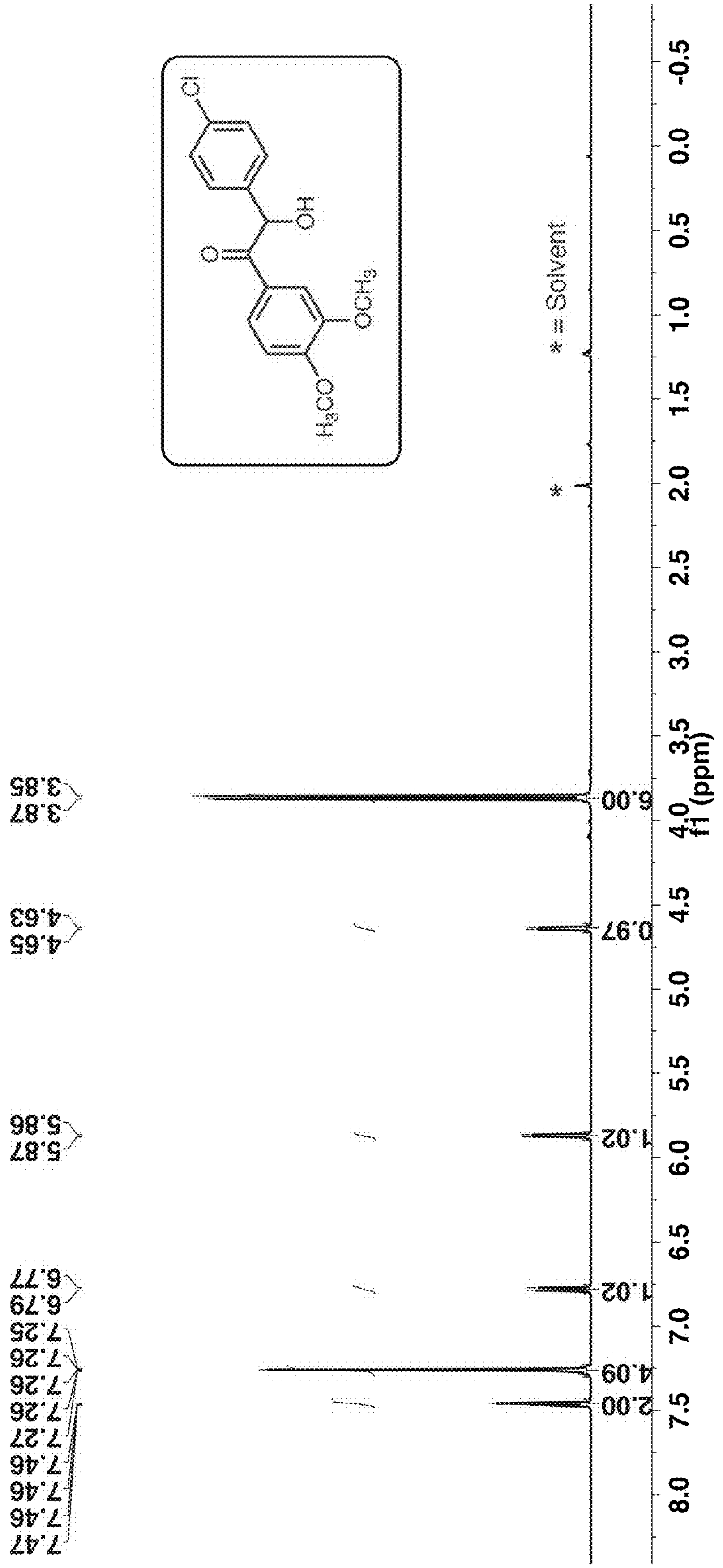
FIG. 26A-26B: $^{1}H$ NMR spectrum (FIG. 26A) and $^{13}C$ NMR spectrum (FIG. 26B) of para-chlorobenzyl-(dimethoxy)-benzoin 1b.
Figure 26B:
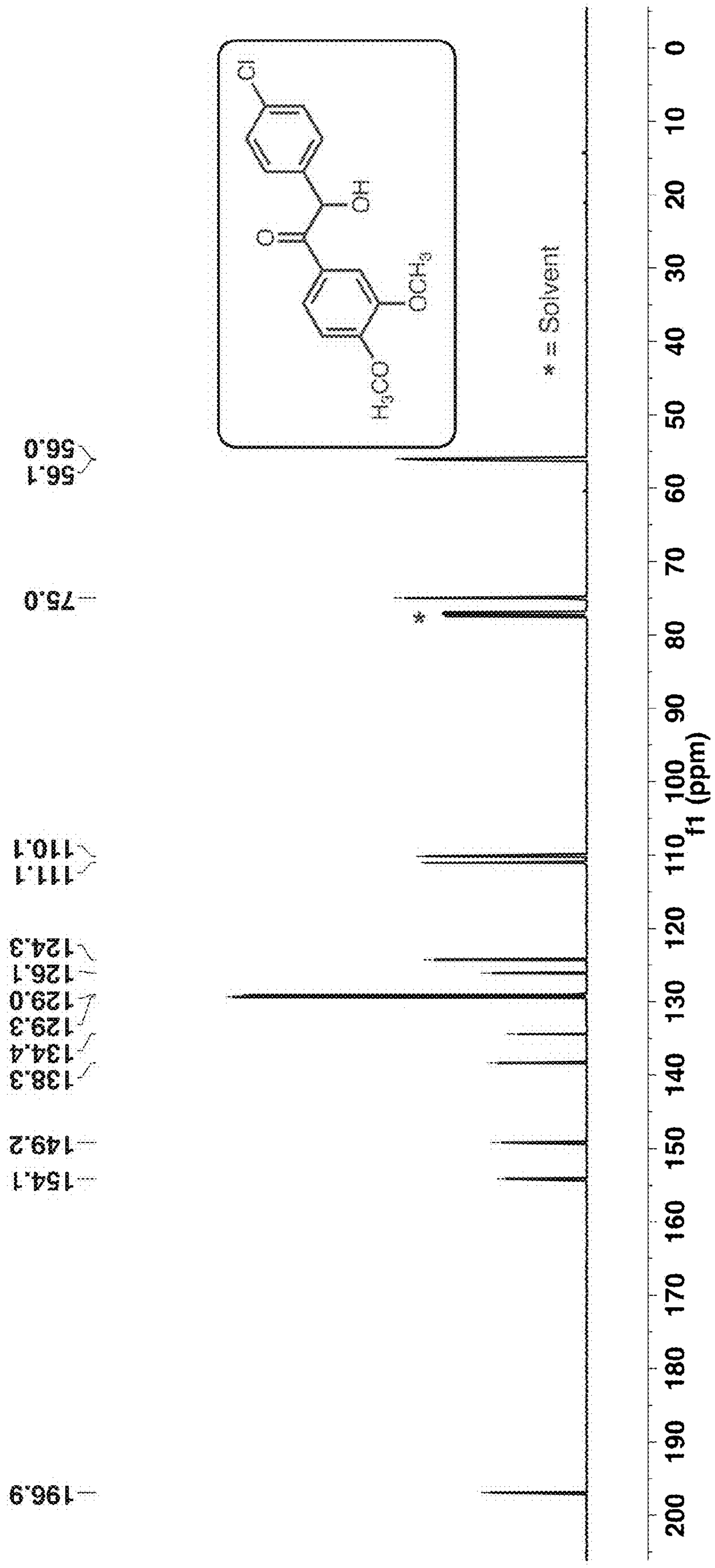

$R_f$=0.40 (50% ethyl acetate: 50% hexanes) for 1b, (Yield=68%). $^{1}$H NMR (500 MHz, $CDCl_3$, δ ppm) 7.48-7.43 (m, 2H), 7.26 (d, J=1.0 Hz, 4H), 6.78 (d, J=9.0 Hz, 1H), 5.87 (d, J=6.0 Hz, 1H), 4.64 (d, J=6.0 Hz, 1H), 3.87 (d, J=8.3 Hz, 6H) 3.85 (d, J=8.3 Hz, 6H). $^{13}$C NMR (125 MHz, $CDCl_3$, δ ppm) 196.9, 154.1, 149.2, 138.3, 134.4, 129.3, 129.0, 126.1, 124.3, 111.1, 110.1, 75.0, 56.1, 56.0. FIGS. 26A-26B show the $^{1}$H NMR spectrum (FIG. 26A) and $^{13}$C NMR spectrum (FIG. 26B) of para-chlorobenzyl-(dimethoxy)-benzoin 1b.

1c

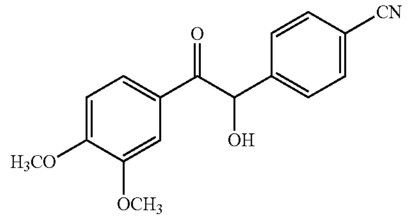

Figure 27A:
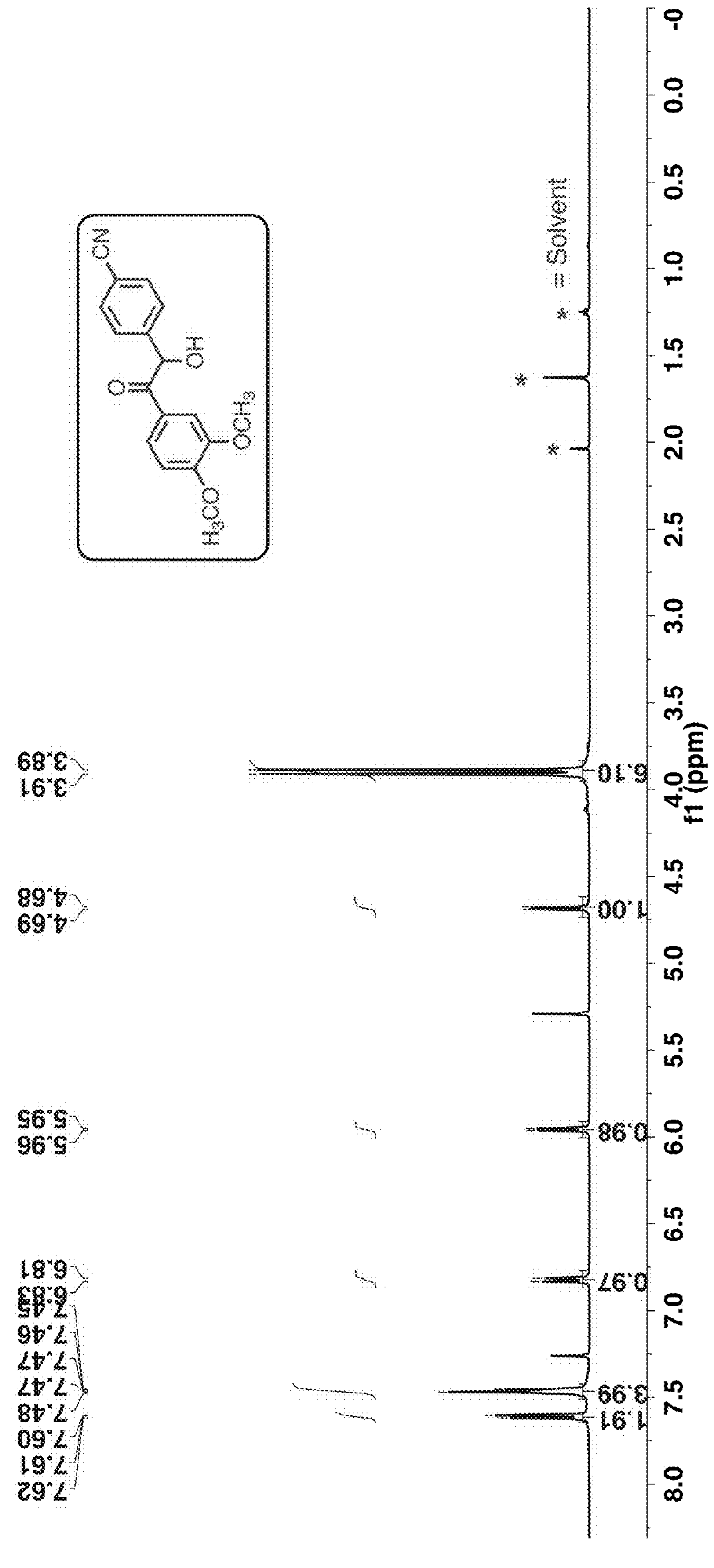
FIG. 27A-27B: $^{1}H$ NMR spectrum (FIG. 27A) and $^{13}C$ NMR spectrum (FIG. 27B) of para-cyanobenzyl-(dimethoxy)-benzoin 1c.
Figure 27B:
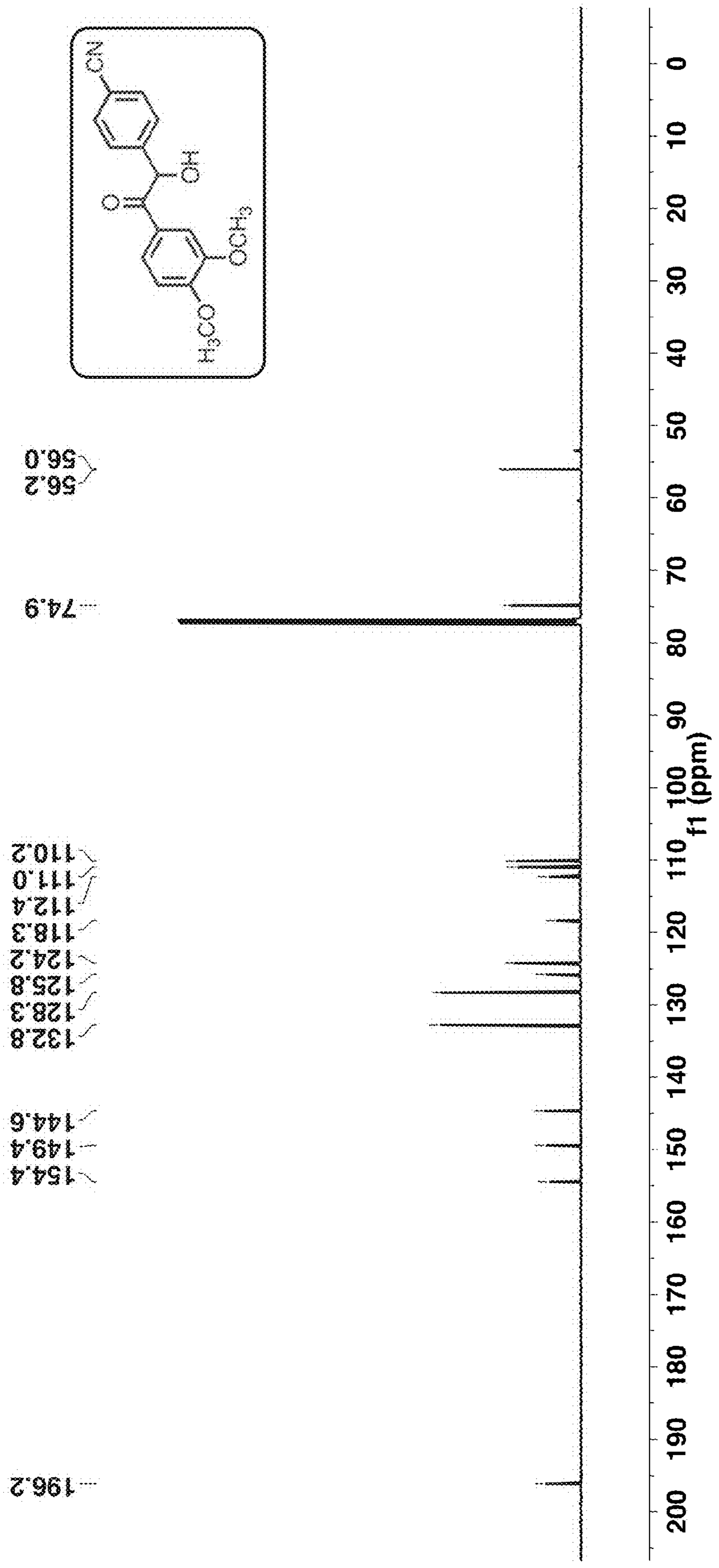

$R_f$=0.34 (50% ethyl acetate: 50% hexanes) for 1c, (Yield=55%). $^{1}$H NMR (500 MHz, $CDCl_3$, δ ppm) 7.65-7.58 (m, 2H), 7.47 (td, J=5.4, 1.9 Hz, 4H), 6.82 (d, J=9.0 Hz, 1H), 5.96 (d, J=6.0 Hz, 1H), 4.68 (d, J=6.2 Hz, 1H), 3.90 (d, J=11.6 Hz, 6H). $^{13}$C NMR (125 MHz, $CDCl_3$, δ ppm) 196.2, 154.4, 149.4, 144.6, 132.8, 128.3, 125.8, 124.2, 118.3, 112.4, 111.0, 110.2, 74.9, 56.2, 56.0. FIGS. 27A-27B show the $^{1}$H NMR spectrum (FIG. 27A) and $^{13}$C NMR spectrum (FIG. 27B) of para-cyanobenzyl-(dimethoxy)-benzoin 1c.

1d

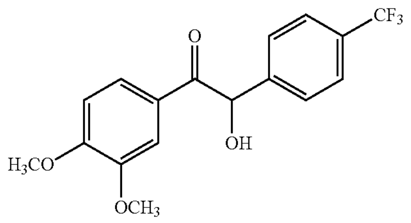

Figure 28A:
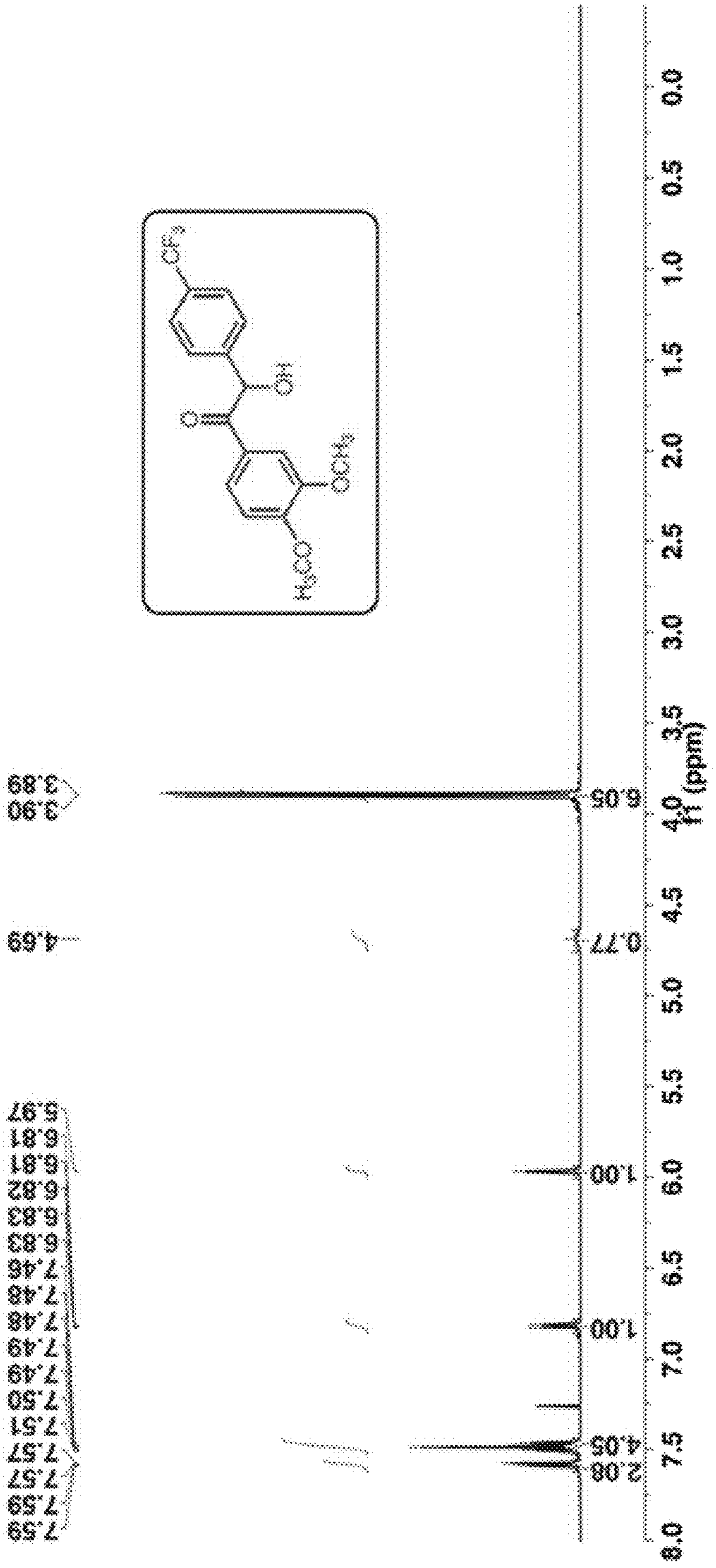
FIG. 28A-28B: $^{1}H$ NMR spectrum (FIG. 28A) and $^{13}C$ NMR spectrum (FIG. 28B) of para-trifluoromethylbenzyl-(dimethoxy)-benzoin 1d.
Figure 28B:
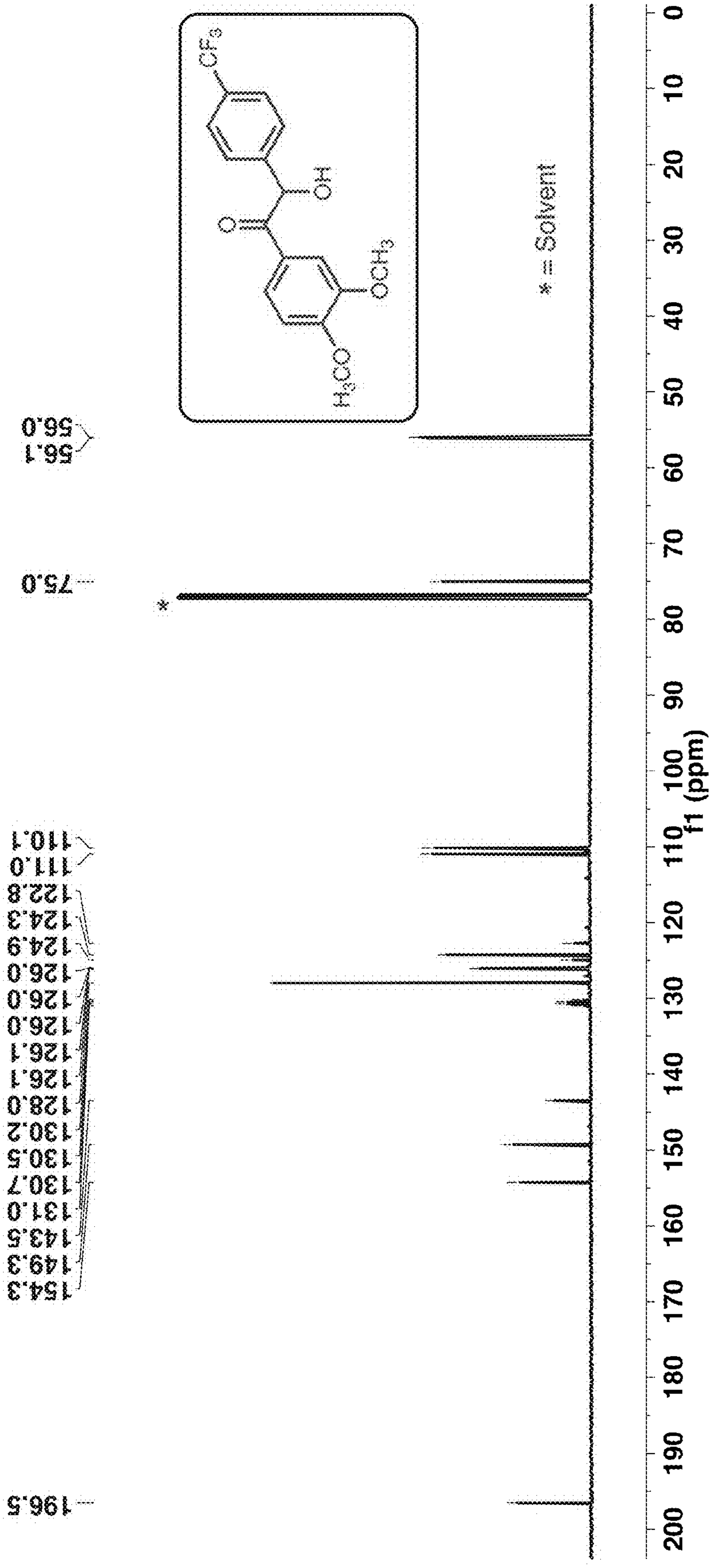

$R_f$=0.30 (50% ethyl acetate: 50% hexanes) for 1d, (Yield=68%). $^{1}$H NMR (500 MHz, $CDCl_3$, δ ppm) 7.58 (dd, J=7.6, 1.2 Hz, 2H), 7.53-7.44 (m, 4H), 6.86-6.78 (m, 1H), 5.97 (s, 1H), 4.69 (s, 1H), 3.90 (d, J=9.2 Hz, 6H). $^{13}$C NMR (125 MHz, $CDCl_3$, δ ppm) 196.5, 154.3, 149.2, 143.5, 130.9, 130.7, 130.4, 130.2, 127.9, 126.1, 126.0, 126.0, 126.0, 125.9, 124.9, 124.2, 122.7, 110.9, 110.1, 75.0, 56.1, 55.9. FIGS. 28A-28B show the $^{1}$H NMR spectrum (FIG. 28A) and $^{13}$C NMR spectrum (FIG. 28B) of para-trifluoromethylbenzyl-(dimethoxy)-benzoin 1d.

1e

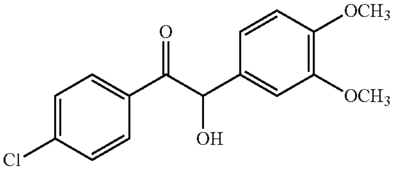

Figure 29A:
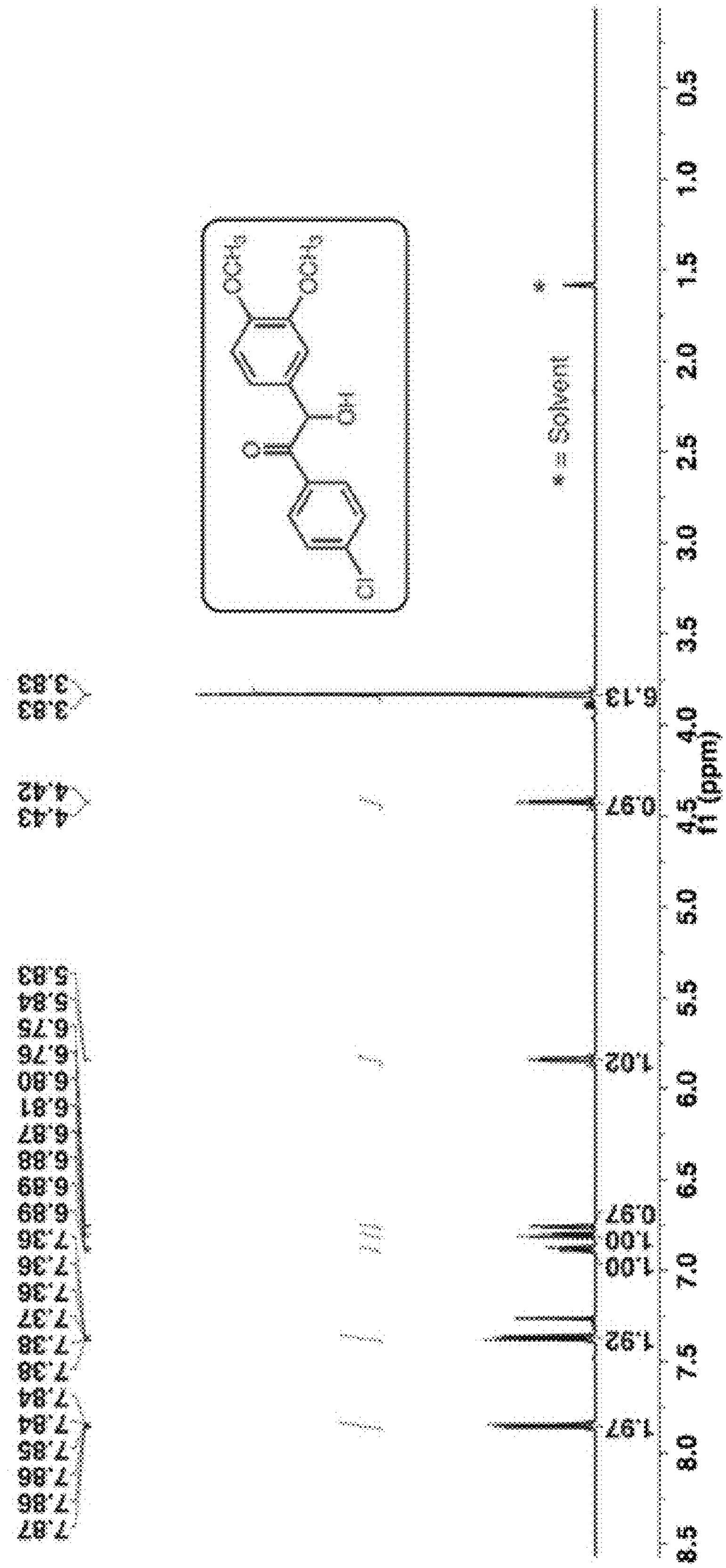
FIG. 29A-29B: $^{1}H$ NMR spectrum (FIG. 29A) and $^{13}C$ NMR spectrum (FIG. 29B) of para-chlorobenzoyl-(dimethoxy)-benzoin 1e.
Figure 29B:
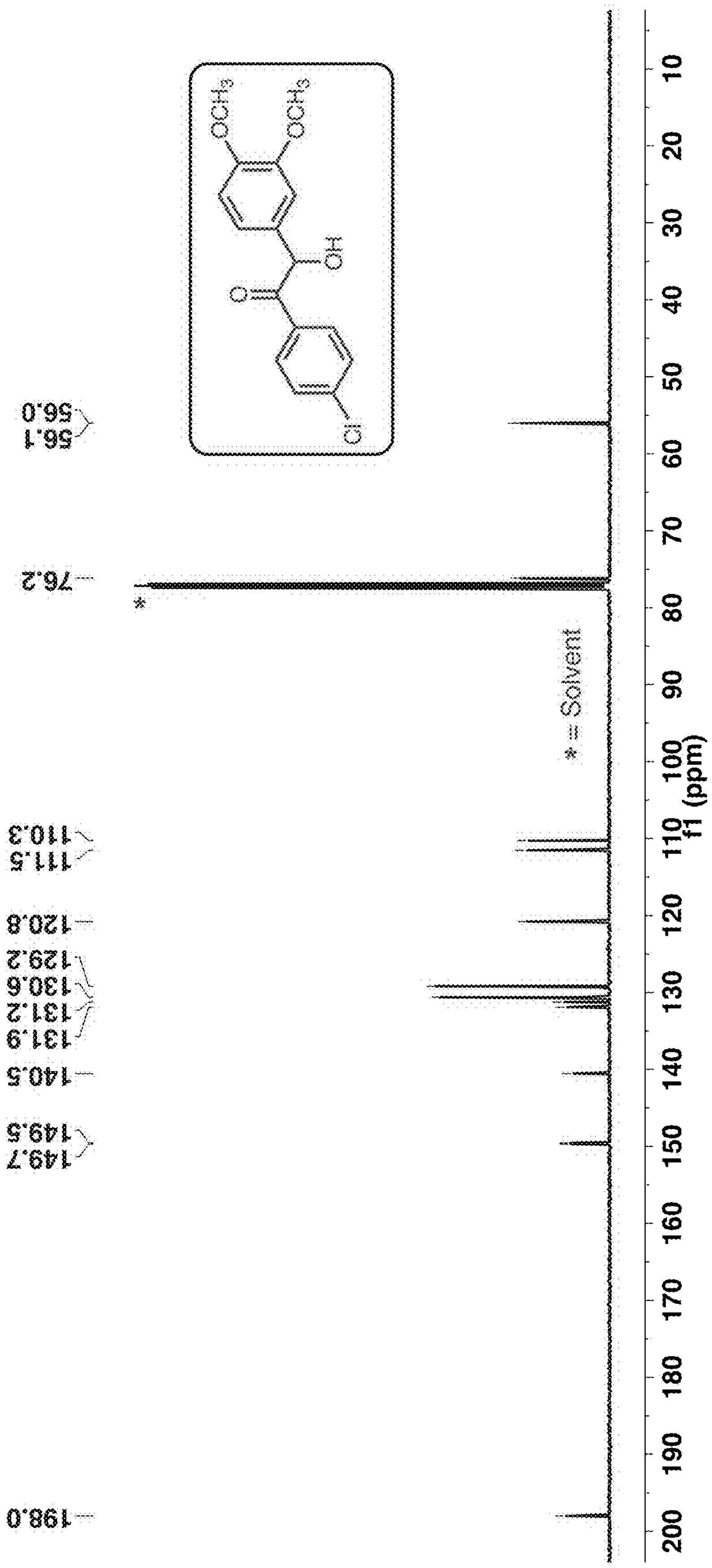

$R_f$=0.48 (50% ethyl acetate: 50% hexanes) for 1e, (Yield=56%). $^{1}$H NMR (500 MHz, $CDCl_3$, δ ppm) 7.90-7.85 (m, 2H), 7.42-7.37 (m, 2H), 6.91 (dd, J=8.2, 2.1 Hz, 1H), 6.83 (d, J=8.2 Hz, 1H), 6.78 (d, J=2.1 Hz, 1H), 5.86 (d, J=5.9 Hz, 1H), 4.45 (d, J=5.9 Hz, 1H), 3.83 (s, 3H), 3.83 (s, 3H). $^{13}$C NMR (125 MHz, $CDCl_3$, δ ppm) 198.0, 149.7, 149.5, 140.5, 131.9, 131.2, 130.6, 129.2, 120.8, 111.5, 110.3, 76.3, 56.1, 56.0. FIG. 29A-29B show the $^{1}$H NMR spectrum (FIG. 29A) and $^{13}$C NMR spectrum (FIG. 29B) of para-chlorobenzoyl-(dimethoxy)-benzoin 1e.

1g

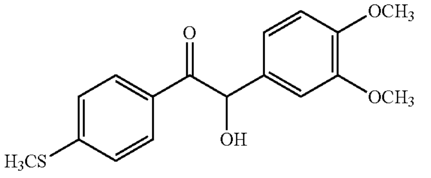

Figure 30A:
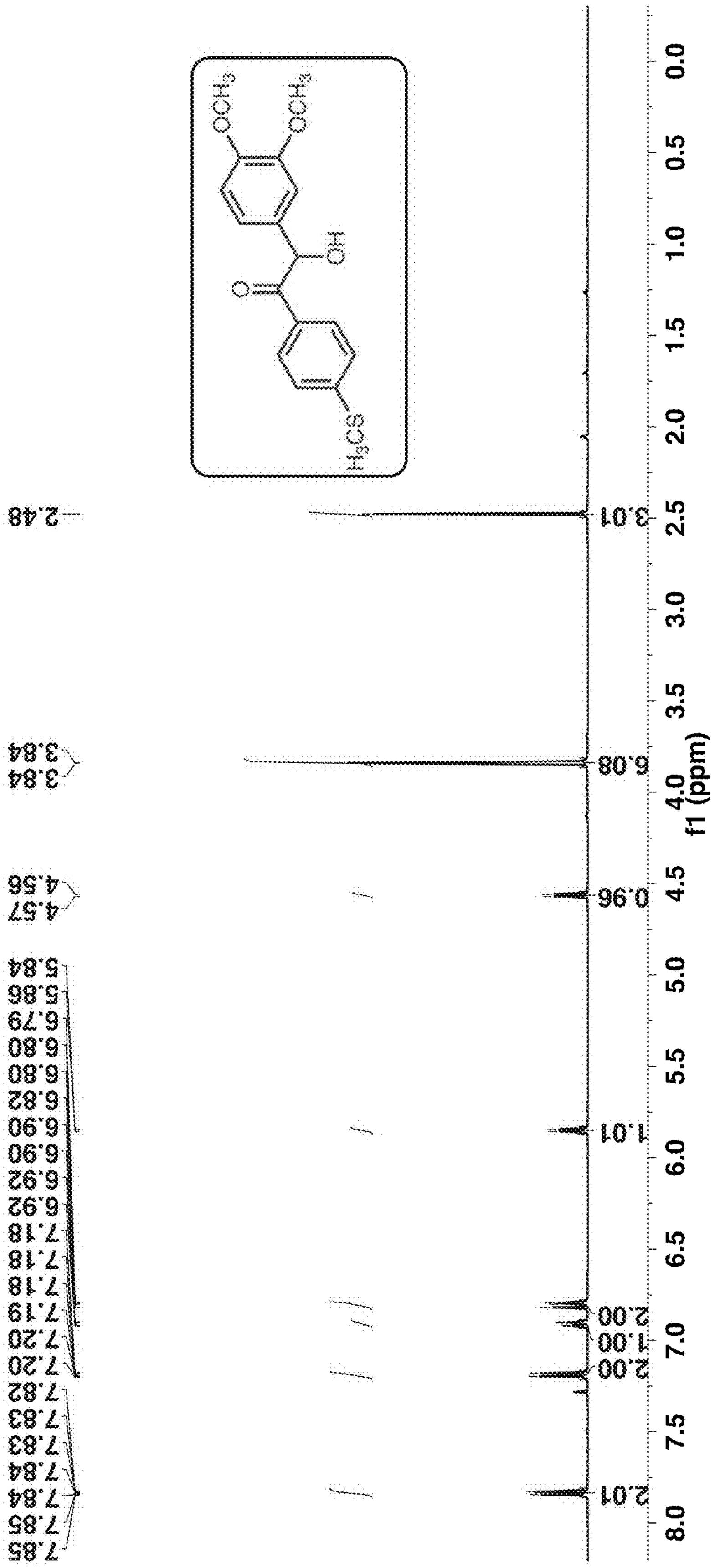
FIG. 30A-30B: $^{1}H$ NMR spectrum (FIG. 30A) and $^{13}C$ NMR spectrum (FIG. 30B) of para-thiomethylbenzoyl-(dimethoxy)-benzoin 1g.
Figure 30B:
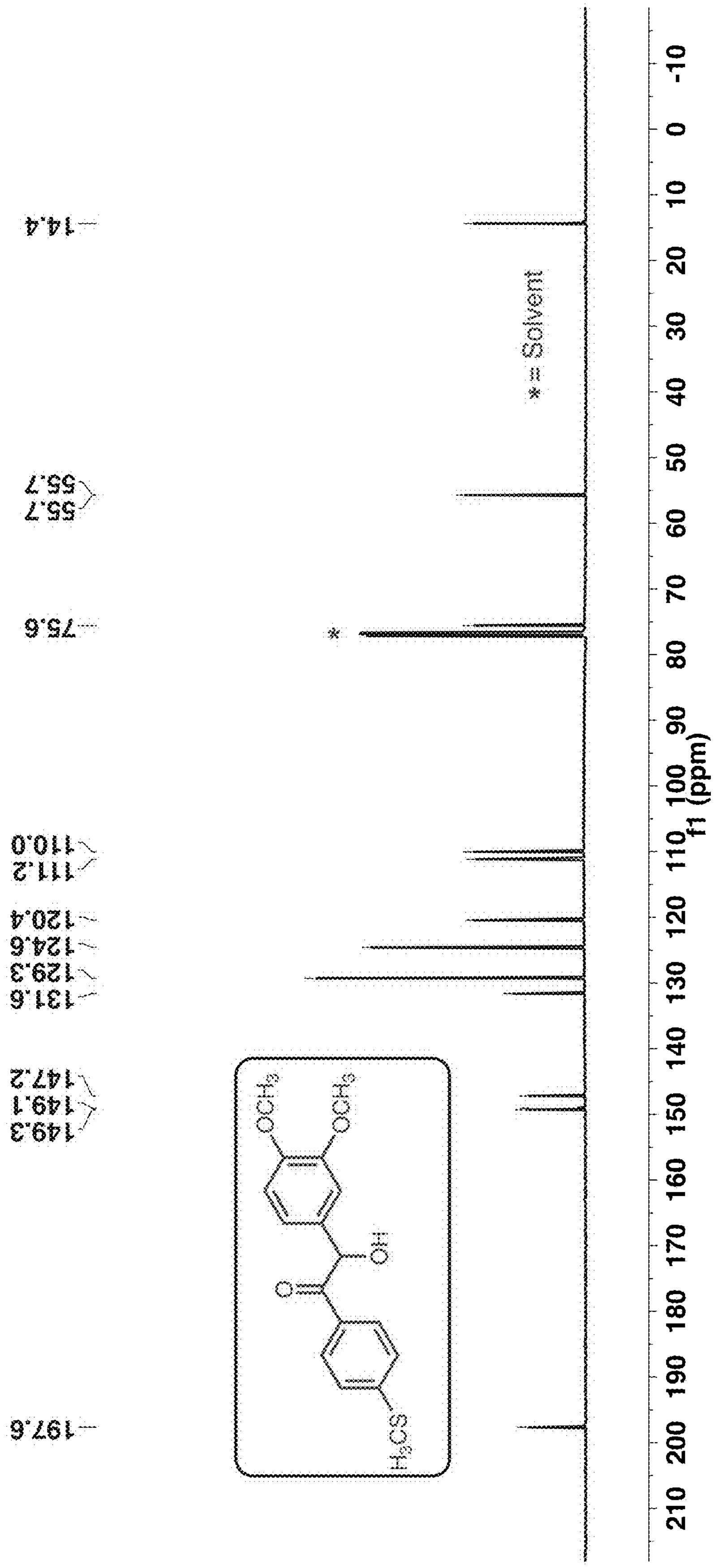

$R_f$=0.30 (50% ethyl acetate: 50% hexanes) for 1g, (Yield=58%). $^{1}H$ NMR (500 MHz, $CDCl_3$, δ ppm) 7.86-7.81 (m, 2H), 7.22-7.16 (m, 2H), 6.91 (dd, J=8.2, 2.1 Hz, 1H), 6.83-6.78 (m, 2H), 5.85 (d, J=5.9 Hz, 1H), 4.56 (d, J=6.0 Hz, 1H), 3.84 (s, 3H), 3.84 (s, 3H) 2.48 (s, 3H). $^{13}C$ NMR (125 MHz, $CDCl_3$, δ ppm) 197.6, 149.3, 149.1, 147.2, 131.6, 129.3, 124.6, 120.4, 111.2, 110.0, 75.6, 55.7, 55.7, 14.4. FIGS. 30A-30B show the $^{1}H$ NMR spectrum (FIG. 30A) and $^{13}C$ NMR spectrum (FIG. 30B) of para-thiomethylbenzoyl-(dimethoxy)-benzoin 1g.

Photophysical Studies

Photopolymerization of Methylmethacrylate 6 with Benzoin Photoinitiators

Figure 6:
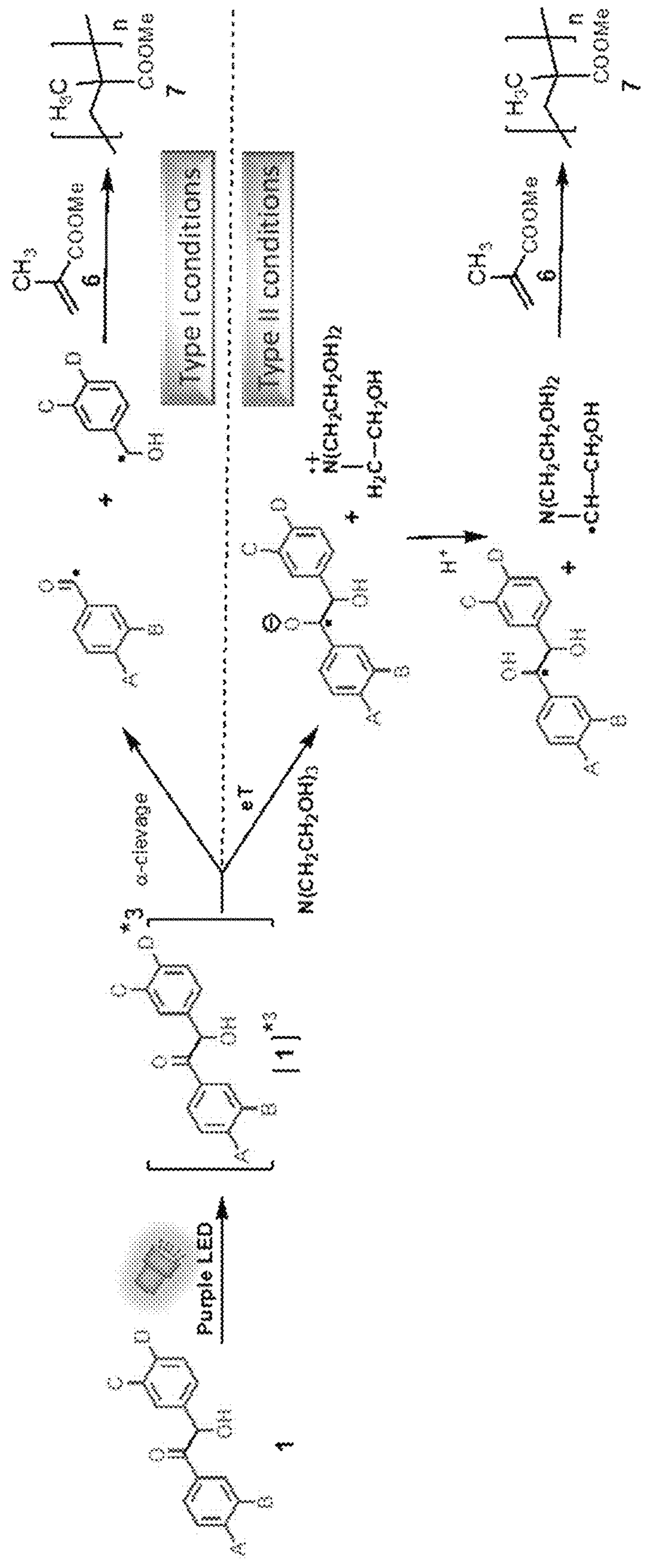
FIG. 6: Scheme 4: Mechanism of photopolymerization by biomass derived benzoin type I and type II process.

The photopolymerization of methylmethacrylate 6 with biomass derived benzoin photoinitiators is depicted in FIG. 6.

Freshly distilled methyl methacrylate (MMA) 6, benzoin photoinitiators 1a-1h, and co-initiator (Tables 2-3) were dissolved in MeCN. The solutions were taken in a sealed pyrex test tubes and was purged with $N_2$ to remove dissolved oxygen. The resulting mixture was irradiated with purple LED (strip winded around glass jar) for 4 h. After the photopolymerization polymethylmethacrylate (PMMA) 7 was crashed out by addition of ~30 mL of cold methanol. Polymers were separated out by filtration and vacuum dried at ~35° C. for ~24 h.

Table 1 above displays GPC analysis of biomass derived photoinitiators for methacrylate polymerization without co-initiator.

Figure 11:
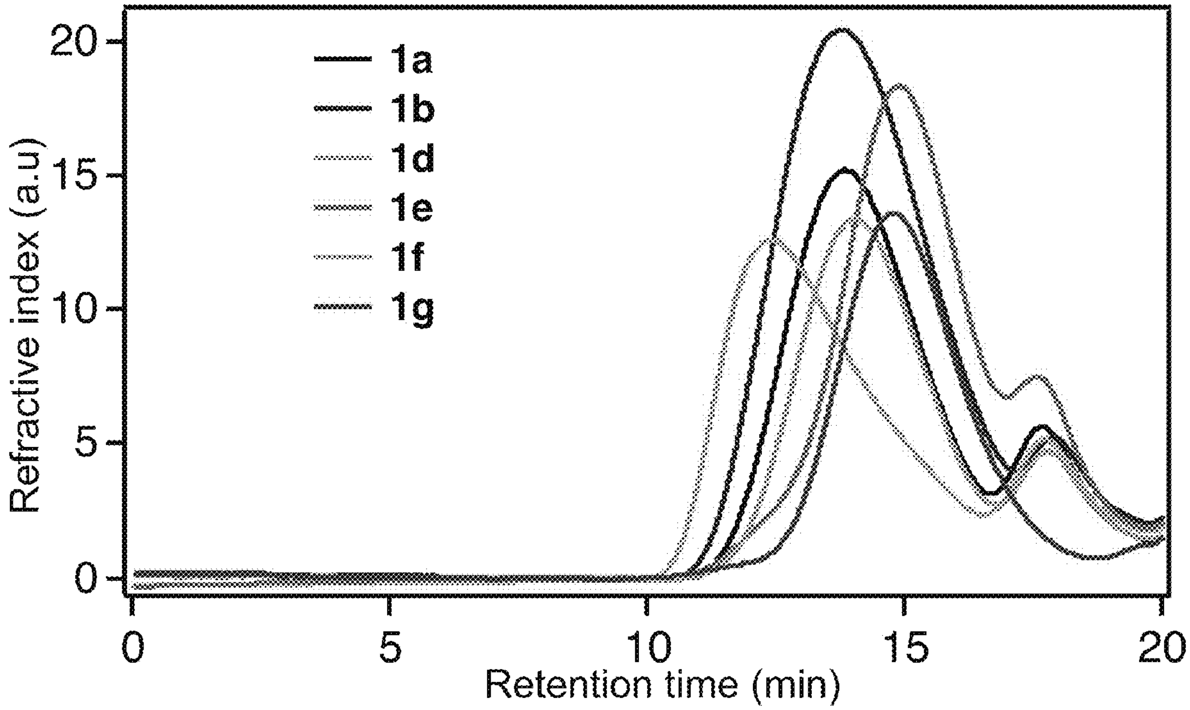
FIG. 11: GPC traces of photopolymerization of methyl methacrylate 6 by PI 1a-1h with same optical density without co-initiator.

FIG. 11 shows GPC trace of methylmethacrylate 6 by PI's 1a-1g with the same optical density (OD) at ~390 nm.

Table 2 above displays GPC analysis of biomass derived photoinitiators for acrylate polymerization with co-initiator at the same optical density.

Figure 12:
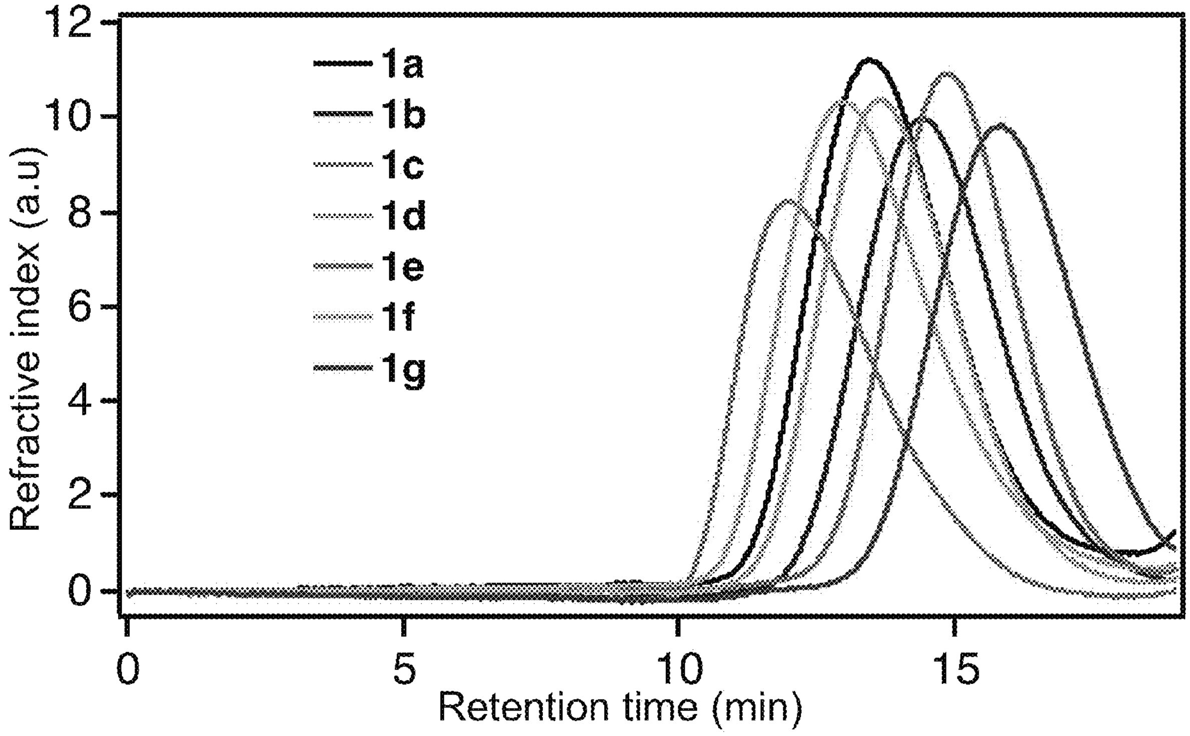
FIG. 12: GPC traces of photopolymerization of methyl methacrylate 6 by PI 1a-1h with same optical density with co-initiator.

FIG. 12 shows GPC trace of methylmethacrylate 6 by PI's 1a-g with the same optical density (OD) at ~390 nm.

Table 3 above displays GPC analysis of biomass derived photoinitiators for acrylate polymerization at the same concentration in the presence of triethanol amine as a co-initiator.

Figure 13:
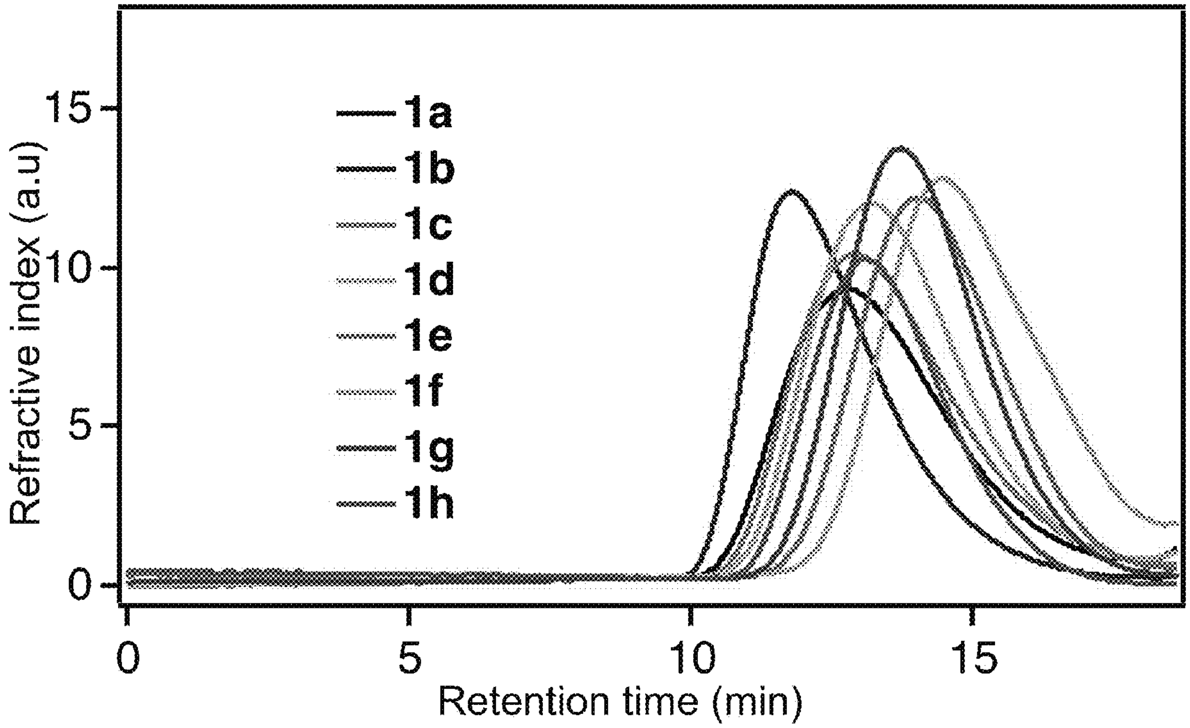
FIG. 13: GPC traces of photopolymerization of methyl methacrylate 6 by same concentration PI 1a-1h along with co-initiator.

FIG. 13 shows GPC trace of photopolymerization of methyl methacrylate 6 by the same concentration PI's 1a-1h along with co-initiator.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula Bz-1:

Formula Bz-1

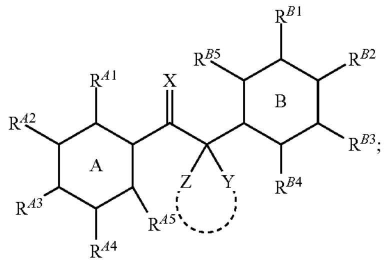

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom; and substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes;

provided that one of A or B has two methoxy substituents.

2. The composition of claim 1, wherein the composition comprises bis-(dimethoxy)-benzoin 1a, para-chlorobenzyl-(dimethoxy)-benzoin 1b, para-cyanobenzyl-(dimethoxy)-benzoin 1c, para-trifluoromethylbenzyl-(dimethoxy)-benzoin 1d, para-chlorobenzoyl-(dimethoxy)-benzoin 1e, para-thiomethylbenzoyl-(dimethoxy)-benzoin 1f, para-thiomethylbenzoyl-(dimethoxy)-benzoin 1g, para-fluorobenzyl-(dimethoxy)-benzoin 1i, or para-fluorobenzyl-(dimethoxy)-benzoin 1j:

1a

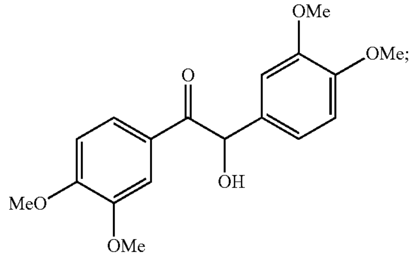

-continued

1b

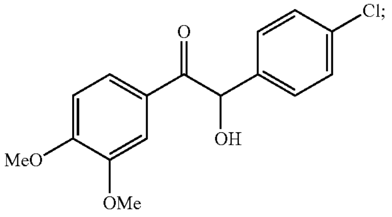

1c

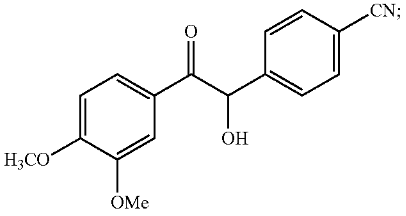

1d

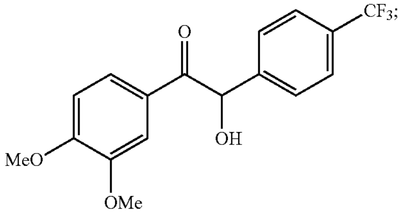

1e

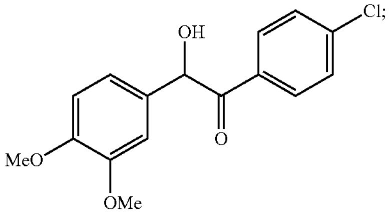

1f

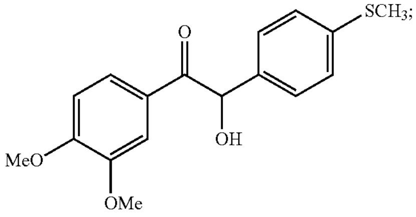

1g

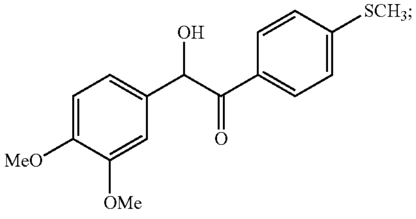

1i

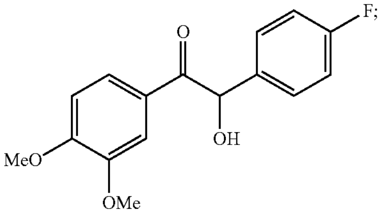

or

-continued

1j

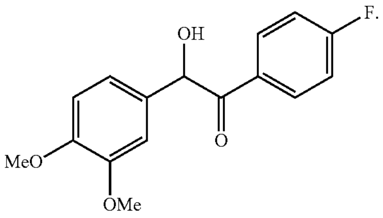

3. A composition comprising Formula Bz-2 or Formula Bz-3:

Formula Bz-2

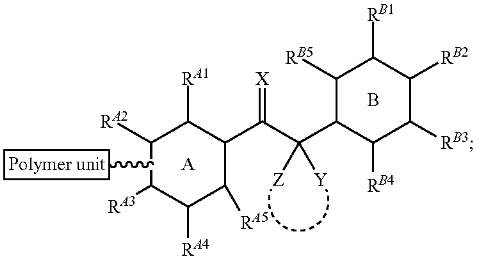

Formula Bz-3

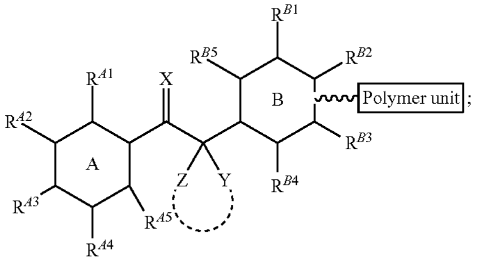

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom;

substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is vinyl, stryl, acryl, or cyclic monomers selected from lactones, epoxides, lactides, lactams, silicon-containing cyclic monomers, and cyclic carbonates;

provided that one of A or B has two methoxy substituents.

4. The composition of claim 3, wherein the composition comprises Bz-2a, Bz-2a-I, Bz-2b, Bz-2b-I, Bz-2c, Bz-2d, Bz-3a, Bz-3a-I, Bz-3b, Bz-3c, or Bz-3d:

Bz-2a
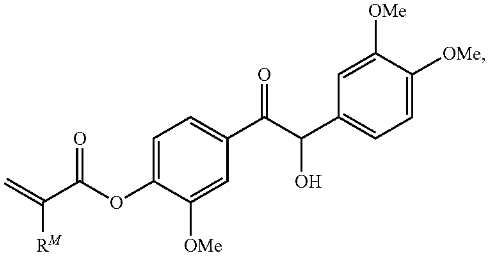
wherein $R^M$ is alkyl, aryl, or heteroaryl;
Bz-2a-I
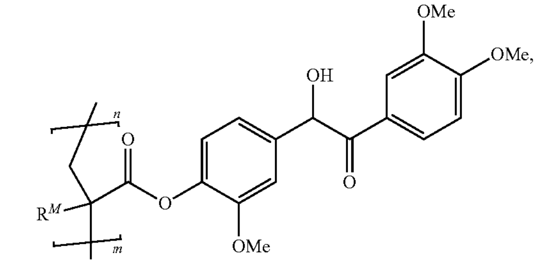
wherein m and n each integers and $R^M$ is alkyl, aryl, or heteroaryl;
Bz-2b
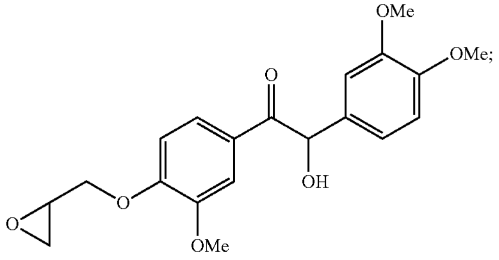
Bz-2b-I
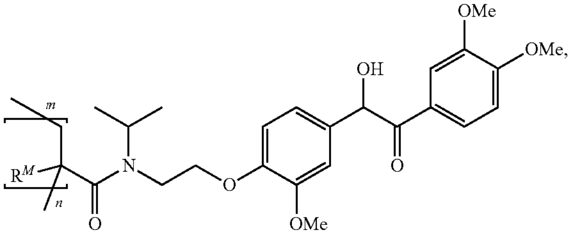
wherein m and n are each integers;
Bz-2c
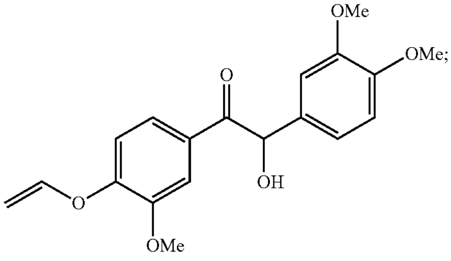
-continued
Bz-2d
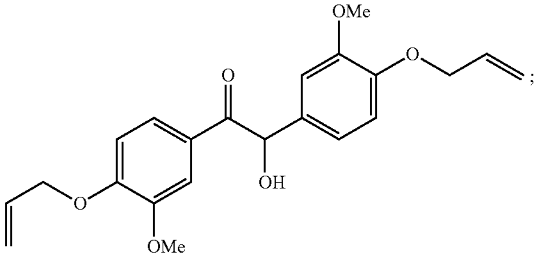
Bz-3a
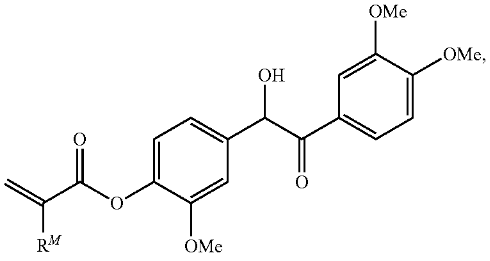
wherein $R^M$ is alkyl, aryl, or heteroaryl;
Bz-3a-I
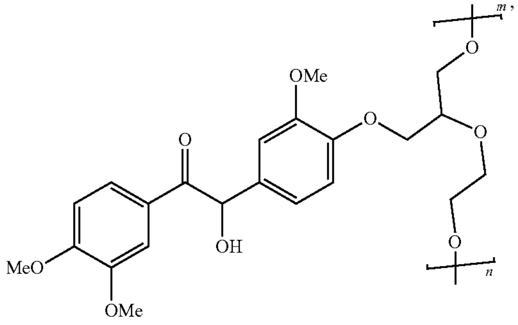
wherein m and n are each integers;
Bz-3b
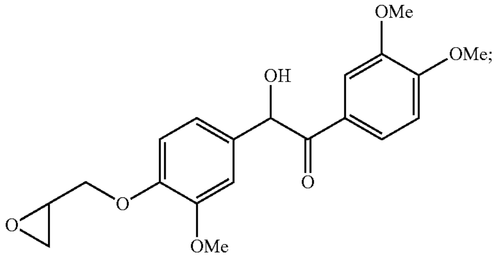

-continued

Bz-3c

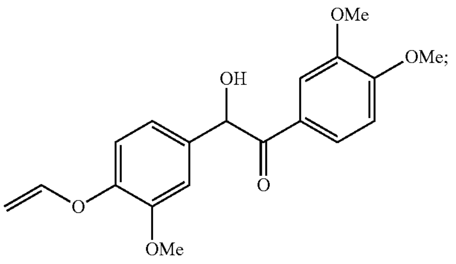

or

Bz-3d

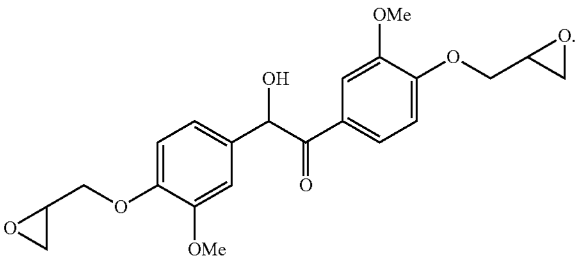

5. A composition comprising Formula Bz-4, Formula Bz-5, Formula Bz-6, or Formula Bz-7:

Formula Bz-4

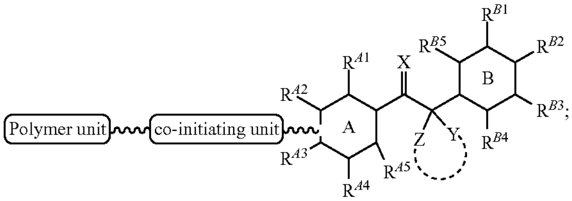

Formula Bz-5

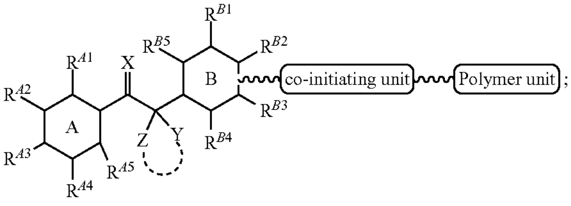

-continued

Formula Bz-6

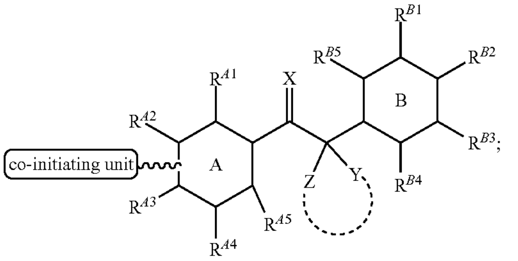

or

Formula Bz-7

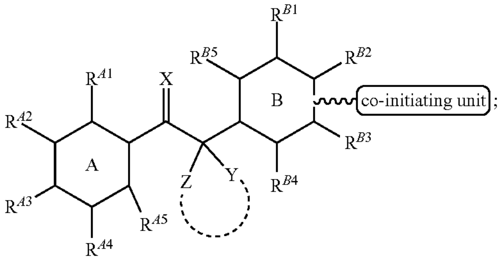

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom;

substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes;

the co-initiating unit is an amine, a thiol, or any hydrogen atom donor; and the polymer unit is vinyl, stryl, acryl, or cyclic monomers selected from lactones, epoxides, lactides, lactams, silicon-containing cyclic monomers, and cyclic carbonates.

6. The composition of claim 5, wherein the composition comprises compound Bz-4a, Bz-5a, Bz-6a, Bz-6b, Bz-6c, Bz-6d, Bz-7a, Bz-7b, Bz-7c, or Bz-7d:

Bz-4a
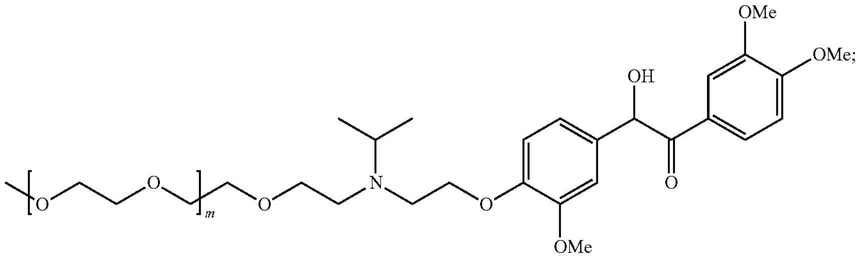
wherein m is an integer;
Bz-5a
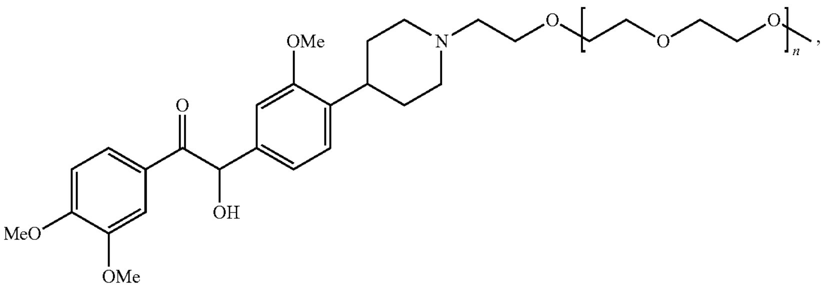
wherein n is an integer;
Bz-6a
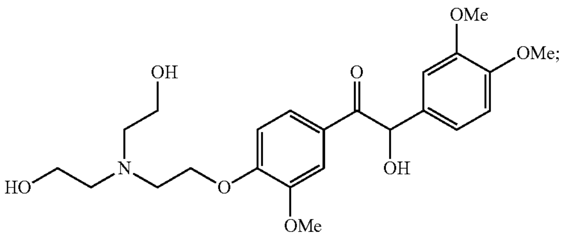
Bz-6b
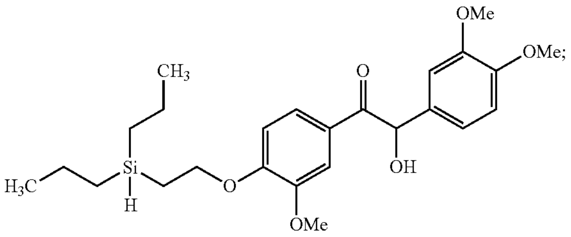
-continued
Bz-6c
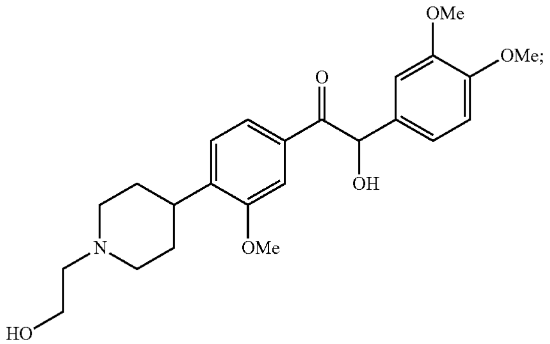
Bz-6d
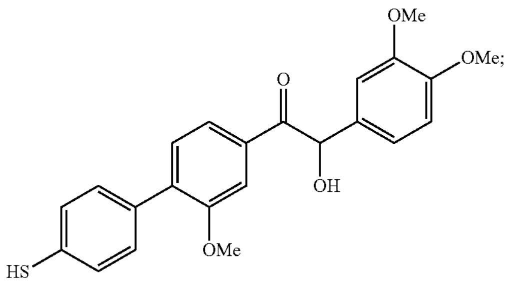

-continued

Bz-7a

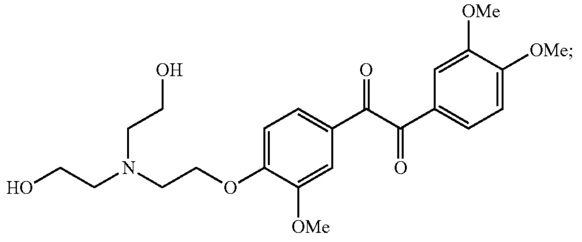

Bz-7b

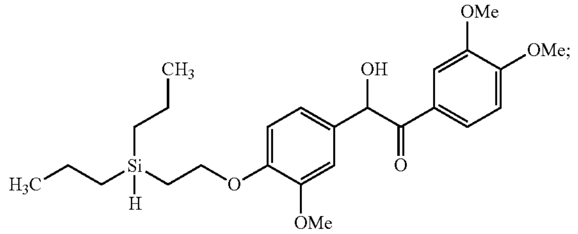

Bz-7c

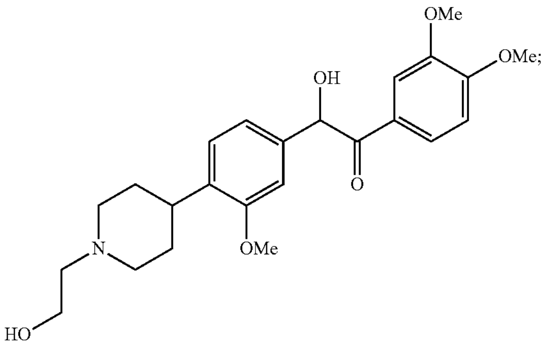

or

Bz-7d

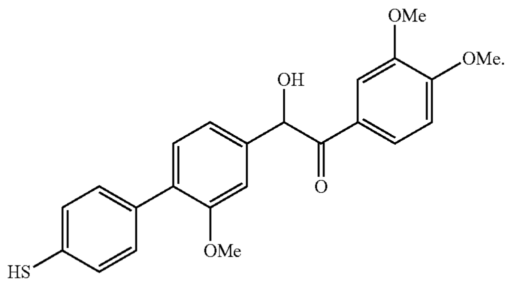

7. A method for making a polymer, the method comprising exposing a photoinitiator and a monomer to light to produce a polymer, wherein the photoinitiator is a biomass derived benzoin derivative having two methoxy substituents on one phenyl ring.

8. The method of claim 7, wherein the photoinitiator comprises Formula Bz-1:

Formula Bz-1

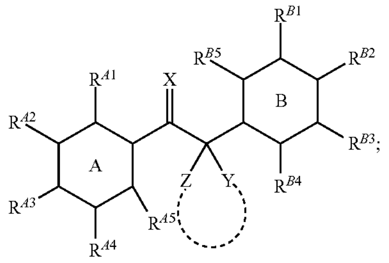

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom;

A or B is a ring derived from biomass; and substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

9. The method of claim 7, wherein the photoinitiator has Formula A:

Formula A

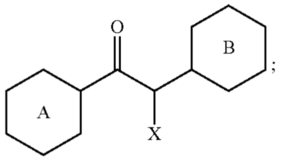

wherein:

A and B each independently represent a carbocycle optionally substituted with one or more electron withdrawing or electron donating substituents; and X comprises OH, an alkoxy, halo, SH, S-alkyl, carboxy, aryloxy, or hetero-atom attached to a carbocycle or a heterocycle.

10. The method of claim 7, wherein the polymer is colorless or transparent.

11. The method of claim 7, wherein the photoinitiator comprises bis-(dimethoxy)-benzoin 1a, para-chlorobenzyl-(dimethoxy)-benzoin 1b, para-cyanobenzyl-(dimethoxy)-benzoin 1c, para-trifluoromethylbenzyl-(dimethoxy)-benzoin 1d, para-chlorobenzoyl-(dimethoxy)-benzoin 1e, para-thiomethylbenzoyl-(dimethoxy)-benzoin 1f, para-thiomethylbenzoyl-(dimethoxy)-benzoin 1g, para-fluorobenzyl-(dimethoxy)-benzoin 1i, or para-fluorobenzyl-(dimethoxy)-benzoin 1j:

1a

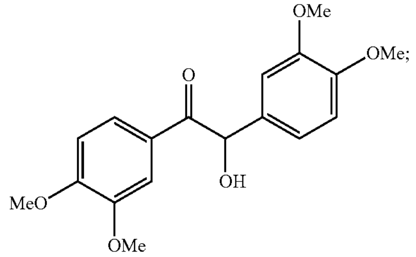

1b

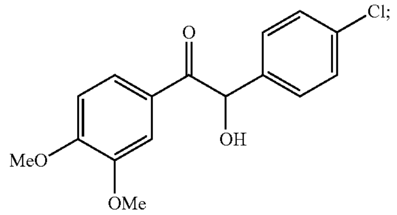

1c

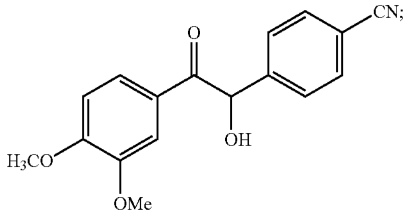

1d

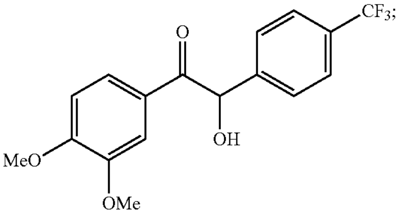

1e

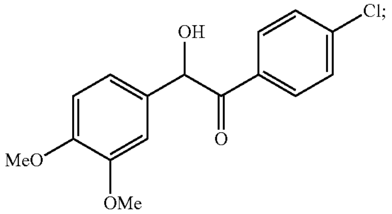

1f

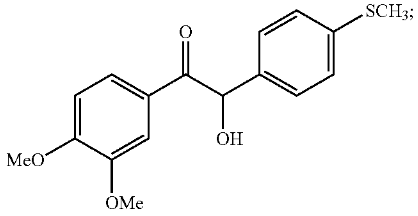

1g

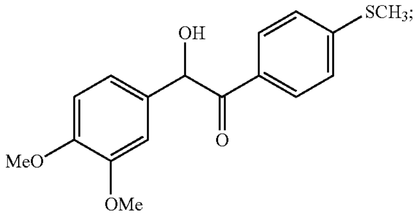

-continued

1i

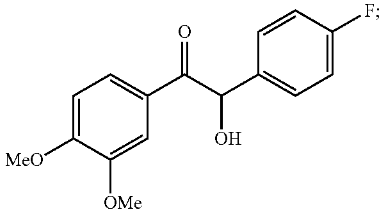

or

1j

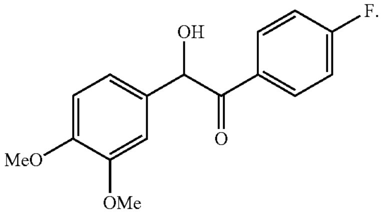

12. The method of claim 7, wherein the photoinitiator comprises Formula Bz-2 or Formula Bz-3:

Formula Bz-2

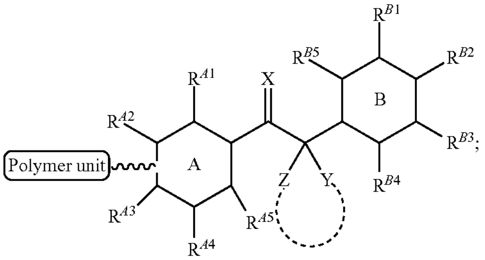

Formula Bz-3

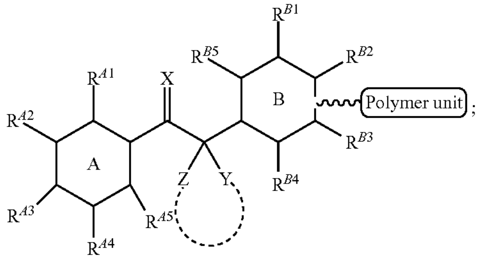

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom;

A or B is a ring derived from biomass;

substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is vinyl, stryl, acryl, or cyclic monomers selected from lactones, epoxides, lactides, lactams, silicon-containing cyclic monomers, and cyclic carbonates.

13. The method of claim 7, wherein the photoinitiator comprises Bz-2a, Bz-2a-I, Bz-2b, Bz-2b-I, Bz-2c, Bz-2d, Bz-3a, Bz-3a-I, Bz-3b, Bz-3c, or Bz-3d:

Bz-2a

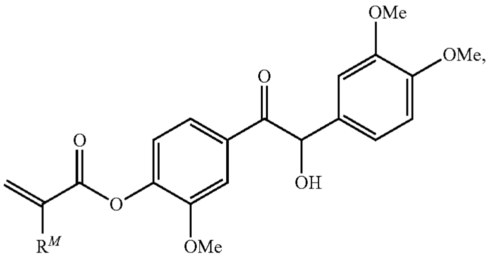

wherein $R^M$ is alkyl, aryl, or heteroaryl;

Bz-2a-I

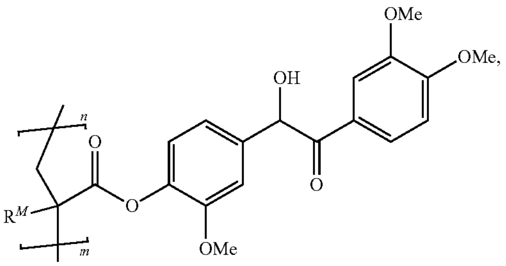

wherein m and n each integers and $R^M$ is alkyl, aryl, or heteroaryl;

Bz-2b

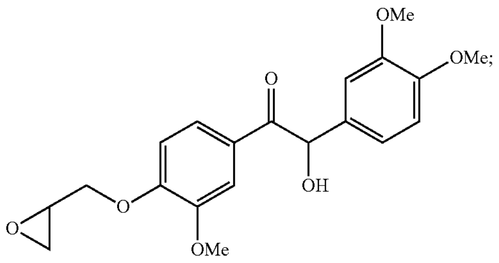

Bz-2b-I

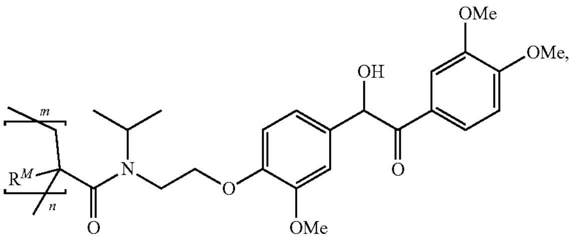

wherein m and n are each integers;

Bz-2c

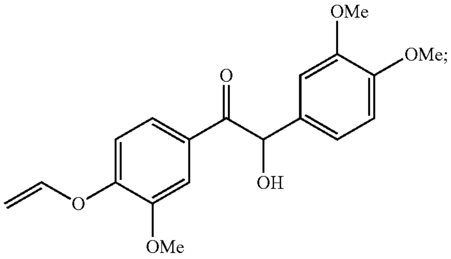

Bz-2d

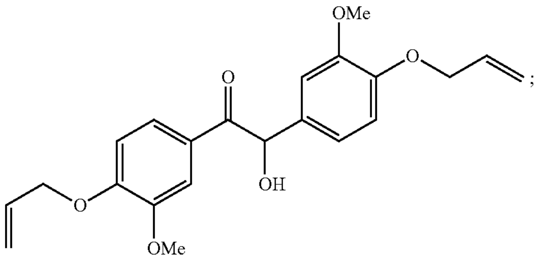

Bz-3a

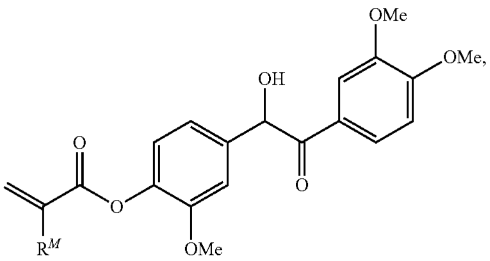

wherein $R^M$ is alkyl, aryl, or heteroaryl;

Bz-3a

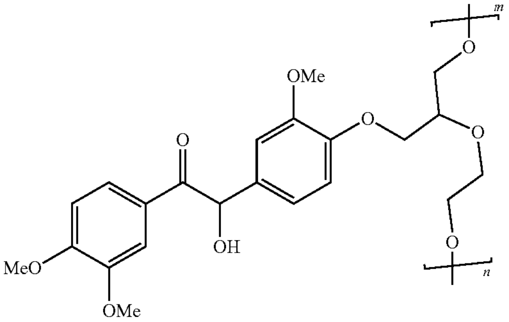

-continued

Bz-3a-I

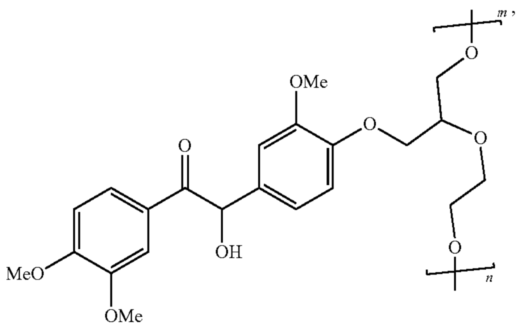

wherein m and n are each integers;

Bz-3b

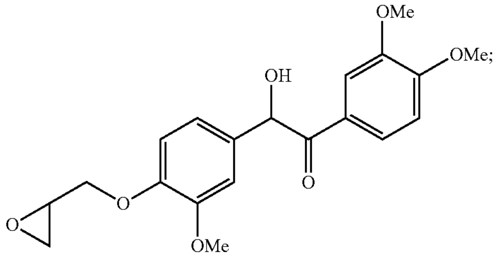

Bz-3c

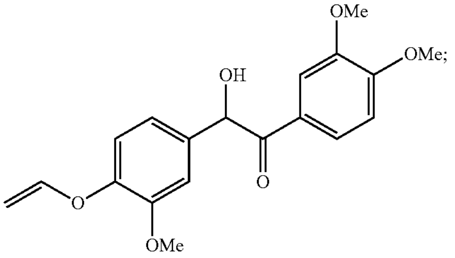

Bz-3d

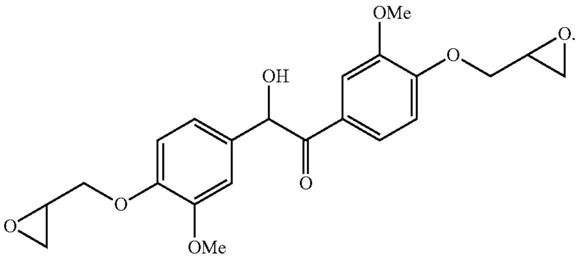

14. The method of claim 7, wherein the photoinitiator comprises Formula Bz-4, Formula Bz-5, Formula Bz-6, or Formula Bz-7:

Formula Bz-4

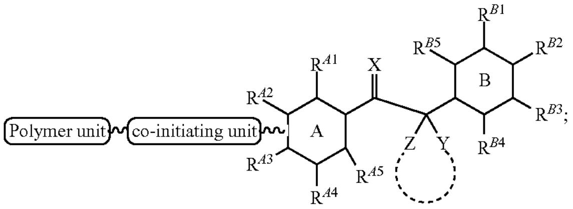

Formula Bz-5

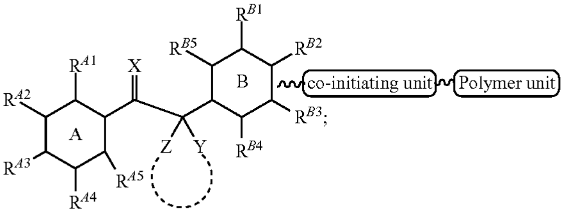

;

Formula Bz-6

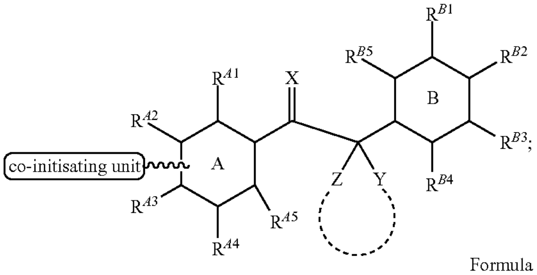

or

Formula Bz-7

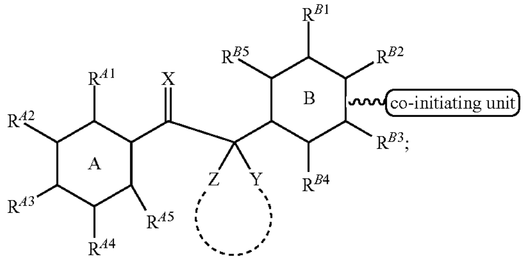

;

wherein:

dashed lines indicate optional bonds;

X is O, S, NH, Ge, NC(O)—O—$R^C$, N—O—C(O)$R^C$, or NO—$R^C$, wherein $R^C$ is alkyl, aryl, or heteroaryl;

each of A and B is a phenyl ring;

Z is OH or H;

Y is OH, alkoxy, halo, SH, S-alkyl, carboxy, aryloxy, or a hetero-atom;

A or B is a ring derived from biomass;

substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes;

the co-initiating unit is an amine, a thiol, or any hydrogen atom donor; and the polymer unit is vinyl, stryl, acryl, or cyclic monomers selected from lactones, epoxides, lactides, lactams, silicon-containing cyclic monomers, and cyclic carbonates.

15. The method of claim 7, wherein the photoinitiator comprises compound Bz-4a, Bz-5a, Bz-6a, Bz-6b, Bz-6c, Bz-6d, Bz-7a, Bz-7b, Bz-7c, or Bz-7d:
Bz-4a
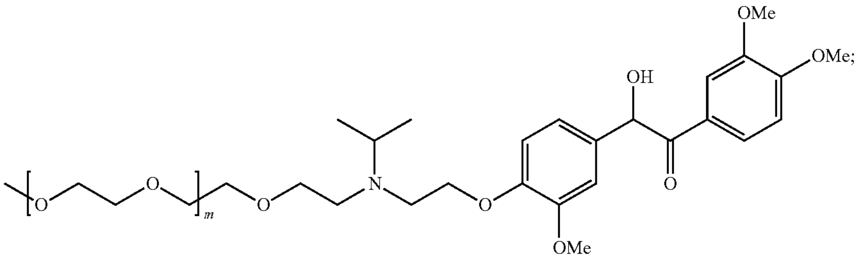
wherein m is an integer; or
Bz-5a
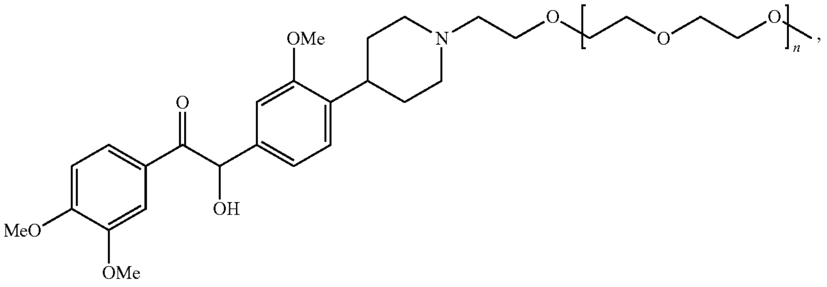
wherein n is an integer;
Bz-6a
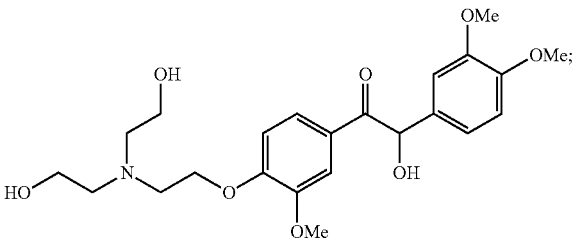
Bz-6b
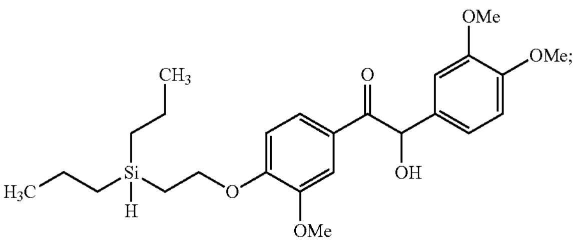
-continued
Bz-6c
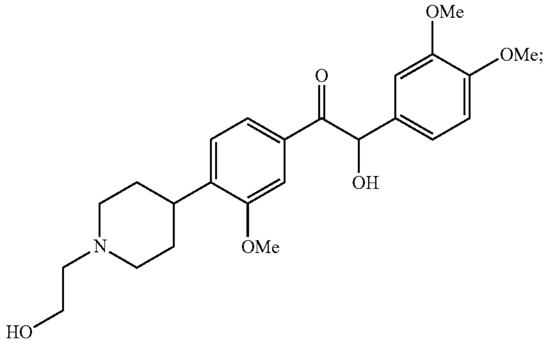
Bz-6d
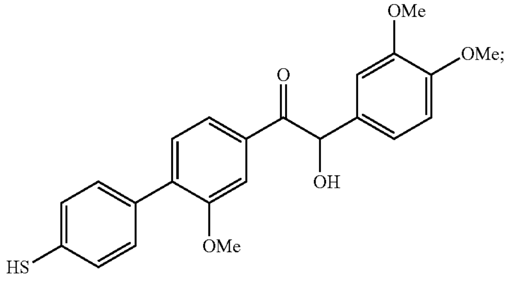

-continued

Bz-7a

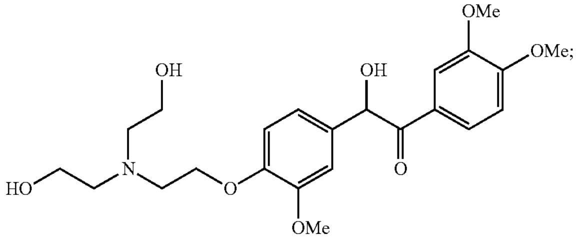

Bz-7b

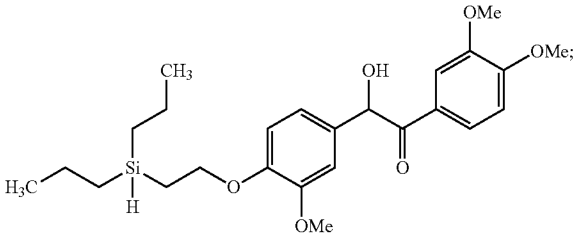

Bz-7c

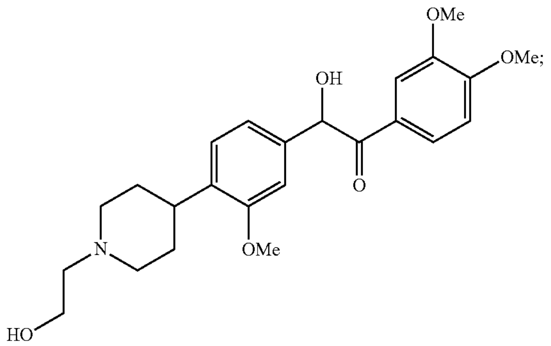

-continued or

Bz-7d

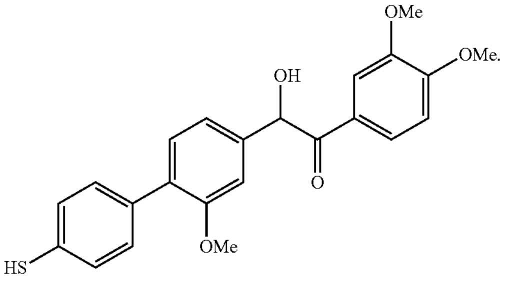

16. The method of claim 7, wherein the photoinitiator is prepared from biomass.

17. The method of claim 7, wherein the light is visible light.

18. The method of claim 7, wherein the light is purple light or blue light.

19. The method of claim 7, wherein the monomer is methylmethacrylate 4 or polymer 5:

4

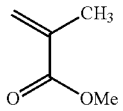

or

5

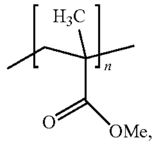

wherein n is an integer.

20. The method of claim 7, wherein a co-initiator is exposed to the light with the photoinitiator and the monomer.

* * * * *